US006899870B1

(12) United States Patent
McDonnell et al.

(10) Patent No.: US 6,899,870 B1
(45) Date of Patent: May 31, 2005

(54) INDUCTION OF APOPTIC OR CYTOTOXIC GENE EXPRESSION BY ADENOVIRAL MEDIATED GENE CODELIVERY

(75) Inventors: Timothy J. McDonnell, Houston, TX (US); Stephen G. Swisher, Fresno, TX (US); Bingliang Fang, Houston, TX (US); Elizabeth M. Bruckheimer, Houston, TX (US); Mona G. Sarkiss, Houston, TX (US); Lin Ji, SugarLand, TX (US); Jack A. Roth, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 641 days.

(21) Appl. No.: 09/266,465

(22) Filed: Mar. 11, 1999

Related U.S. Application Data

(60) Provisional application No. 60/077,541, filed on Mar. 11, 1998.

(51) Int. Cl.$^7$ ...................... A61K 48/00; C12N 15/861; C12N 15/63; C07H 21/04
(52) U.S. Cl. .................... 424/93.2; 424/93.1; 424/93.6; 435/320.1; 435/69.1; 435/455; 435/456; 435/457; 536/23.1; 536/23.2; 536/23.4; 536/23.5; 536/24.1
(58) Field of Search .......................... 435/320.1, 235.1, 435/69.1, 455, 456, 457; 424/93.1, 93.2, 93.6; 536/23.1, 23.2, 23.4, 23.5, 24.1

(56) References Cited

U.S. PATENT DOCUMENTS 6,143,291 A * 11/2000 June et al. ................ 424/93.21
6,194,191 B1 * 2/2001 Zhang et al. ................ 435/239

OTHER PUBLICATIONS

James W. Lillie et al, Transcription activation by the adenovirus E1a protein, nature vol. 338, Mar. 2, 1989.*
Randal J. Kaufman, Vectors Used For Expression, Methods in Enzymology, vol. 185, 1990.*
Coll et al., "Antitumor activity of *bax* and *p53* naked gene transfer in lung cancer: in vitro and in vivo analysis," *Human Gene Therapy*, 9:2063–2074, 1998.
"One way to kill cancer: give it a cold," www.cnn.com, pp. 1–4, May 20, 1997.
Sakakura et al., "Overexpression of bax sensitizes human breast cnacer MCF–7 cells to radiation–induced apoptosis," *Int. J. Cancer*, 67:101–105, 1996.
Vogelbaum, et al., "Transfection of C6 glioma cells with the *bax* gene and increased sensitivity to treatment with cytosine arabinoside," *J. Neurosurg*, 88:99–105, 1998.
Chittenden et al., "Induction of apoptosis by the Bcl–2 homologue Bak," *Nature*, 374:733–736, 1995.
Fang et al., "Evaluation of GLA4/TATA in vivo," *J. Biol. Chem.*, 273:4972–4975, 1988.

Krajewski et al., "Immunohistochemical determination of in vivo distribution of Bax, a dominant inhibitor of Bcl–2," *Am J. Pathol.*, 145:1323–1336, 1994.
Krajewski et al., "Immunohistochemical analysis of in vivo patterns of *Bak* expression, a propoptotic member of the Bcl–2 protein family," *Cancer Res.*, 56:2849–2855, 1996.
McDonnell et al., "Expression of Bcl–2 oncoprotein and p53 proten accumulation in bone marrow metastases of androgen independent prostate cancer," *J. Urology*, 157:569–574, 1997.
Merchant et al., "Expression of wild–type p53 simulates an increase in both Bax and Bcl–$x_L$ protein content in HT29 cells," *Oncogene*, 13:2631–2637, 1996.
Miyashita et al., "Identification of a p53–dependent negative response element in the *bcl–2* gene," *Cancer Res.*, 54:3131–3135, 1994.
Miyashita et al., "Tumor suppressor p53 is a direct transcriptional activator of the human *bax* gene," *Cell*, 80:293–299, 1995.
Miyashita et al., "Tumor suppressor p53 is a regulator of *bcl–2* and *bax* gene expression in vitro and in vivo," *Oncogene*, 9:1799–1805, 1994.
Oligino et al., "In vivo transgene activation from an HSV–based gene therapy vector by GAL4:VP16," *Gene Ther.*, 3:892–899, 1996.
Ouyang et al., "The BAX gene, the promoter of apoptosis, is mutated in genetically unstable cancers of the colorectum, stomach, and endometrium," *Clin. Cancer Res.* 4:1071–1074, 1998.
Pastorino et al., "The overexpression of Bax produces cell death upon induction of the mitochondrial permeability transition," *J. Biol. Chem.* 273:7770–7775, 1998.
Sakakura et al., "Overexpression of bax sensitizes human breast cancer MCF–7 cells to radiation–induced apoptosis," *Int. J. Cancer* 67:101–105, 1996.
Wang et al., "Posititve and negative regulation of gene expression in eukaryotic cells with an inducible transcriptional regulator," *Gene Ther.*, 4:432–441, 1997.
Wyllie, "Death gets a brake," *Nature*, 369:272–273, 1994.
Yin et al., "Bax suppresses tumorigenesis and stimulates apoptosis in vivo," *Nature* 385:637–640, 1997.
Yin et al., "Heterodimierization with bax is required for Bcl–2 to repress cell death," *Curr. Top. Microbiol. Immunol.*, 194:331–337, 1995.
Yin et al., "BH1 and BH2 domains of Bcl–2 are required for inhibition of apoptosis and heterodimerization with Bax," *Nature*, 369:321–323, 1994.

* cited by examiner

*Primary Examiner*—David Guzo
(74) *Attorney, Agent, or Firm*—Fulbright & Jaworski

(57) ABSTRACT

The present invention generally relates to viral vectors and their use as expression vectors for transforming human cells, both in vitro and in vivo. More particularly, the present invention relates to adenoviral vectors containing propapoptotic genes and their use in cancer therapy.

49 Claims, 16 Drawing Sheets

INDUCTION OF APOPTIC OR CYTOTOXIC GENE EXPRESSION BY ADENOVIRAL MEDIATED GENE CODELIVERY

This application claims priority to and specifically incorporates by reference, the content of U.S. Provisional Application Ser. No. 60/077,541 filed Mar. 11, 1998. The entire text of each of the above-referenced disclosures is specifically incorporated by reference herein without disclaimer. The government owns rights in the present invention pursuant to grant number CA70907 from the National Institutes of Health.

BACKGROUND OF THE INVENTION

1. Field of the Invention

The present invention relates generally to viral vectors and their use as expression vectors for transforming human cells, both in vitro and in vivo. More specifically, the invention relates to adenoviral expression constructs comprising a proapoptotic member of the Bcl-2 gene family.

2. Description of Related Art

Adenoviral vectors have become one of the leading vectors for gene transfer, particularly in gene therapy contexts. These vectors have been studied rigorously in both in vitro and in vivo contexts because of the ability to generate high titer stocks, their high transduction efficiency and their ability to infect a variety of tissue types in different species. In addition, the availability of cell lines to complement defects in adenoviral replication functions provides for the use of replication defective mutants carrying, in the place of selected structural genes, recombinant inserts of interest.

Several studies have demonstrated the ability of adenovirus-mediated wild-type p53 replacement gene therapy to induce a $G_1$ cell cycle arrest and/or apoptosis in malignant cells carrying p53 gene mutations. Though the mechanism of $G_1$ arrest via p21 and the cyclin-dependent kinase pathway has been widely studied, little is known of the mechanisms by which wild-type p53 induces apoptosis. It appears that p53 induces apoptosis, at least in part, by up-regulating proapoptotic members of the Bcl-2 family of proteins.

The Bcl-2 family of proteins and ICE-like proteases have been demonstrated to be important regulators and effectors of apoptosis in other systems. Apoptosis, or programmed cell death, is an essential occurring process for normal embryonic development, maintaining homeostasis in adult tissues, and suppressing carcinogenesis (Kerr et al., 1972). The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins which can be categorized as death agonists or death antagonists.

Subsequent to its discovery, it was shown that Bcl-2 acts to suppress cell death triggered by a variety of stimuli which will be discussed in detail. Also, it now is apparent that there is a family of Bcl-2 cell death regulatory proteins which share in common structural and sequence homologies. These different family members have been shown to either possess similar functions to Bcl-2 or counteract Bcl-2 function and promote cell death.

One such family member having Bcl-2 counteracting function is Bax. Bax, Bcl-2 associated X protein, is a death agonist member of the Bcl-2 family of proteins (Oltvai et al., 1993). It has been suggested that Bax may function as a primary response gene in a p53 regulated apoptotic pathway (Miyashita et al., 1994). Indeed, it has been shown that there is a p53 consensus binding region in the promoter region of the proapoptotic Bax gene (1995). Bax mRNA and protein expression are increased following induction of p53. However, the observed induction of p53-dependent apoptosis in Bax knock out mice clearly indicates that other pathways or proteins are involved. Bak, a Bcl-2 homologue, is expressed in a variety of tissues and has been demonstrated to induce program cell death independent of Bax expression (Krajewski et al., 1996; Chittenden et al., 1995). The accumulation of Bak protein in cells infected with Adp53, may be an additional mechanism by which p53 can induce programmed cell death.

However, a recent report has demonstrated an increase in Bcl-$x_L$, expression following wild-type p53 expression in the human colorectal cancer cell line HT29 (Merchant et al., 1996). The authors hypothesize that this increase expression may lead to an inhibition of program cell death pathways and accounted for lack of p53-induced apoptosis observed in these cells. Another potential problem with p53 therapy is that the amount of viral material administered provides risks of host cell toxicity and/or immune response. Thus, any method which would increase the effect of p53 at low doses, or circumvent the need for high viral doses, would be advantageous.

Given that p53 gene therapy is a powerful tool in the fight against cancer, therapeutic compositions that may augment or complement p53 will serve to improve the currently available cancer therapy regimens. Indeed, compositions that provide the apoptotic effect of p53 without the need for p53 itself would be additionally useful.

SUMMARY OF THE INVENTION

The present invention generally is related the use of viral vectors containing propapoptotic genes and their use in cancer therapy, in order to induce an apoptotic effect in cancer cells to either augment, complement or bypass the need for p53 based therapy.

In order to achieve the objectives of the present invention, a particular embodiment provides an adenoviral expression construct comprising a nucleic acid encoding a proapoptotic member of the Bcl-2 gene family and a first promoter functional in eukaryotic cells wherein the nucleic acid is under transcriptional control of the first promoter. In particularly preferred embodiments, the proapoptotic Bcl-2 gene is a Bax, Bak, Bim, Bik, Bid or Bad gene. In certain embodiments, it is contemplated that the adenoviral expression construct may further comprise a second nucleic acid encoding a second gene. In particular instances the second nucleic acid is under the control of the first promoter.

In particularly preferred embodiments, the proapoptotic Bcl-2 gene and the second nucleic acid are separated by an IRES. In alternative embodiments, the second nucleic acid is under the control of a second promoter operative in eukaryotic cells. It is contemplated that the promoter employed herein may be any promoter used in the production of expression constructs. In particularly preferred embodiments the promoter may be selected from the group consisting of CMV IE, SV40 IE, RSV, β-actin, tetracycline regulatable and ecdysone regulatable.

In certain defined aspects, the second gene may encode a protein selected from the group consisting of a tumor suppressor, a cytokine, a receptor, inducer of apoptosis, and differentiating agents. By "differentiating agents," the present application refers to the function of bcl-2 family members in the induction of differentiation in cells. Thus, the cells are not induced to die via apoptosis, but terminally differentiate and stop growing, which is equally effective as a cancer treatment. In particularly preferred embodiments, the tumor suppressor may be selected from the group consisting of p53, p16, p21, MMAC1, p73, zac1, C-CAM, BRCAI and Rb. In certain embodiments, the inducer of apoptosis is selected from the group consisting of Harakiri, Ad E1B and an ICE-CED3 protease. In those embodiments employing a cytokine, the cytokine may be selected from the group consisting of IL-2, IL-2, IL-3, IL-4, IL-5, IL-6, IL-7, IL-8, IL-9, IL-10, IL-11, IL-12, IL-13, IL-14, IL-15, TNF, GMCSF, β-interferon and γ-interferon. In those embodiments where the second gene is a receptor, the receptor may be selected from the group consisting of CFTR, EGFR, VEGFR, IL-2 receptor and the estrogen receptor. It is contemplated that the second nucleic acid may be an antiapoptotic member of the Bcl-2 gene family or an oncogene, the second nucleic acid being positioned in an antisense orientation with respect to the promoter. In more preferred embodiments, the antiapoptotic member of the Bcl-2 gene family is Bcl-2 or Bcl-$x_L$. In embodiments in which the second gene is an oncogene, the oncogene may be selected from the group consisting of ras, myc, neu, raf, erb, src, fms, jun, trk, ret, gsp, hst, and abl.

In defined embodiments, the expression construct is a replication-deficient adenovirus. In preferred aspects, the adenovirus lacks at least a portion of the E1 region. In other embodiments, the adenovirus further lacks the E3 coding region. In preferred embodiments, the expression construct further comprises a polyadenylation signal. In particular embodiments, the nucleic acid may be a cDNA, or genomic DNA.

In particularly preferred embodiments, the proapoptotic member of the Bcl-2 family is Bax. In other preferred embodiments, the proapoptotic member of the Bcl-2 family is Bak. In more preferred embodiments, the Bax CDNA expresses a truncated Bax protein. In more preferred embodiments, the truncated Bax protein comprises an intact death domain. In other preferred embodiments, the truncated Bax protein comprises SEQ ID NO:2. In other preferred embodiments, the truncated Bax protein comprises a BH3 region.

Also contemplated by the present invention is a pharmaceutical composition comprising a first adenoviral expression construct comprising a promoter functional in eukaryotic cells and a first nucleic acid encoding a proapoptotic member of the Bcl-2 gene family, wherein the first nucleic acid is under transcriptional control of the promoter and a pharmaceutically acceptable buffer, solvent or diluent.

In particularly preferred embodiments, the proapoptotic Bcl-2 family gene is a Bax, Bak, Bik, Bid, or Bad gene. In other preferred embodiments, the promoter may be selected from the group consisting of CMV IE, SV40 IE, RSV, β-actin, tetracycline regulatable and ecdysone regulatable. In other embodiments, the pharmaceutical composition may further comprise a second expression construct encoding a second nucleic acid encoding a second gene operatively linked to a second promoter. In certain aspects, the expression construct encoding the proapoptotic gene further comprises a second nucleic acid encoding a second gene. The second nucleic acid may be under the control of the first promoter. In alternative embodiments, the second nucleic acid is under the control of a second promoter operative in eukaryotic cells. The second gene may encode a protein selected from the group consisting of a tumor suppressor, a cytokine, a receptor, inducer of apoptosis, and differentiating agents. In particularly preferred embodiments, the second nucleic acid is an antiapoptotic member of the Bcl-2 gene family or an oncogene, the second nucleic acid being positioned in an antisense orientation with respect to the promoter.

In preferred embodiments, the present invention further contemplates a method for treating a subject with cancer comprising the steps of providing an adenoviral expression construct comprising a nucleic acid encoding a proapoptotic member of the Bcl-2 gene family and a first promoter functional in eukaryotic cells wherein the nucleic acid is under transcriptional control of the first promoter; and contacting the expression construct with cancer cells of the subject in a manner that allows the uptake of the expression construct by the cells, wherein expression of the proapoptotic gene results in the treatment of the cancer. By "treatment," the present invention refers to any event that decreases the growth, kills or otherwise abrogates the presence of cancer cells in a subject. Such a treatment may also occur by inhibition of the metastatic potential or inhibition of tumorigenicity of the cell so as to achieve a therapeutic outcome.

In other preferred aspects, the method further comprises contacting the cancer cell with a further cancer therapeutic agent. In particularly preferred embodiments, the cancer therapeutic agent may be selected from the group consisting of tumor irradiation, chemotherapeutic agent, a second nucleic acid encoding a cancer therapeutic gene. In defined embodiments, the chemotherapeutic agent is a DNA damaging agent selected from the group consisting of verapamil, podophyllotoxin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate. In alternative embodiments, the radiation is selected from the group consisting of X-ray radiation, UV-radiation, γ-radiation, or microwave radiation. In other defined embodiments, the cancer therapeutic agent comprises a second nucleic acid. The second nucleic acid may be a cDNA or genomic DNA.

In particular embodiments of the present invention, the second expression construct is selected from the group consisting of an adenovirus, an adeno-associated virus, a vaccinia virus and a herpesvirus. In other embodiments, the contacting is effected by regional delivery of the expression construct. In alternative embodiments, the contacting is effected by local delivery of the expression construct. In still further embodiments, the contacting may be effected by direct injection of a tumor with the expression construct. In particularly preferred embodiments, the contacting comprises delivering the expression construct endoscopically, intratracheally, intralesionally, percutaneously, intravenously, subcutaneously or intratumorally to said subject. In certain embodiments, the method may further comprise the step of tumor resection. The tumor resection may occur prior to or after the contacting. The tumor resection may be performed one, two, three or more times. In particularly preferred embodiments, the cancer being treated may be selected from the group consisting of lung, breast, melanoma, colon, renal, testicular, ovarian, lung, prostate, hepatic, germ cancer, epithelial, prostate, head and neck, pancreatic cancer, glioblastoma, astrocytoma, oligodendroglioma, ependymomas, neurofibrosarcoma, meningia, liver, spleen, lymph node, small intestine, blood cells, colon, stomach, thyroid, endometrium, prostate, skin, esophagus, bone marrow and blood.

The present invention also provides a method of inhibiting the growth of a cell comprising the steps of providing an adenoviral expression construct comprising a nucleic acid encoding a proapoptotic member of the Bcl-2 gene family and promoter functional in eukaryotic cells wherein the nucleic acid is under transcriptional control of the first promoter; and contacting the expression construct with the cell in an amount effective to inhibit the growth of the cell wherein expression of the proapoptotic gene by the cell results in a decrease in the growth of the cell relative to the growth of the cell in the absence of the proapoptotic gene.

In preferred embodiments, the cell is a cancer cell. In other preferred embodiments, the inhibition of growth comprises killing of the cancer cell. In other embodiments, the inhibition of growth comprises an inhibition of metastatic growth of the cancer cell. In defined embodiments, the cancer cell may be selected from the group consisting of lung, breast, melanoma, colon, renal, testicular, ovarian, lung, prostate, hepatic, germ cancer, epithelial, prostate, head and neck, pancreatic cancer, glioblastoma, astrocytoma, oligodendroglioma, ependymomas, neurofibrosarcoma, meningia, liver, spleen, lymph node, small intestine, blood cells, colon, stomach, thyroid, endometrium, prostate, skin, esophagus, bone marrow and blood. In other embodiments, the cell is located within a mammal.

The present invention also provides a method of inducing apoptosis in a cell comprising the steps of providing an adenoviral expression construct comprising a nucleic acid encoding a proapoptotic member of the Bcl-2 gene family and promoter functional in eukaryotic cells wherein the nucleic acid is under transcriptional control of the first promoter; and contacting the expression construct with the cell in an amount effective to kill the cell; wherein expression of the proapoptotic gene by the results in an increase in the rate of death of said cell relative to the growth of said cell in the absence of said proapoptotic gene. In particularly preferred embodiments, the proapoptotic member of the Bcl-2 gene family is a Bax, Bak, Bim, Bik, Bid or Bad gene. In more preferred embodiments, the proapoptotic member of the Bcl-2 gene family is a truncated Bax gene. In other preferred embodiments, the proapoptotic member of the Bcl-2 gene family is a truncated Bak gene.

Also contemplated by the present invention is a nucleic acid encoding a truncated Bax gene. In particular embodiments, the Bax gene comprises a nucleic acid sequence of SEQ ID NO: 1. In other embodiments, the Bax gene encodes a protein having an amino acid sequence of SEQ ID NO:2. In particularly preferred aspects the truncated Bax gene encodes a protein comprising a BH3 region. In alternative preferred embodiments, the truncated Bax gene encodes a protein comprising an intact death domain.

In yet another embodiment, the present invention further contemplates an adenoviral expression construct comprising a nucleic acid encoding a truncated Bax gene and a first promoter functional in eukaryotic cells wherein the nucleic acid is under transcriptional control of the first promoter. The adenoviral expression construct may further comprise a second nucleic acid encoding a second gene. The second gene may be under the control of the first promoter. In alternative embodiments, the second gene may be under the transcriptional control of a second promoter. In a further alternative, the truncated Bax gene and the second nucleic acid may be separated by an IRES.

In yet another embodiment, the present invention further contemplates an adenoviral expression construct comprising a nucleic acid encoding a bak gene and a first promoter functional in eukaryotic cells wherein the nucleic acid is under transcriptional control of the first promoter. The adenoviral expression construct may further comprise a second nucleic acid encoding a second gene. The second gene may be under the control of the first promoter. In alternative embodiments, the second gene may be under the transcriptional control of a second promoter. In a further alternative, the truncated Bak gene and the second nucleic acid may be separated by an IRES.

In other embodiments there is provided, a method for expressing a polypeptide in a target cell comprising introducing into the target cell a first vector comprising a coding region for a polypeptide under the control of a first promoter inducible by an inducer polypeptide not expressed in the target cell and a second vector comprising a coding region for the inducer polypeptide tinder the control of a second promoter active in the target cell. In certain embodiments, the first and second vectors are viral vectors. In other embodiments, the first and said second vectors are non-viral vectors. In yet other embodiments, the first vector is a viral vector and the second vector is a non-viral vector, or the first vector is a non-viral vector and the second vector is a viral vector. It is contemplated that the second promoter is a constitutive promoter, an inducible promoter or a tissue specific promoter.

In certain embodiments, the viral vectors are the same or different and may be selected from the group consisting of an adenoviral vector, a herpesviral vector, a retroviral vector, an adeno-associated viral vector, a vaccinia viral vector or a polyoma viral vector.

It is contemplated in one embodiment that the first vector and the second vector are introduced into the target cell at a ratio of 1:1, respectively. In other embodiments, the first vector and the second vector are introduced into the target cell at a ratio of 2:1, respectively. In still other embodiments, the first vector is introduced at 900 MOI and the second vector at 1500 MOI into the target cell.

In another embodiment, the first promoter is GAL4 and the inducer polypeptide is GAL4/VP16, respectively. It is contemplated in other embodiments, that the first promoter can be selected from the group consisting of the ecdysone-responsive promoter, and Tet-On™ and the inducer ecdysone or muristeron A and doxycycline, respectively.

In particular embodiments, the target cell is a hyperproliferative cell, a pre-malignant cell or a malignant cell. In embodiments where the target cell is malignant, it is contemplated that the malignant cell may be selected form the group consisting of a lung cancer cell, a prostate cancer cell, a brain cancer cell, a liver cancer cell, a breast cancer cell, a skin cancer cell, an ovarian cancer cell, a testicular cancer cell, a stomach cancer cell, a pancreatic cancer cell, a colon cancer cell, an esophageal cancer cell, head and neck cancer cell.

In certain embodiments, the first and second vectors are introduced into the target cell at the same time. In one embodiment, the first vector is introduced into the target cell prior to the second vector. In other embodiments, the second vector is introduced into the target cell within 24 hours, within 12 hours, within 6 hours, within 3 hours or within 1 hour of the first vector. In another embodiment, the second vector is introduced into the target cell prior to the first vector. It is contemplated, that the first vector is introduced into the target cell within 24 hours, within 12 hours, within 6 hours, within 3 hours or within 1 hour of the second vector.

In other embodiments, the target cell is further contacted with a DNA damaging agent. It is contemplated that the DNA damaging agent may be radiotherapy or chemotherapy.

In one embodiment, the second promoter is an inducible promoter and the inducing factor is present in the target cell. In another embodiment, the second promoter is an inducible promoter and the inducing factor is added to the target cell. In particular embodiments, it is contemplated that one or both of the vectors further comprise a polyadenylation signal.

In certain embodiments, the polypeptide expressed in the target cell is cytotoxic. It is contemplated that the cytotoxic polypeptide may selected from the group consisting of an inducer of apoptosis, a cytokine, a toxin, a single chain antibody, a protease and an antigen. It is further contemplated that the inducer of apoptosis may be selected from the group consisting of Bax, Bak, Bik, Bim, Bid, Bad and Harakiri. In preferred embodiments, the inducer of apoptosis is Bax. In other embodiments, it is contemplated that the cytokine may be selected form the group consisting of oncostatin M, TGF-β, TNF-α and TNF-β. In yet other embodiments, the toxin may be selected form the group consisting of ricin A-chain, diphtheria toxin A-chain, pertussis toxin A subunit, E coli enterotoxin A subunit, cholera toxin A subunit and pseudomonas toxin c-terminal. In particularly preferred embodiments, the toxin is diphtheria toxin A-chain.

In one embodiment, a kit comprising a first vector comprising a first promoter, inducible by an inducer polypeptide, a multipurpose cloning site 3' to the first promoter in a suitable container and a second vector comprising a coding region for the inducer polypeptide under the control of a second promoter active in the target cell in suitable container. In another embodiment, the first vector further comprises a region coding for a polypeptide under control of the first promoter. In yet another embodiment, the second promoter is an inducible promoter and the kit further comprises an agent that induces the second promoter in a suitable container means.

Also contemplated is a method of treating a disease comprising introducing into cells of a subject having a disease a first vector comprising a coding region for the therapeutic polypeptide under the control of a first promoter inducible by an inducer polypeptide not expressed in the target cell and a second vector comprising a coding region for the inducer polypeptide under the control of a second promoter active in the target cell. In one embodiment, the disease may be selected from the group consisting of lung cancer, prostate cancer, brain cancer, liver cancer, breast cancer, skin cancer, ovarian cancer, testicular cancer, stomach cancer, pancreatic cancer, colon cancer, esophageal cancer and head and neck cancer. In another embodiment, the therapeutic polypeptide may be selected from the group consisting of Bax, Bak, Bik, Bim, Bid, Bad, Harakiri, ricin A-chain, diphtheria toxin A-chain, pertussis toxin A subunit, E. coli enterotoxin A subunit, cholera toxin A subunit, pseudomonas toxin c-terminal, IL-1, IL-2, IL-3, IL-4, IL-5, IL-6, IL-7, IL-8, IL-9, IL-10, IL-11 IL-12, GM-CSF oncostatin M, TGF-β, TNF-α, TNF-β and G-CSF.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

and the transactivator (GAL4/VP16) are cloned into separate vectors. The expression of the transgene is then induced after co-infecting a target cell with the two vectors.

Figure 14:
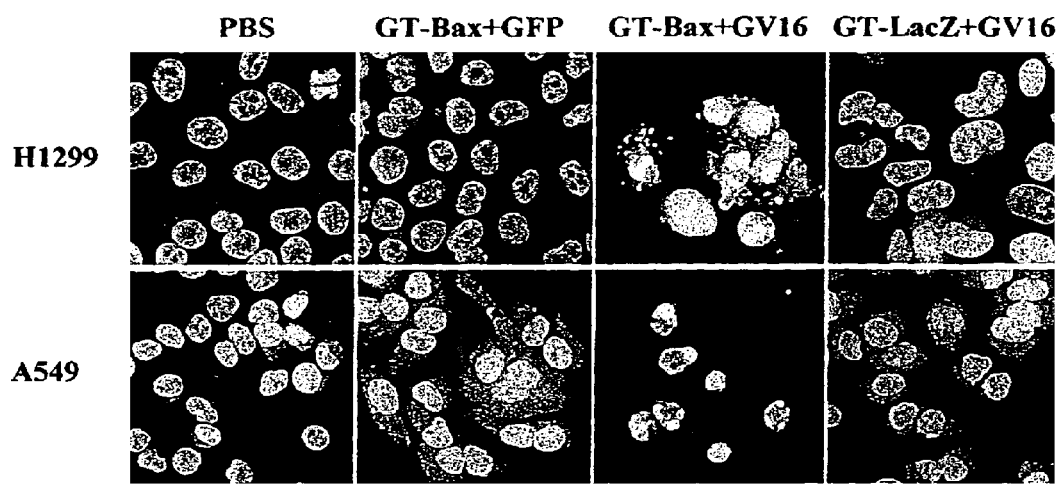
Figure 15A:
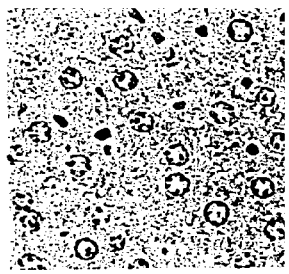
Figure 15B:
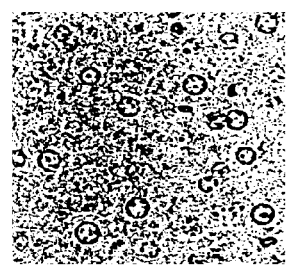
Figure 15C:
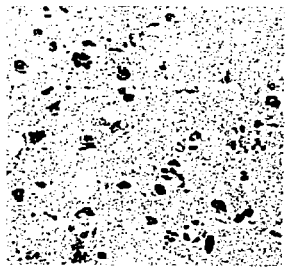
Figure 15D:
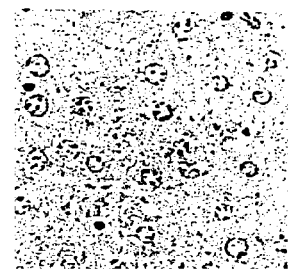

FIG. 14. Apoptosis profiles after induction of bax gene expression. Nuclear fragmentation detected by staining with Hoechst 33432. The treatment for each sample is indicated above each panel.

FIG. 15. In vivo induction of bax gene expression. Nuclear fragmentation detected by hematoxylin and eosin staining of liver sections from mice treated with (a) PBS, (b) Ad/GT–Bax+Ad/CMV-GFP, (c) Ad/GT-Bax+Ad/PGK–GV16, and (d) Ad/GT-LacZ+Ad/CMV–GV16.

DESCRIPTION OF ILLUSTRATIVE EMBODIMENTS

Cancer accounts the death of over half a million people each year in the United States alone. The causes for cancer are multifactorial, however, it is known that aberrations in controlled cell death result in uncontrolled cell proliferation and hence contribute to many cancer.

The p53 gene is well-recognized as possessing tumor suppressor capabilities and mutations in wild-type p53 are correlated to a variety of cancers. However, the interaction of p53 with other cellular factors is not well characterized, in fact, many of these factors remain undefined. It is not surprising that, in light of the lack of significant information on p53 function, there is an incomplete understanding of the pathways through which p53 regulates tumor development. Nevertheless, p53-based gene therapy has been remarkably effective in inducing cell cycle arrest and/or apoptosis in malignant cells carrying p53 gene mutations.

There now is a great deal of evidence that the apoptotic effect of p53 is mediated through the members of the proapoptotic Bcl-2 family. It has been shown that the p53 dependent expression of Bax is induced in slow-growing apoptotic tumors. Further, tumor growth appears accelerated, and apoptosis is decreased, in Bax-deficient mice. This suggests that Bax is required for a full p53-mediated response (Yin et al., 1997). The present invention, for the first time, provides evidence that proapoptotic Bcl-2 genes in adenoviral vectors can be used to decrease, diminish, inhibit or otherwise abrogate the growth of cancer cells.

The present invention employs, in one embodiment, an adenoviral expression construct comprising a gene that encodes a truncated Bax protein. As discussed herein below, the Bcl-2 family of proteins consists of death antagonists and death agonists, that regulate apoptosis and compete through dimerization. All members of the Bcl-2 family of proteins contain one or more Bcl-2 homology domains (BH). It appears that there are at least 4 BH domains, referred to as BH1, BH2, BH3 and BH4. The competition between the proapoptotic and antiapoptotic members is mediated at least in part, by competitive dimerization between selective pairs of antagonists and agonist molecules. Mutagenesis studies revealed that intact BH1 and BH2 domains of antagonists are required for repression of cell death. Conversely, the BH3 domain of Bax is the domain responsible for conferring the death agonist activity to Bcl proteins. Thus, in preferred embodiments, the present invention uses a truncated Bax protein having an intact "death domain." Of course other Bcl proteins such as Bak, Bid, Bik, that comprise the death domain will also be useful in the adenoviral constructs of the present invention.

In the present invention, the overexpression of the proapoptotic mediator Bax has been demonstrated in cancer cell lines transduced with an adenoviral Bax construct. Morphologically, apoptosis was seen within 4 days post-transduction. Thus, the present invention demonstrates that Bax induces apoptosis in cancer cell lines and provides evidence that adenoviral constructs containing Bax and/or other proapoptotic Bcl-2 gene family members will be useful components of a cancer therapy regimen. Methods of producing and using such compositions are discussed in further detail below.

In another embodiment, an adenoviral-mediated gene co-transfer system is described, that permits the regulated expression of cytotoxic gene products for use in treating hyperproliferative disease. In one embodiment, a first vector carrying a gene encoding a toxic product is under the control of a promoter, not active in the target source. A second vector, comprises a transactivator gene, wherein the transactivator protein product activates transcription from the promoter in the first expression vector. The choice of promoter on the second expression vector can be selected for use on an as needed basis (e.g., tissue specificity). It is contemplated further, that the co-transfer system can be used with any expression vector or combination thereof (e.g., viral, plasmid, plasmid shuttle vector, cosmid), introduced via any method of gene transfer desired (i.e., viral or non-viral) and used for both in vivo and in vitro.

A. The Bcl-2 Gene Family and Apoptosis

Apoptosis is an essential process required for normal embryonic development, maintenance of adult tissue homeostasis and the suppression of carcinogenesis. Apoptosis has been defined as a type of cell death which complements mitosis in the regulation of cell populations (Kerr et al., 1972). Apoptosis can occur as a result of both physiologic and pathologic conditions and is believed to be, in many developmental contexts, a programmed event. The sequence of events begins with nuclear and cytoplasmic condensation and ends with the release and phagocytosis of apoptotic bodies (Kerr et al., 1972).

A major advance in understanding the regulation of apoptosis came with the discovery of the Bcl-2 proto-oncogene from the t(14;18) chromosomal translocation breakpoint in follicular lymphoma (Bakhshi et al., 1985; Cleary and Sklar, 1985; Cleary et al., 1986; Tsujimoto et al., 1985; Tsujimoto and Croce, 1986). Bcl-2 acts to suppress cell death triggered by a variety of stimuli and, it is now apparent that there is a family of Bcl-2 cell death regulatory proteins which share in common structural and sequence homologies. These different family members have been shown to either possess similar functions to Bcl-2 or counteract Bcl-2 function and promote cell death. These cell death regulators are discussed in further detail herein below.

In mammalian development, Bcl-2 and Bcl-2 family members have been shown to play a role in morphogenesis and normal development. During murine fetal development Bcl-2 is expressed in tissues derived from all three germ layers; however, as the fetus matures, Bcl-2 expression becomes restricted (Novack and Korsmeyer, 1994). Similar observations were seen in human fetal tissues in that Bcl-2 was expressed in a wide variety of tissue types and expression became restricted as the fetus matured (LeBrun et al., 1993; Chandler et al, 1994). Bcl-2 was detected in the human fetal thymus, hematopoietic cells, endocrine glands, and hormonally regulated tissues and differential expression of Bcl-2 family members occurs during neuronal differentiation. Bcl-$x_L$ and Bcl-2 are both expressed in neurons of the developing human fetus, however, Bcl-$x_L$ expression persists throughout fetal development and into adulthood whereas Bcl-2 expression diminishes between wk 20–39 of gestation (Yachnis et al., 1997).

Although Bcl-2 protein is widely expressed in embryonic tissues (Novack and Korsmeyer, 1994; Lu et al., 1993), absence of Bcl-2 protein in Bcl-2 null mice does not interfere with normal prenatal development (Veis et al., 1993). However, postnatally, these mice display growth retardation, smaller ears, and polycystic kidneys, and most die within several months due to kidney failure. In the Bcl-2 deficient mice, which eventually become ill, the thymus and spleen are atrophic due to massive lymphocyte apoptosis. Also, Bcl-2 null thymocytes are more susceptible to undergo apoptosis following γ-irradiation or treatment with dexamethasone (Kamada et al, 1995; Nakayama et al., 1994).

The tissue distribution of Bcl-2 expression also suggests that Bcl-2 plays a role in survival in various cell types (Hockenbery et al, 1991). Immunohistochemistry reveals that Bcl-2 is expressed in cells that regenerate such as the stem cells or in cells that are long lived. In the lymphatic system, Bcl-2 is strongly expressed in the thymic medulla where the T-cells which have survived negative and positive selection reside, and in the areas of lymph nodes associated with maintenance of plasma cells and memory B-cells (Hockenbery et al., 1991; Nunez et al., 1991). In non-hematopoietic tissues, Bcl-2 is restricted to cells that undergo self renewal such as the basal layer of the skin, the crypt cells of the small and large intestine, and in long lived cells such as the neurons. Bcl-2 also is expressed in tissues such as breast duct epithelium and prostate epithelium which undergo hyperproliferation or involution at the influence of the hormone or growth factors (Hockenbery et al., 1991; McDonnell et al., 1992).

The Bcl-2 family continues to expand with the discovery of new members. Table 1 summarizes the Bcl-2 family of cell death regulators.

It is commonly accepted that tumorigenesis is a multistep process which may involve chromosomal abnormalities and the deregulated expression of proto-oncogenes (Bishop, 1991). This is particularly evident in hematolymphoid neoplasms where chromosomal translocations may result in the activation of a proto-oncogene. Translocations involve the breakage and reunion of chromosomes where part of one chromosome breaks off and becomes reattached to another chromosome. Such translocations are described by a notation that indicates which two chromosomes have been recombined. For example, t(9:22) indicates that a translocation has occurred between chromosome 9 and chromosome 22. Further delineation of the exact regions or genes that are involved in the translocation lead to the identification of the resulting gene fusions or proto-oncogenes involved in each particular translocation event. Certain chromosomal translocations are associated with activation of oncogenes that lie near the breakpoint of the chromosome.

Characterization of the t(9;22) and t(8;14) translocations in chronic myelogenous leukemia (Nowell and Hungerford, 1960; Rowley, 1973) and Burkitt's lymphoma (Manalov and Manolova 1972; Zech et al., 1976), respectively, provided a paradigm for the deregulation of proto-oncogenes during multistep carcinogenesis.

B. Bcl-2 Family Members

Figure 1A:
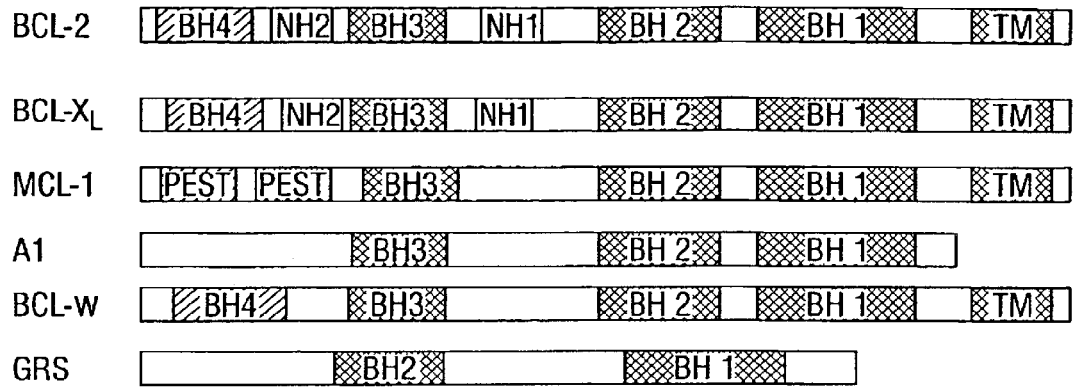
FIG. 1 Schematic depiction of the protein structures of the Bcl-2 family members. BH1, BH2, BH3, and BH4 are the conserved homology domains. TIM indicates the transmembrane domain, NH2 indicated the amino terminal domain, and the PEST domain represents the region which is correlated to an early response gene product and is associated with rapid protein turnover. GRS is grouped with the anti-apoptotic family members, however, its role in apoptosis is not currently known.
Figure 1B:
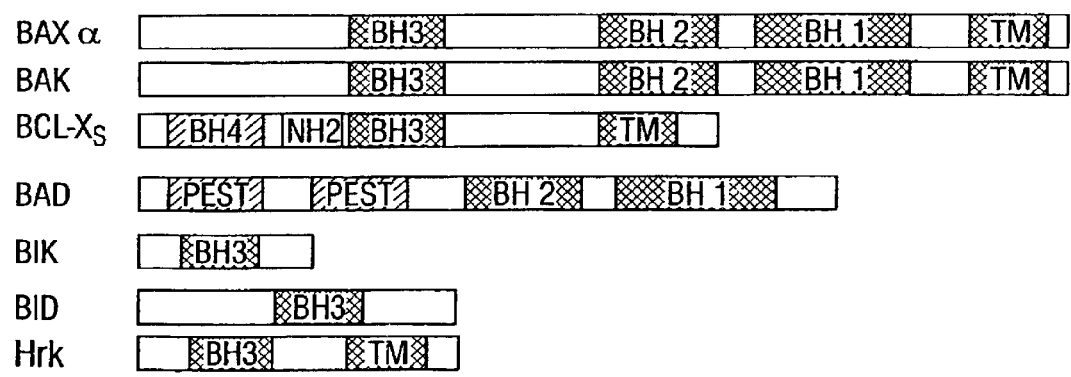

Many Bcl-2 family member proteins have now been identified (FIG. 1). These Bcl-2 homologues can be broadly categorized as death antagonists and death agonists. The growing list of Bcl-2 gene family members all share highly conserved domains referred to as Bcl-2 homology domain 1 and 2 (BH1 and BH2) (Oltvai et al., 1993; Yin et al., 1994; Yin et al., 1995) or domains B and C, respectively (Hanada et al., 1995; Tanaka et al., 1993). These homology domains seem to be important for Bcl-2 to form heterodimeric complexes with the family members and to carry out its anti-apoptotic function (Yin et al., 1994; Hanada et al., 1995;

TABLE 1

Human Bcl-2 Family Members

| Family Member | Gene Size (Kb) | mRNA Size (Kb) | Amino Acid Residues | Protein Size (kD) | Chromosome Localization | Function | Genebank Sequence Identifiers |
|---|---|---|---|---|---|---|---|
| Bcl-2 | 230 | 6.5 | 239 | 25 | 18q21 | Anti-Apoptotic | M14745 |
| Bcl-x$_L$ | ND | 2.7 | 233 | 31 | ND | Anti-Apoptotic | |
| Bcl-w | 22 | 3.7 | 193 | 22 | ND | Anti-Apoptotic | |
| Mcl-1 | ND | 3.8 | 350 | 37.3 | 1q21 | Anti-Apoptotic | |
| A1 | ND | 1.4* | 172 | 20** | ND | Anti-Apoptotic | |
| Bfl-1 | ND | 0.6* | 175 | 20*** | ND | Anti-Apoptotic | |
| Bax α | 4.5 | 1.0 | 192 | 21 | 19q13.3–13.4 | Pro-Apoptotic | L22473 |
| Bax β | | 1.5 | 218 | 24 | | ND | L22474 |
| Bax γ | | | 41**** | 4.5** | | ND | L22475 |
| Bax δ | | 1.5 | 143**** | ? | | ND | U19599 |
| | | ND | | | | | |
| Bcl-x$_S$ | ND | 1.0 | 170 | 19 | ND | Pro-Apoptotic | Z23116; L20122 |
| Bak 1 | 6 | 2.4 | 211 | 23 | 6 | Pro-Apoptotic | U16811; U23765 |
| Bak 2 | | | | | 20 | | U16812; U23765 |
| Bak 3 | | | | | 11 | | |
| Bad | ND | 1.1* | 204 | 22 | ND | Pro-Apoptotic | AF031523 |
| Bid | ND | 1.1* | 195 | 23 | ND | Pro-Apoptotic | U75506 |
| Bik | ND | 1.0 | 160 | 18 | ND | Pro-Apoptotic | U34584 |
| GRS | ND | 0.8 | 175 | ? | 15q24–25 | ND | |
| Harakiri | ND | 0.7 | 91 | 16***** | ND | Pro-Apoptotic | U76376 |

ND, not determined.
*cDNA;
**predicted size of protein;
***size of Ha-Tagged protein;
****predicted amino acid length;
*****size of the Flagged protein.
The known Genbank sequences are listed and are specifically incorporated herein by reference in order to provide additional disclosure of the sequences of the genes of the Bcl family.

Yang et al., 1995a; Korsmeyer et al., 1993; Sedlak et al., 1995). For example, mutations in BH1 and BH2 prevent Bcl-2 from forming heterodimeric complexes with the Bcl-2 homologue Bax and can abrogate the survival function of Bcl-2 (Yin et al., 1994). The Bcl-2 protein can also form homodimers with itself via its NH2 terminal region called the BH4 domain which spans residues 11 through 33 (Hanada et al., 1995).

Thus, as stated earlier, the Bcl-2 family members are divided into proapoptotic and antiapoptotic genes. The proapoptotic genes include Bax, Bak, Bcl-$x_S$, Bad, Bik, Bid and Harakiri. The antiapoptotic genes include Bcl-2, Bcl-$x_L$, Mcl-1, A1, Bcl-w and GRS (FIG. 1). Each of these genes are discussed in further detail herein below.

i. Bcl-2

The t(9;22) results in the formation of a bcr-abl fusion gene and chimeric protein (Shrivelman et al., 1985) while the t(8;14) results in the inappropriate expression of c-myc (Dalla-Favera et al., 1982; Taub et al., 1984; Nishikura et al., 1983). Both of these molecular events result in augmented cellular proliferation (Langdon et al., 1986).

Bcl-2 was discovered as a novel transcriptional element by its association with the t(14;18) reciprocal chromosomal translocation commonly found in follicular lymphoma (Bakhshi et al., 1985; Cleary and Sklar, 1985, Tsujimoto et al., 1984). Bcl-2 was shown to be a unique oncogene in that its deregulation did not result in an increase in cell proliferation, but rather enhancement of cell survival (Vaux et al., 1988; Hockenbery et al., 1990; McDonnell et al., 1989). Thus, Bcl-2 represents a class of oncogene that enables neoplastic growth by suppressing cell death (McDonnell, 1993a).

The Bcl-2 gene, is comprised of three exons and spans approximately 230 Kb. The open reading frame is in exon 2 and 3, and encodes a 25 kD integral membrane protein (Seto et al., 1988; Zutter, et al., 1991). The message can be alternatively spliced to give two transcripts, Bcl-2α and the truncated Bcl-2β that lacks the C-terminus region (Tsujimoto and Croce, 1986). Bcl-2 possesses a very hydrophobic stretch of 23 amino acids at the C-terminus which serve as a transmembrane domain (Hockenbery et al., 1990). Bcl-2 protein localizes to the nucleus, rough ER, and mitochondria. In mitochondria, the protein is localized to the contact zone of the inner and outer membranes of the mitochondrial membrane where the transport of materials from the cytosol into the mitochondrial matrix occurs (Hockenbery et al., 1990; deJong et al., 1992).

Bcl-2 is normally expressed in pro and mature B-cells, but is downregulated in pre and immature B lymphocytes (Merino et al., 1994). This differential expression points to the survival role of Bcl-2 in B lymphocyte development. High levels of Bcl-2 are needed to ensure the survival of pro-B-cells and mature B-cells in order to maintain a population of functional lymphocytes. But low levels of Bcl-2 are necessary for cells, which do not express functional surface Ig or are self reactive, to undergo apoptosis. Also in T-cells, Bcl-2 is expressed at low levels in double positive thymocytes undergoing negative and positive selection, and at high levels in mature single positive T-cells which have survived the selection (Gratiot-Deans et al., 1993). Thus, Bcl-2 seems to have an important role in lymphocyte development (McDonnell et al., 1989; McDonnell et al., 1990; McDonnell and Korsmeyer, 1991;).

The Bcl-2-Ig transgenic mouse model demonstrates that deregulation of Bcl-2 gene causes initially a polyclonal expansion of mature B-cells which can progress to an aggressive monoclonal malignancy with an acquisition of additional gene deregulation, thus confirming the multistep nature of carcinogenesis (McDonnell, 1993b). In humans also, follicular lymphoma can progress to a high grade lymphoma following the acquisition of t(8; 14) translocations and c-myc gene deregulation, albeit this appears to be an uncommon event (Gawerky et al., 1988).

It also has been demonstrated that Bcl-2 plays a role in the suppression of p53-mediated cell death. Splenic mononuclear cells obtained from Bcl-2-Ig mice, which possess wild-type p53, displayed rates of apoptosis comparable to cells obtained from p53 knockout mice following γ-irradiation (Marin et al., 1994). Together, these results and the results of others utilizing transformed cell lines indicate that Bcl-2 is capable of blocking p53 mediated cell death induction (Marin et al., 1994; Wang et al., 1993; Chiou et al., 1994).

Mutations in the conserved domains of p53 were uncommon in the lymphomas arising in the Bcl-2-Ig transgenic mice suggesting that there is no selective advantage of acquiring p53 mutations when Bcl-2 is overexpressed (Marin et al., 1994). Additionally, the Bcl-2-Ig transgenic and p53 knockout murine models were further utilized to determine the extent of genetic complementation between p53 and Bcl-2. In p53 KO/Bcl-2 hybrid mice, tumor latency and incidence were unchanged when compared to individual parental strains of mice (Marin et al., 1994). Many human tumors, such as breast and prostate, also demonstrate that there is an inverse correlation between the presence of p53 mutations and Bcl-2 expression (Silvstrini et al., 1994; McDonnell et al., 1997).

ii. Bax

Bax (SEQ ID NO:3=cDNA; SEQ ID NO:4=wild-type protein), "Bcl-2 associated X protein", is a death agonist member of the Bcl-2 family of proteins. Discovered by co-immunoprecipitation with Bcl-2, it was the first Bcl-2 homologue to be identified (Oltvai et al., 1993). The 4.5 Kb Bax gene maps to 19q13.3–13.4 and is comprised of six exons (Apte et al., 1995). It shares 21% identity and 43% similarity with Bcl-2. The most conserved regions between the two molecules are within the BH1 and BH2 domains encoded by exons 4 and 5, respectively (Oltvai et al., 1993).

Multiple forms of Bax protein can result from various splicing alternatives. The most prevalent from is Bax-α, whose 1.0 Kb RNA encodes a 192 amino acid, 21 kD transmembrane protein. The 24 kD cytosolic Bax-P lacks the transmembrane segment and is encoded by 1.5 Kb RNA transcript. A third form, Bax-γ lacks the exon 2 and can undergo alternative splicing of intron 5 to yield 1.0 and 1.5 Kb RNA transcripts (Olsen et al., 1996). Yet another alternatively spliced form of Bax, Baxδ, has the C-terminal transmembrane anchor as well as the BH1 and BH2 domains (Apte et al., 1995). The functional role of these Bax variants remains to be elucidated.

The Bax gene promoter contains four p53 binding sites and the expression of Bax is upregulated at the transcriptional level by p53 (Miyashita and Reed, 1995). A temperature sensitive p53 mutant transfected into a myeloid cell line was associated with increased Bax mRNA after shifting to the permissive temperature (Zhan et al., 1994). Also in cells obtained from p53-null mice, the level of Bax proteins was found to be lower (Miyashita et al., 1994). Moreover, following apoptosis induction by ionizing radiation, the Bax mRNA was upregulated only in the cell line that possesses wild-type p53 (Zhan et al., 1994). These data suggest that Bax may function as a primary response gene in a p53 regulated apoptotic pathway (Miyashita et al., 1994). However, thymocytes from the Bax knockout mice were not diminished in their capacity to undergo apoptosis after γ-irradiation, a pathway driven by p53 (Knudson et al., 1995). Bax expression can also be modulated by other factors. The mRNA level has been shown to be downregulated in myeloid leukemia cell lines treated with IL-6 and/or dexamethasone (Lotem and Sachs, 1995). The half life of Bax mRNA can be increased in cell lines expressing higher levels of Bcl-2 (Miyashita et al., 1995). However, this increase in stability of Bax mRNA by Bcl-2 protein appears to be tissue specific.

Mutational analysis has shown that the BH1 and BH2 domains of Bax are not required for heterodimerization with Bcl-2, nor is the $NH_2$ terminal amino acids needed for Bax homodimerization, unlike the homodimerization requirement for Bcl-2. Rather a stretch of amino acids spanning residues 59–101 in the BH3 domain was shown to be essential in both the homodimerization and heterodimer complex formation with Bcl-2 (Zha et al., 1996a). Additionally, in contrast to Bcl-2, Bax can function in its monomeric form to accelerate cell death (Simonian et al., 1996). Bax can heterodimerize with other Bcl-2 related proteins, including Bcl-$X_L$, Mcl-1, and A1 (Sedlak et al., 1995). The "rheostat" model has been proposed to explain the role of Bcl-2 family member interactions in controlling cell death. This model suggests that the relative amounts of Bcl-2 and Bax may determine the susceptibility of a cell to undergo apoptosis (Korsmeyer et al., 1993). According to this model, when Bcl-2 is in excess, Bcl-2/Bax heterodimers predominate and cell death is inhibited. Conversely, when Bax is in excess, Bax homodimers predominate and the cell becomes susceptible to cell death induction following exposure to an apoptotic stimulus.

The tissue distribution of Bax protein is more widespread than Bcl-2. (Krajewski et al., 1994a). The immunohistochemical staining of murine tissues has revealed that the expression of Bcl-2 and Bax overlap in some tissues, and that Bax is not always expressed at high levels in compartments marked by a high turnover rate. For example, Bax, as well as Bcl-2, are expressed in the thymic medulla but not in the thymic cortex, despite high numbers of cortical thymocytes which undergo apoptosis. Also, a high level of Bax protein is observed in neurons, cells that have a long life. However, in certain tissues such as colonic epithelium, gastric glands, and secretory epithelial cells of prostate, Bax expression corresponds to the cells that are susceptible to undergoing apoptotic cell death (Krajewski et al., 1994a).

Evidence that apoptosis is not absolutely dependent on the expression of Bax is also apparent from an analysis of the Bax knockout mice. In these mice the absence of Bax is associated with either tissue specific hyperplasia or hypoplasia (Knudson et al., 1995). For example, there was an increase in number of resting mature B-cells and thymocytes causing hyperplasia in the spleen and thymus. However, the male Bax knockout mice were infertile due to atrophic testes, resulting from the abrogation of spermatogenesis (Knudson et al., 1995).

Recent evidence suggests that Bax may play a role as a tumor suppressor. Normally Bax-α is expressed at high levels in breast tissue but is not detectable, or expressed at low levels, in breast cancers (Bargou et al., 1995). Furthermore, in metastatic breast cancer, patients with reduced Bax expression showed poor response to chemotherapy (Krajewski et al., 1995a). Transgenic mice have been generated, which express a truncated form of the SV40 T antigen (Tg121) resulting in inactivation of the retinoblastoma protein but not p53. Tg121 mice bearing targeted disruptions of either the p53 gene or the Bax gene exhibited an increased rate of brain tumor formation compared to Tg121 mice with intact p53 or Bax genes (Yin et al., 1997). Also frequent frame shift mutations of Bax were found in microsatellite mutator phenotype (MMP) colon adenocarcinomas, suggesting that the wild-type Bax gene may play a tumor suppressor role in colorectal carcinogenesis (Rampino et al., 1997).

iii. Bcl-x

Bcl-x was initially isolated from chicken lymphoid cells using a murine Bcl-2 cDNA probe under low stringency conditions (Boise et al., 1993). The Bcl-x gene shares 44% identity with Bcl-2. Bcl-x was shown to interact with other members of the Bcl-2 family in a manner similar to that shown for Bcl-2 when analyzed by the yeast two-hybrid system (Sato et al., 1994). Two human Bcl-x cDNAs have been cloned (Boise et al., 1993). Bcl-$x_L$ (long form) is a 31 kD protein, with an open reading frame of 233 amino acid. This form of Bcl-x contains the BH 1 and BH2 domains. The BCl-$x_L$ cDNA was found to be co-linear with the genomic sequence denoting the absence of mRNA splicing. Bcl-$x_S$ (short form) encodes a 170 amino acid, 19 kD protein. The carboxy-terminal 63 amino acids encoding the BH1 and BH2 domains are deleted from a 5' splice site within exon 1 of the Bcl-x gene (Boise et al., 1993). A third alternative splice variant of Bcl-x has been isolated from a murine cDNA library, Bcl-$x_β$, (Gonzalez-Garcia et al., 1994). Bcl-$x_β$, encodes a 209 amino acid protein that results from an unspliced first coding exon and lacks the carboxy-terminal 19 hydrophobic amino acids necessary for transmembrane insertion.

Both the level and pattern of expression of Bcl-x differ from that of Bcl-2. The levels of Bcl-x expression are generally higher than Bcl-2 in all tissues examined except for the lymph nodes where Bcl-2 is predominant (Krajewski et al., 1994a). Bcl-$x_L$ is mainly expressed in the cells of the central nervous system, kidney, and bone marrow (Gonzalez-Garcia et al., 1994,; Rouayrenc et al., 1995). Both Bcl-$X_L$ and Bcl-$x_S$, but not Bcl-2 are expressed in $CD34^+$, $CD38^-$, $lin^-$ hematopoietic precursors (Park et al., 1995). However, the subcellular distribution of Bcl-x protein is similar to Bcl-2 in that it localizes to mitochondria and the nuclear envelope. This suggests that the function of the two proteins may be similar (alez-Garcia et al., 1994,).

Further insight into the role of Bcl-x during development was obtained from Bcl-x deficient mice (Motoyama et al, 1995). Heterozygous mice developed normally while homozygous, knockout mutants die at approximately day 13 of gestation. The Bcl-x knockout embryos display extensive apoptosis involving post-mitotic neurons of the developing brain, spinal cord, dorsal root ganglia, and hematopoietic cells in the liver. Additionally, lymphocytes from Bcl-x deficient mice showed diminished maturation. The life span of immature lymphocytes but not mature lymphocytes was shortened. This data indicates that Bcl-x is required for the embryonic development of the nervous and hematopoietic systems.

Similar to Bcl-2, Bcl-$x_L$ was shown to confer resistance to apoptosis induction following growth factor deprivation. However, Bcl-$x_S$ counteracted the ability of Bcl-2 to block apoptosis (Boise et al., 1993). Although Bcl-$X_L$, and Bcl-2 initially seemed to have the same functions, several observations suggest that biologically these two proteins are not completely overlapping. The tissue distribution of Bcl-2 and Bcl-x are not identical and the phenotypes' of the corresponding knockout strains of mice are substantially different. Furthermore, it has been shown that WEHI-231 cells can be protected from apoptosis induced by surface IgM cross-linking by enforced Bcl-$x_L$ expression while enforced Bcl-2 expression exerts no such protective effect (Choi and Boise, 1995; Gottschalk et al., 1994).

The crystalline structure of Bcl-x has expanded the inventors' insight into the potential mechanisms of function of Bcl-2 family members (Muchmore et al., 1996). Bcl-x structure was shown to consist of two central hydrophobic a helices surrounded by two amphipathic helices (Muchmore et al., 1996). Interestingly, the conserved BH1, BH2 and BH3 domains were in spatial proximity and formed a hydrophobic cleft. This cleft is believed to, form a binding site for other Bcl-2 family members (Muchmore et al., 1996). Evidence in favor of this hypothesis was provided when Bcl-x and a 16 residue bak peptide derived from the BH3 domain were co-crystallized. The heterodimeric crystal structure revealed that the bak BH3 domain interacts with the hydrophobic cleft made by the BH1, BH2, and BH3 domains of Bcl-x (Sattler et al., 1997). The crystal structure of Bcl-x was also found to resemble the translocation domain of the diphtheria toxin and colicins (Muchmore et al., 1996). This similarity in structure implies similarity in function and indicates that Bcl-2 family members can be considered channel forming proteins capable of regulating the transmembrane trafficking of molecules involved in signaling cell death.

iv. Bak

Bak (Bcl-2-homologous antagonist/killer) was first cloned from human heart and Epstein-Barr transformed human B-cell cDNA libraries (Chittenden et al., 1995; Kiefer et al., 1995; Farrow et al., 1995). There are three closely related bak genes (bak-1, 2, and 3) which are located on chromosome 6 (bak-1), chromosome 20 (bak-2) and chromosome 11 (bak-3). The bak genes contain at least three exons and span 6 Kb. Bak is a 211 amino-acid, 23 kD protein which shares 53% amino-acid identity with Bcl-2. It possesses the same hydrophobic carboxy-terminal domain as Bcl-2 and Bcl-x L, which suggests that bak is an integral membrane protein. In contrast to Bcl-2, bak is expressed at high levels in the kidney, pancreas, liver, and fetal heart, as well as adult brain (Kiefer et al., 1995). Similar to Bax in the intestine, bak expression is strongest in the cells in the luminal surface where most apoptosis is occurring. However, in a colorectal carcinoma cell line, only bak expression was shown to be modulated following apoptosis induction, indicating that bak may play a primary role in enterocyte apoptosis (Moss et al., 1996). This contention is further supported by the observation that bak expression is reduced in colorectal adenocarcinoma samples. Therefore, a downregulation of bak may facilitate the accumulation of neoplastic cells in the early stages of colorectal tumorigenesis (Krajewski et al., 1996). Bak was shown, to accelerate cell death following IL-3 withdrawal (Chittenden et al., 1995; Kiefer et al., 1995), but inhibits apoptosis induced by serum withdrawal and menadione treatment (Chittenden et al., 1995).

v. Bad

Bad (Bcl-$x_L$/Bcl-2 associated death promoter homologue) a novel member of the Bcl-2 family that was identified as a Bcl-2 interacting protein using the yeast two hybrid system (Yang et al, 1995b). The full-length Bad cDNA sequence encodes a novel 204 amino acid protein with a predicted molecular weight of 22 kD. Bad shares only limited homology with known Bcl-2 family members in the BH1 and BH2 domains. However, the functionally significant W/YGR triplet in BH1, the W at position 183, the WD/E at the exon junction in BH2 and the spacing between BH1 and BH2 domains is conserved. Unlike many other Bcl-2 family members, Bad does not contain a transmembrane anchor domain.

Bad was shown to heterodimerize with Bcl-2 and Bcl-x in vivo using co-immunoprecepitation. Bad's interaction with either Bcl-2 or Bcl-x can displace Bax from the heterodimers. Significantly, this was shown to reverse the death repressor activity of Bcl-x, but not of Bcl-2. However, Bad does not appear to interact with Bax, Mcl-1, or A1 nor, apparently, does Bad form homodimers (Yang et al, 1995b). Recent studies have shown that Bad may function in intracellular signal transduction pathways. Upon IL-3 stimulation of an IL-3 dependent hematopoietic cell line, Bad becomes rapidly phosphorylated at two serine residues and is prevented from forming heterodimeric complexes with Bcl-$x_L$. The phosphorylated Bad is found to be complexed with 14-3-3, a phosphoserine binding protein which regulates protein kinases, and is sequestered in cytosol (Zha et al, 1996b). Therefore, only the non-phosphorylated Bad is heterodimerized with the membrane bound Bcl-$x_L$ and counters the anti-apoptotic activity of Bcl-$x_L$. One of the models to explain the apoptotic activity of Bad is that in its non-phosphorylated form, Bad binds to membrane associated Bcl-XL which releases Bax to enhance cell death (Zha et al., 1996b). Another link between the phosphorylation event and the apoptotic pathway was shown when it was found that in vitro, Bad is phosphorylated by mitochondrial membrane targeted Raf-1, but not by the plasma membrane targeted Raf-1. Moreover, Bcl-2 was shown to target Raf-1 to mitochondrial membrane which resulted in phosphorylation of Bad and the subsequent enhancement of cell survival (Wang et al., 1996a).

vi. Mcl-1

Mcl-1 (human myeloid cell differentiation protein)was identified by differentially screening cDNA library of the human myeloid leukemia cell line, ML-1, following induction by phorbol 12-myristate 13-acetate (TPA) (Kozopas et al., 1993). Mcl-1 has also been detected in normal peripheral blood B cells after treatment with IL4 and anti-IgM. Mcl-1 is an early response gene, that reduces its expression immediately following differentiation induction (Kozopas et al, 1993; Yang et al., 1995). A study done using a yeast two-hybrid assay indicates that Mcl-1 interacts strongly and selectively with Bax, but not with any other Bcl-2 family members (Sedlak et al., 1995; Sato et al., 1994).

Mcl-1 shares sequence homology to Bcl-2 in the BH1 and BH2 domains and has a carboxy-terminal transmembrane anchor domain (Yang et al., 1995). In addition, the Mcl-1 protein possesses PEST sequences (Kozopas et al., 1993), which correlate with the its role as an early response gene product (Yang et al., 1995). The human Mcl-1 gene maps to chromosome 1 band q21 (Craig et al., 1994), an area often involved in chromosomal abnormalities in neoplastic and preneoplastic diseases (Atkin, 1986; Gendler et al., 1990; Testa, 1990).

Mcl-1 protects against apoptosis induced by constitutive expression of c-myc or Bax (Reynolds et al., 107). However, in the 5AHSmyc cell line, Mcl-1 overexpression is not as effective as Bcl-2 overexpression in preventing myc-mediated cell death (Reynolds et al., 1994). It has been proposed that Mcl-1 may function as an alternative to Bcl-2 in situations where Bcl-2 cannot block apoptosis or in tissues lacking Bcl-2 expression. For example, in normal peripheral blood B cells treated with agents which promote survival (IL-4, anti-$\mu$, and TPA) or enhance rates of cell death (TGF$\beta$1 and forskolin), upregulation of Mcl-1 correlates with cell survival and downregulation of Mcl-1 precedes cell death. In contrast, levels of Bcl-2 expression are not modulated under the same experimental conditions (Lomo et al., 1996).

Additionally, the tissue distribution of Mcl-1 and Bcl-2 expression show significant differences such as brain and spinal cord neurons in which Bcl-2 predominates compared to skeletal muscle, cardiac muscle, cartilage and liver where Mcl-1 predominates over Bcl-2 (Krajewski et al., 1995b). Similarly, Mcl-1 levels in normal lymph nodes are highest in germinal centers, where the rate of apoptosis is high. In contrast, Bcl-2 is most intense in the mantle zone. It has been postulated that Mcl-1 temporarily blocks cell death until suppression such as Bcl-2 are upregulated (Krajewski et al., 1994b).

vii. A1

A1 was identified by differentially screening a cDNA library of normal peripheral blood B cells and after treatment with IL-4 and anti-IgM. The A1 cDNA was isolated from murine macrophages after GM-CSF induction of differentiation (Lin et al., 1993). A1 is an early response gene that decreases its level of expression immediately following differentiation induction (Lin et al., 1993). Yeast two-hybrid assay indicates that A1 interacts strongly and selectively with Bax, with but not with any other Bcl-2 family member (Sedlak et al., 1995; Sato et al., 1994). A1 shares homology with Bcl-2 in the BH1 and BH2 domains, but does not possess the carboxy-terminal transmembrane domain (Lin et al., 1993).

The correlation of GM-CSF and LPS-induced differentiation with A1 upregulation suggest A1 could potentially function as a cell death suppressor (Lin et al., 1993). Later reports has shown that A1 protects against TNF induced apoptosis in the presence of actinomycin D in a human microvascular endothelial cells (Karsan et al., 1996). A1 could also inhibit ceramide induced cell death in these endothelia cells (Karsan et al., 1996). A1 expression displays a rather limited tissue distribution and appears to be confined to hematopoietic tissues, including helper T-cells, macrophages, and neutrophils (Lin et al., 1993).

viii. Bfl-1I

Bfl-1 (Bcl-2 related gene expressed in human fetal liver) was identified during a random cDNA sequencing project (Choi et al., 1995). It was found to be homologous to Bcl-2 family members with the highest homology to the A1 gene. The main region of homology was in the conserved BH1, BH2, and BH3 domains. Bfl-1 is mainly expressed in bone marrow while low levels of expression are detected in lung, spleen, esophagus, and liver. Bfl-1 mRNA was detected at relatively high levels in six out of eight stomach cancer tumors and metastasis when compared to normal stomach tissue from the same patients (Choi et al., 1995). Bfl-1 protein suppresses apoptosis induced by p53 in the BRK cell line to the same extent Bcl-2, Bcl-$x_L$. Bfl-1 was also shown to cooperate with E1a in the transformation of primary rodent epithelial cells (D'Sa-Eipper et al., 1996).

ix. GRS

GRS was incidentally cloned during the cloning of fibroblast growth factor 4 (FGF-4) from a patient with chronic myelogenous leukemia (Lucas et al., 1994). The FGF-4 gene was truncated by a DNA rearrangement with a novel gene named GRS (Glasgow Rearranged Sequence) with a breakpoint 30 nucleotides downstream from the translation termination codon of FGF-4. The full length cDNA of GRS was then cloned from human activated T cell cDNA library. The GRS cDNA is 824 nucleotides (Kenny et al., 1997). Sequence analysis of GRS revealed 71% identity to the murine A1 protein at the amino acid level.

Northern blot analysis showed a high level of expression of GRS in hematopoietic cells and to a lesser extent in lung and kidney (Kenny et al., 1997). GRS also is expressed in cell lines of hematopoietic origin including HL-60 (promyelocytic leukemia), Raji (Burkitt lymphoma) and K-562 (chronic myeloid leukemia). However GRS is not expressed in MOLT-4 T lymphoblastic leukemia and T-cells prior to activation. The melanoma cell line G-361 also expressed high levels of GRS. GRS is localized to chromosome 15q24-25. This location positions GRS adjacent to t(15;17) region translocation frequently observed in acute promyelocytic leukemia. The GRS location also places it in the breakpoint described in Fanconi anemia that is associated with high incidence of acute leukemia.

x. Bid

Bid (BH3 interacting domain death agonist) was initially identified as a protein that interacts with both Bcl-2 and Bax proteins. The labeled Bax and Bcl-2 proteins were used to screen a λEXlox expression library constructed from the murine T-cell hybridoma line 2B4 (Wang et al, 1996c). Bid is a 23 kD, 195 amino acid protein. Sequence analysis of Bid revealed that Bid shares homology only with the BH3 domain of the Bcl-2 family and that it lacks the carboxy-terminus transmembrane hydrophobic domain. A human homologue of Bid has also been identified. Human Bid shares 72.3% sequence homology to the murine Bid and has a 195 amino acid open reading frame (Wang et al., 1996c).

In adult mouse tissue, Bid is mainly expressed in the kidneys but is also present in brain, spleen, liver, testis and lung (Wang et al., 1996c). Low levels of expression are detected in the heart and skeletal muscle. The mouse hematopoietic cell line, FL5.12, was also found to express high levels of Bid. Subcellular fractionation has revealed that Bid is predominantly localized to the cytosol (90%) with a small fraction in the membrane fraction (Wang et al., 1996c).

Expression of Bid in the IL-3 dependent FL5.12 cell line could induce a subtle but consistent enhancement of apoptosis following IL-3 withdrawal (Wang et al, 1996c). Bid inducible expression as well as transient transfections of Bid in Rat-1 fibroblasts and Jurkat T-cells, results in reducing cell viability to <40% at 48 h (Wang et al., 1996c). Bid could also restore apoptosis in FL5.12 clones overexpressing Bcl-2. The level of apoptosis was intermediate between the parental and Bcl-2 overexpressing clones. The degree of cell death in all cases corresponded to the level of Bid protein expression as detected by Western blot analysis. Bid induced apoptosis could be inhibited by zVAD-fmk, an irreversible inhibitor particularly effective against the CPP32-like subset of proteases. This suggests that Bid induced cell death involves activation of CPP32-like proteases (Wang et al., 1996c).

Bid interacts with both death agonists and antagonists members of the Bcl-2 family. Bid can interact with. Bcl-2, Bcl-x, and Bax but does not form homodimers. Bid was unable to form trimolecular complexes with Bcl-2/Bax heterodimers suggesting that Bid interacts with monomeric or homodimeric Bcl-2 or Bax. Several mutants of Bcl-2, Bax, and Bid were examined to detect the regions of each molecule required for their interactions. The BH3 domain of Bid was essential for interaction with Bax and Bcl-2. Differential specificity of these mutants was also detected as mutant (M97A, D98A) could bind Bax but not Bcl-2, mutant (G97A) could bind Bcl-2 but not Bax while other mutants did not bind either protein. Noteworthy is that all BH3 mutants of Bid were impaired in their ability to counter Bcl-2 protection including mutants that could still bind Bcl-2. However, Bid mutant (M97A, D98A) that can still bind Bax but not Bcl-2, retained its activity. Conversely, the BH 1 domain of Bcl-2 and Bax were shown to be required for their interaction with Bid. It is suggested that the α helix BH3 domain of Bid interacts with the hydrophobic cleft contributed by the BH1 domain of Bcl-x. This interaction might result in a conformational change in Bid, Bcl-2, or Bax that signals cell death.

xi. Bik

Bik (Bcl-2 interacting killer) is a novel Bcl-2 family member that was detected when a human B-cell line cDNA library was used in a yeast two hybrid screen for proteins that interact with Bcl-2 (Boyd et al., 1995). Bik is a 160 amino acid protein and has a predicted molecular weight of 18 kD encoded by 928 bp cDNA and 1 Kb mRNA. Bik shares homology only within the BH3 domain of the Bcl-2 family and has a carboxy-terminal transmembrane hydrophobic domain. Bik was found to localize to the nuclear envelope and cytoplasmic membrane structures.

Transient co-transfection of Bik and β-galactosidase expression plasmids in Rat-1 fibroblasts resulted in a dramatic reduction in the number of blue cells, consistent with reduced viability of Bik transfected cells (Boyd et al., 1995). Co-transfection of Bik and Bcl-2, Bcl-x, adenovirus E1B-19 kDa, or EBV-BHRF1 resulted in an increase in blue cell number indicating the ability of these proteins to reverse cell death by Bik. Deletion of the BH3 domain of Bik resulted in loss of its pro-apoptotic activity. Bik induced apoptosis was shown to be inhibited by zVAD-fmk. However, CrmA could not inhibit Bik induced cell death. This suggests that Bik induced cell death involves selective activation of CPP32-like proteases (Orth and Dixit, 1997).

Interactions between Bik and other Bcl-2 family members was examined using the yeast two hybrid system, GST-fusion protein capture on glutathione agarose beads, and transient co-transfection of tagged Bik with other anti-apoptotic Bcl-2 family members (Boyd et al., 1995). These in vitro and in vivo studies revealed interactions between Bik and Bcl-2, Bcl-x, adenovirus E1B-19 kDa, and EBV-BHRF1. Bik also interacts with Bcl-$x_S$, a death promoting protein that lacks BH1 and BH2 domains. This suggests that Bik does not require BH1 and BH2 domain for its interaction with Bcl-2 family members. Bcl-2 residues 43–48 and E1B-19 kDa residues 90–96 were shown to be essential for interaction with Bik. Noteworthy is that these residues are not within the conserved regions of Bcl-2 family members.

xii. Bcl-w

Bcl-w was cloned using degenerate primers to the conserved BH1 and BH2 domains in a low stringency PCR™ reaction (Gibson et al, 1996). These primers were used to amplify cDNA from mouse macrophage and mouse brain cell lines. The PCR™ product was then used to screen cDNA libraries from mouse brain, spleen, and myeloid cell lines. Bcl-w is a 22 Kb gene with a 3.7 Kb mRNA which encodes a 22 kD protein. Human Bcl-w was then isolated from an adult human brain cDNA library. Bcl-w possesses the BH1, BH2, and BH3 domains. The human and mouse genes are 99% identical at the amino acid level and 94% at the nucleotide level.

Bcl-w mRNA is expressed at high levels in brain, colon, and salivary gland. Surprisingly, Bcl-w expression is not detected in T- and B-lymphoid cell lines. However, mRNA was detected in myeloid cell lines of macrophage, megakaryocyte, erythroid, and mast cell origin. Bcl-w also has a hydrophobic C-terminal transmembrane domain. The cytoplasmic localization of Bcl-w is similar to that of Bcl-2. Bcl-w resides in the central region of mouse chromosome 14 and human chromosome 14 at q 11.2. Hematopoetic cell lines expressing Bcl-w were resistant to apoptosis induction to the same extent as Bcl-2 and Bcl-x stable transfectants. However, Bcl-w did not protect CHI B-lymphoma cells from CD95-induced apoptosis while Bcl-2 and Bc-$X_L$ were able to do so (Gibson et al., 1996).

xiii. Harakiri

The Harakiri gene and its protein product Hrk was identified by a yeast two hybrid screen of a HeLA cDNA library to detect proteins that bind to Bcl-2 (Inohara et al., 1997). A 9-wk human embryo cDNA library was used to obtain the full length Hrk cDNA. Hrk was detected as a 716 bp cDNA that was confirmed by the northern blot analysis using both human and mouse tissue as 0.7 Kb mRNA. The cDNA encodes an open reading flame of 91 amino acids. Hrk shares homology with Bcl-2 family member BH3 domain, however, the rest of the protein has no significant homology to any other protein or Bcl-2 family. A region of 28 hydrophobic amino acids that may serve as a membrane-spanning domain was also identified at the COOH-terminus of Hrk.

Northern blot analysis demonstrates high levels of Hrk expression in all lymphoid tissues examined including the bone marrow and spleen. Hrk is also expressed in the pancreas and at low levels in the kidney, liver, lung, and brain (Inohara et al, 1997). Hrk was seen as a cytosolic granular staining by confocal microscopy of transiently transfected cells with flagged Hrk. This staining is similar to the previously reported localization of Bcl-2 and Bcl-x.

Transient transfections of Harakiri in 293T cells, HeLa, and FL5.12 progenitor B-cells resulted in a dramatic decrease in cell viability by 36 h post-transfection. However co-expression of Bcl-2 and Bcl-x could inhibit the death promoting activity of Hrk. Interestingly, Hrk appears to interact only with Bcl-2 and Bcl-$x_L$ but not with the other pro-apoptotic family members Bax, Bak, and Bcl-$x_S$. Deletion mutants of Hrk lacking 16 amino acids including the BH3 domain were unable to interact with Bcl-2 and Bcl-x. This mutant also failed to induce cell death in 293T cells. Deletion analysis has also revealed the requirement of BH1 and BH2 domains of Bcl-2 and Bcl-x to interact with Hrk.

C. Interactions of Bcl-2 family members and mechanisms of function

One of the reasons for the modest understanding of the mechanisms by which Bcl-2 homologues execute their cellular roles stems from a lack of identifiable sequence motifs in the Bcl-2 family which would implicate a mechanism of action. What have been defined, however, are shared domains designated as Bcl-2 homology domain 1, 2, 3 and 4. The BH1 domain spans amino acid residues 136–155 of the Bcl-2 protein, BH2 spans resides 187-202, BH3 spans resides 93-107 and BH4 spans residues 10–30. The BH3 domain, for its pan appears to be involved in selective interactions between Bcl-2 family members.

The BH3 domain appears to be required for the death promoting activity of Bax and bak are required for their interaction with two death-repressing members, Bcl-2 and Bcl-$x_L$ (Zha et al., 1996a; Chittenden et al., 1995).

The BH1 and BH2 domains serve equally important functions. The creation of point mutations in either domain, can effectively abolish the death repression function of Bcl-2 (Yin et al., 1994). Recent evidence suggests, however, that the formation of heterodimers is not required for function of family members (Cheng et al., 1996). These same BH1 and BH2 domain mutants of Bcl-2 fail to heterodimerize with Bax, although they do homodimerize well (Yin et al., 1994). Some of the most compelling evidence that the BH3 motif represents a "death domain" comes from studies of Bid (Wang et al., 1996c). Bid possesses only the BH3 domain, lacks the carboxy-terminal signal-anchor segment, and localizes to both cytosolic and membrane compartments.

Importantly, ectopic expression of Bid abrogates the pro-survival effect of Bcl-2. Additionally, expression of Bid, without another death stimulus, induces ICE-like proteases and apoptosis. An intact BH3 domain of Bid was required to bind the BH1 domain of either Bcl-2 or Bax.

The BH4 domain, which is located at the amino-terminus has been far less characterized. To date, it has been reported that deletion of the BH4 domain of Bcl-2 nullifies anti-apoptotic function and homodimerization, but does not impair Bcl-2/Bax heterodimerization (Reed et al., 1996). There is some evidence which indicates that the BH4 domain may mediate interactions of Bcl-2 family member protein with non-Bcl-2-related proteins such as calcineurin (Shibasaki et al., 1997). Thus the BH4 domain may serve as an tethering domain that bridges Bcl-2 and Bcl-2-related proteins to important signal transduction proteins.

Perhaps, at its simplest level, the expression of various Bcl-2 related proteins may determine whether a cell responds to an applied stress by initiating a cell death program or surviving. However, another hypothesis, that has substantial experimental evidence based on a mutational analysis of the BH domains, suggests that the cellular response to injury may be a function of the multiple heterodimerization and homodimerization states between members of this protein family. This model, commonly known as the "rheostat model" has been advocated by Dr. Stanley Korsmeyer's group (Oltvai et al., 1993; Korsmeyer et al., 1993). In this scenario, the relative levels of dimerization partners available shifts the balance of cell fate in favor of viability (e.g., Bcl-2/Bcl-2 homodimers favoring cell survival) or cell death (e.g., Bax/Bax homodimers favoring cell death) following exposure to an appropriate stress. This ability of Bcl-2-related proteins to hereto- and homodimerize in vivo, is perhaps one of the most important features of the family.

Complicating the picture further are reports of the ability of several Bcl-2 family members to physically interact with several signaling protein complexes containing p21 ras (Chen and Faller, 1996), Raf-1 kinase (Wang et al., 1996b) and p23 R-ras proteins (Wang et al., 1995). Another feature, is the conservation of a hydrophobic membrane targeting sequence in the carboxy-terminal tail of most members of the Bcl-2 family. The targeting domain most likely ensures that the various members are correctly routed to the appropriate intracellular organelle. Perhaps, this routing domain ensures that the various Bcl-2-related proteins are localized in close proximity to secure proper physical interactions should the appropriate stress be detected.

The mechanisms of programmed cell death are far from being completely elucidated. At present, many different factors such as protease activation (Yuan, et al., 1993; Fraser and Evan, et al., 1996; Chinnaiyan et al., 1997), DNA cleavage, and calcium signaling (Lam et al., 1994; Marin et al., 1996; Minn et al., 1997) are known to participate in apoptosis. The placement of Bcl-2 and Bcl-2 family members in cell death regulatory pathways is now being elucidated. It is now known that Bcl-$x_L$ can form ion channels and it may be that other Bcl-2 family members function in a similar manner. The specific interactions that Bcl-2 family proteins have with various signaling molecules and within the Bcl-2 family itself are active areas of investigation.

D. Engineering Expression Constructs

In certain embodiments, the present invention involves the manipulation of genetic material to produce expression constructs that encode therapeutic genes. Such methods involve the generation of expression constructs containing, for example, a heterologous DNA encoding a gene of interest and a means for its expression, replicating the vector in an appropriate helper cell, obtaining viral particles produced therefrom, and infecting cells with the recombinant virus particles.

The gene will be a therapeutic gene such as one or more of the proapoptotic genes discussed herein above, or the gene may be a second therapeutic gene or nucleic acid useful in the treatment of, for example cancer cells. In the context of gene therapy, the gene will be a heterologous DNA, meant to include DNA derived from a source other than the viral genome which provides the backbone of the vector. Finally, the virus may act as a live viral vaccine and express an antigen of interest for the production of antibodies thereagainst. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA also may include a regulatory sequence which may be derived from one source and the gene from a different source.

i. Additional Therapeutic Genes

The present invention contemplates the use of a variety of different genes in combination with adenoviral Bax and the proapoptotic Bcl-2 gene constructs. For example, genes encoding enzymes, hormones, cytokines, oncogenes, receptors, tumor suppressors, transcription factors, drug selectable markers, toxins and various antigens are contemplated as suitable genes for use according to the present invention. In addition, antisense constructs derived from oncogenes are other "genes" of interest according to the present invention.

a. p53

As stated earlier, p53 currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects. It is thus proposed that the treatment of p53-associated cancers with wild-type p53 or other therapies described herein will reduce the number of malignant cells or their growth rate, alternatively the treatment will result in the decrease of the metastatic potential of the cancer cell, a decrease in tumor size or a halt in the growth the tumor.

b. p16

The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $A16^{INK4}$ gene alterations is much lower in primary uncultured tumors than in cultured cell lines (Caldas et al., 1994; Cheng et al, 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type $A16^{INK4}$ function by transfection with a plasmid expression vector reduced colony formation by some human cancer cell lines (Okamoto, 1994; Arap, 1995).

c. C-CAM

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumors growth in vitro and in vivo.

d. Other Tumor Suppressors

Other tumor suppressors that may be employed according to the present invention include RB, APC, DCC, NF-1, NF-2, WT-1, MEN-I, MEN-II, zac1, p73, VHL, MMAC1, FCC and MCC. Additional inducers of apoptosis in addition to those of the Bcl-2 family, such as, Ad E1B and ICE-CED3 proteases, similarly could find use according to the present invention.

e. Enzymes

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

f. Cytokines

Other classes of genes that are contemplated to be inserted into the therapeutic expression constructs of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

g. Antibodies

In yet another embodiment, the heterologous gene may include a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules can be used in combination with the present invention, including antibodies against oncogenes, toxins, hormones, enzymes, viral or bacterial antigens, transcription factors, receptors and the like.

ii. Antisense Constructs

Oncogenes such as ras, myc, neu, rqf erb, src, fms, jun, trk, ret, gsp, hst, and abl as well as the antiapoptotic member of the Bcl-2 family also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

iii. Ribozyme Constructs

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

iv. Selectable Markers

In certain embodiments of the invention, the therapeutic expression constructs of the present invention contain nucleic acid constructs whose expression may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) may be employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, β-gal or chloramphenicol acetyltransferase (CAT).

v. Multigene Constructs and IRES

In certain embodiments of the invention, the use of internal ribosome binding sites (IRES) elements are used to create multigene polycistronic messages. IRES elements are able to bypass the ribosome scanning model of 5'-methylated, Cap-dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

vi. Control Regions

A. Promoters

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the machinery of the cell, or introduced machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constituitively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constituitively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 2).

TABLE 2

Tissue specific promoters

| Tissue | Promoter |
|---|---|
| Pancreas | insulin |
| | elastin |
| | amylase |
| | pdr-1 pdx-1 |
| | glucokinase |
| Liver | albumin PEPCK |
| | HBV enhancer |
| | alpha fetoprotein |
| | apolipoprotein C |
| | alpha-1 antitrypsin |
| | vitellogenin, NF-AB |
| | Transthyretin |
| Skeletal muscle | myosin H chain |
| | muscle creatine kinase |
| | dystrophin |
| | calpain p94 |
| | skeletal alpha-actin |
| | fast troponin 1 |
| Skin | keratin K6 |
| | keratin K1 |
| Lung | CFTR |
| | human cytokeratin 18 (K18) |
| | pulmonary surfactant proteins A, B and C |
| | CC-10 |
| | P1 |
| Smooth muscle | sm22 alpha |
| | SM-alpha-actin |
| Endothelium | endothelin-1 |
| | E-selectin |
| | von Willebrand factor |
| | TIE (Korhonen et al., 1995) |
| | KDR/flk-1 |
| Melanocytes | tyrosinase |
| Adipose tissue | lipoprotein lipase (Zechner et al., 1988) |
| | adipsin (Spiegelman et al., 1989) |
| | acetyl-CoA carboxylase (Pape and Kim, 1989) |
| | glycerophosphate dehydrogenase (Dani et al., 1989) |
| | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCAI could be used.

Tumor specific promoters such as osteocalcin, hypoxia-responsive element (HRE), MAGE-4, CEA, alpha-fetoprotein, GRP78/BiP and tyrosinase may also be used to regulate gene expression in tumor cells. Other promoters that could be used according to the present invention include Lac-regulatable, chemotherapy inducible (e.g. MDR), and heat (hyperthermia) inducible promoters, Radiation-inducible (e.g., EGR (Joki et al., 1995)), Alpha-inhibin, RNA pol III tRNA met and other amino acid promoters, U1snRNA (Bartlett et al., 1996), MC-1, PGK, -actin and alpha-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

B. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 3 and Table 4). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 3

| ENHANCER |
|---|
| Immunoglobulin Heavy Chain |
| Immunoglobulin Light Chain |
| T-Cell Receptor |
| HLA DQ α and DQ β |
| β-Interferon |

TABLE 3-continued

ENHANCER

Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 4

| Element | Inducer |
|---|---|
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

C. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

E. Methods of Gene Transfer

In order to mediate the effect transgene expression in a cell, it will be necessary to transfer the therapeutic expression constructs of the present invention into a cell. Such transfer may employ viral or non-viral methods of gene transfer. This section provides a discussion of methods and compositions of gene transfer.

i. Viral Vector-Mediated Transfer

The proapoptotic Bcl-2 genes are incorporated into an adenoviral infectious particle to mediate gene transfer to a cell. Additional expression constructs encoding other therapeutic agents as described herein may also be transferred via viral transduction using infectious viral particles, for example, by transformation with an adenovirus vector of the present invention as described herein below. Alternatively, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. Though adenovirus is exemplified, the present methods may be advantageously employed with other viral vectors, as discussed below.

Adenovirus. Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5-1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194–358 bp) region of the genome grew poorly even in a cell line that complemented the early (E1A) function (Hearing and Shenk, 1983). When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

Adeno-associated Virus. AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996; Chatterjee et al, 1995; Ferrari et al, 1996; Fisher et al, 1996; Flotte et al, 1993; Goodman et al, 1994; Kaplitt et al, 1994; 1996; Kessler et al, 1996; Koeberl et al, 1997; Mizukami et al, 1996; Xiao et al, 1996).

AAV-mediated efficient gene transfer and expression in the lung has led to clinical trials for the treatment of cystic fibrosis (Carter and Flotte, 1996; Flotte et al, 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al, 1996; Flotte et al, 1993; Kaplitt et al., 1994; 1996; Koeberl et al., 1997; McCown et al, 1996; Ping et al, 1996; Xiao et al, 1996).

Other Viral Vectors. Other viral vectors may be employed as expression constructs in the present invention. Vectors derived from viruses such as vaccinia virus (Ridgeway, 1988; Baichwal and Sugden, 1986; Coupar et al., 1988) canary pox virus, and herpes viruses may be employed. These viruses offer several features for use in gene transfer into various mammalian cells.

ii. Non-viral Transfer

DNA constructs of the present invention are generally delivered to a cell, in certain situations, the nucleic acid to be transferred is non-infectious, and can be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the P-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

F. Gene Delivery System for Toxic Gene Products

It is now known that programmed cell death, or apoptosis, plays an important role in development, homeostasis, and disease processes. It is contemplated in the present invention, that genes involved in apoptotic pathways may be useful in the treatment of diseases related to disorders in these pathways. In another embodiment, the use of non-proapoptic, cytotoxic genes are contemplated for use in treating hyperproliferative and other disease states in which cell death would be therapeutic.

The use of proapoptotic genes to treat cancers was proposed several years ago (Fisher, 1994; Thompson, 1995). However, the expression of pro-apoptic genes often results in death of the host cell if their expression is not regulated. In another embodiment of the present invention, it is contemplated that a novel co-transfer vector system is used to permit delivery of vectors that express potentially toxic genes. For example, the expression of Bcl-2 family member via gene transfer may be valuable in the treatment of a variety of hyperproliferative diseases, such as cancer. However, constructing an adenoviral vector expressing a pro-apoptic gene driven by a constitutive promoter becomes problematic in the packaging cell, presumably because of its high apoptotic activity (i.e., cell toxicity).

In one embodiment, the inventors demonstrate a system for safely inducing the expression of the bax gene in a host cell by adenovirus-mediated gene co-transfer. The system provides a first adenoviral vector containing a human gene wherein the expression product is cytotoxic. The cytotoxic gene is driven by a promoter, not active in the host or target cell. A second adenoviral vector is provided, wherein the gene, under the control of a promoter, encodes a transactivating protein. Induction of the promoter driving the expression of the transactivating protein, initiates the expression of the cytotoxic gene product.

Experimental data demonstrate that the vector expresses a minimal background level of bax protein in cultured mammalian cells thus preventing apoptosis of packaging cells. The expression of the bax gene was substantially induced both in vitro and in vivo by transferring it into target cells along with of an adenoviral vector expressing the transactivator, fusion protein GAL4/NVP16. Thus, adenovirus-mediated gene co-transfer permits the regulated expression of bax via the inducible expression of the GAL4/NVP16 gene. In other embodiments of the invention, the pro-apoptic genes Bak, Bim, Bik, Bid, Bad and Harakiri are contemplated for use in adenovirus-mediated gene co-transfer.

Adenovirus-mediated gene co-transfer is not limited to proapoptotic genes or a specific promoter. It also is contemplated that co-transfer system could be used to treat various hyperproliferative diseases, wherein regulating the expression of a toxic gene product is desired. Depending on the tissue being treated, a tissue specific promoter could be chosen to permit in vivo transactivation only in the target tissue. For example, co-transfer of a tumor suppressor gene linked to a promoter and a vector expressing a transactivator that specifically binds to the promoter, would be useful in treating hyperproliferative diseases. Thus, in one embodiment of the invention, a promoter linked to a particular gene can be selected to provide tissue specific expression. Regulated co-transfer expression of other toxic gene products also are contemplated and discussed below.

i. Vector Co-transfer and Promoters

The use of proapoptotic genes to treat cancers via gene therapy has not been reported, possibly due to the difficulty in constructing vectors that can efficiently transduce target cells with such genes. For example, Larregina et al. showed that constructing an adenovirus expressing the Fas-Ligand (Fas-L) was difficult because Fas-L induces apoptosis in 293 packaging cells, (Larregina et al., 1998). Arai et al. achieved efficient antitumor activity by adenovirus-mediated Fas-L gene transfer, but this required the use of 293 cells resistant to Fas-L or caspase inhibitor for vector production, (Arai et al., 1997).

The gene co-transfer system of the present invention overcomes these obstacles, by providing a pro-apoptic gene linked to a regulatable, promoter. The regulatable promoter prevents expression of the pro-apoptic gene in the host or packaging cell, which would result in cell death. The expression of the pro-apoptic gene is induced by a transactivator protein, carried by a gene on a second expression vector. In one embodiment of the present invention, adenovirus-mediated gene co-transfer uses a first adenovirus comprising human bax cDNA driven by a promoter consisting of a heptamer of GAL4-binding sites and a TATA box. A second adenovirus (i.e., co-transfer) comprising the GAL4/VP16 transactivator fusion protein linked to a regulatable promoter operable in eukaryotic cells, is provided to selectively induce bax expression. It is contemplated in other embodiments, that the first promoter can be the ecdysone-responsive promoter or Tet-On™ and the inducer of the first promoter ecdysone or muristeron A and doxycycline, respectively. For a complete description of the ecdysone system and Tet-On™ see section D, herein. It also is contemplated, that that the first promoter can be the HIV-1 LTR or HIV-2 LTR and the inducer of the first promoter tat. It is contemplated in other embodiments, that yeast, *E. Coli* and insect promoters may also be useful in the present invention for regulated expression of cytotoxic genes.

For human or mammalian cytotoxic gene therapy via vector-mediated gene co-transfer, the Bcl-2 genes Bak, Bim, Bik, Bid, Bad and Harakiri are contemplated as useful in the present invention. Additional cytotoxic gene products contemplated as useful in the present invention, are described below.

It is contemplated in the present invention that a gene encoding a transactivating protein is supplied by a second vector. In certain embodiments, the gene encoding the transactivating protein can be linked to a constitutive promoter. In other embodiments, the gene encoding the transactivating protein can be under the control of an inducible promoter, permitting regulated expression of the transactivating protein. Pancreatic, liver, skeletal muscle, smooth muscle, skin, lung, endothelium and blood are some examples of tissues in which tissue specific promoters might be selected for use. Table 2, Table 3 and Table 4 provide a list of some useful tissue specific promoters, promoter/enhancers and inducible promoter/enhancers, respectively, that may be used in combination and are considered useful in the present invention.

An important consideration when selecting a promoter to drive the expression of the cytotoxic gene product on the first vector, is that the transactivating protein (i.e., inducer) is not active in the host cell. For example, if the host cell expresses a transactivating protein, capable of activating the promoter on the first expression vector, upregulation of the cytotoxic gene may result.

The vector-mediated co-transfer system is particularly useful in vivo. In such embodiments, it may be desirable that transactivating protein also is not active in the target cell. The presence of the transactivating protein in the target cell would limit the temporal use of the co-delivery system, as the transactivating protein would be present at the time of delivery of the cytotoxic expression construct.

A variety of transactivating genes theoretically can be chosen to express transactivating protein factors, to drive the expression of a toxic gene on the first vector. Another consideration in choosing a transactivating protein factor is its efficacy of transcriptional activation in a given tissue type. It may be that a particular tissue specific transactivating factor has low levels of cross tissue activity, which could potentially be cytotoxic to healthy, normal cell or tissue types.

ii. In Vitro and In Vivo Delivery of Vectors to Target Cells

An adenoviral vector expressing a Blc-2 member gene, would facilitate the therapeutic evaluation of the Bcl-2 member gene, since such a vector would have potentially high transduction efficiencies in a variety of tissues. However, constructing an adenoviral vector that can express bax for example, has been problematic, presumably because of the bax gene's high apoptotic activity and its toxic effect on packaging 293 cells (Rosse et al., 1998). It is contemplated that vector-mediated gene co-transfer of the present invention will be useful for regulating both in vitro and in vivo expression of potentially cytotoxic gene products.

In one embodiment of the present invention, the in vitro expression of therapeutic genes are considered. In one example, shuttle plasmids in which bax cDNA was driven by a GAL4-responsive promoter consisting of five GAL4-binding sites and a TATA box (GT) were constructed. Recombinant viral vectors (Ad) were obtained after a single in vitro transfection of 293 cells with pAd/GT-Bax plus a 35-kb ClaI fragment from Ad/p53, (Zhang et al., 1993). Virus from a single plaque was expanded in 293 cells, twice purified and vector titer determined to be $3.3 \times 10^{12}$ viral particles/ml. Thus, the vector-mediated gene co-transfer system allows the in vitro replication of Ad/GT-Bax particles ($3.3 \times 10^{12}$ viral particles/ml) in the host cell (e.g., 293 cells), without killing the host cell (i.e. no Bax expression). The functionality of Ad/GT-Bax in vitro was documented by the co-transfer of Ad/GT-Bax and the transactivator Ad/PGK-GV16 to the cultured human lung carcinoma cell line H1299, demonstrating the induction of Bax expression via co-transfer. The in vitro expression of Bax in the vector-mediated gene co-transfer was also demonstrated to promote apoptosis in human lung cancer cell lines.

In other embodiments, the induction of therapeutic gene expression in vivo is contemplated for use in the present invention. Thus, in another example, to test whether bax gene expression could be similarly induced by adenovirus-mediated gene codelivery in vivo, adult Balb/c mice were infused via their tail veins with Ad/GT-Bax plus Ad/PGK-GV16, at a total vector dose of $6 \times 10^{10}$ particles/mouse and a vector ratio of 2:1. Mice were then sacrificed at 24 h after treatment, after which liver samples were harvested for western blot analysis and histopathological examination. A 14-fold increase in bax protein levels in animals treated with Ad/GT-Bax plus Ad/PGK-GV16 relative to control animals was observed as well as apoptosis of normal liver cells. These results demonstrate that bax expression can regulated in vivo by expressing GAL4/VP16 protein via the adenovirus-mediated gene co-transfer system.

In certain embodiments of the invention, the temporal sequence of vector-mediated co-transfer delivery is contemplated. In one embodiment, the vectors are delivered simultaneously. In other embodiments, the expression vector encoding the cytotoxic gene is delivered first, followed by the expression vector encoding the transactivating protein. In still other embodiments, the expression vector encoding the transactivating protein is delivered first, followed by the expression vector encoding the cytotoxic gene. The time between delivery of the first vector and the second vector is dependent on various parameters. Parameters to be considered when formulating a protocol include, but are not limited to, vector transducing efficiency, transducing cell type, efficiency of cytotoxic gene expression, efficiency of transactivating gene expression, cytotoxic protein stability and transactivating protein stability.

iii. Viral and Non-Viral Vectors

It is contemplated in the present invention, that gene co-transfer can be employed using any vector (i.e., viral, plasmid, shuttle vector). The therapeutic gene as described above, can be incorporated into an adenoviral infectious particle to mediate gene transfer to a cell. Alternatively, retrovirus, adeno-associated virus, vaccinia virus, canary pox virus, herpes virus, canary pox virus and reovirus also are contemplated as gene transfer vectors for use in the present invention.

In certain embodiments, non-viral vectors, such as plasmids, shuttle plasmids and cosmids are contemplated for use. Non-viral methods for the transfer of expression constructs into cultured mammalian cells include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988). For a more detailed description of both viral and non-viral methods and applications of gene transfer, refer to section F.

iv. Other Genes Toxic to Host Cells

In other embodiments of the present invention, the use of gene co-transfer system is contemplated for use in delivering non-pro-apoptic therapeutic genes that express potentially cytotoxic gene products. It is contemplated, that cancer, hyperproliferative (e.g., psoriasis, cytys) and inflammatory conditions (e.g. rheumatoid arthritis, allergies) could be treated by using the gene co-transfer system, by targeting these cells with genes that encode potentially cytotoxic products. It is contemplated that genes encoding cytokines (e.g., interferons), toxins antisense constructs, ribozymes, single chain antibodies, proteases and antigens would be useful in particular therapies, and that the co-transfer method will allow regulated expression of these genes.

In certain embodiments, various toxins are contemplated to be useful as part of the expression vectors of the present invention, these toxins include bacterial toxins such as ricin A-chain (Burbage, 1997), diphtheria toxin A (Massuda et al., 1997; Lidor, 1997), pertussis toxin A subunit, *E. coli* enterotoxin toxin A subunit, cholera toxin A subunit and pseudomonas toxin c-terminal. Recently, it was demonstrated that transfection of a plasmid containing the fusion protein regulatable diphtheria toxin A chain gene was cytotoxic for cancer cells. Thus, gene transfer of regulated toxin genes might also be applied to the treatment of cancers or other hyperproliferative diseases (Massuda et al., 1997).

In certain embodiments, cytokines such as IL-1, IL-2, IL-3, IL-4, IL-5, IL-6, IL-7, IL-8, IL-9, IL-10, IL-11 IL-12, GM-CSF, oncostatin M, TGF-$\beta$, TNF-$\alpha$, TNF-$\beta$ and G-CSF are contemplated for use in the vector-mediated co-transfer system.

In other embodiments, antisense constructs are contemplated for use in the present invention. Antisense methodology takes advantage of the fact that nucleic acids tend to pair with "complementary" sequences. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject. Engineering antisense constructs is covered in detail in Section D. Particular oncogenes that are targets for antisense constructs are ras, myc, neu, raf, erb, src, fms, jun, trk, ret, hst, gsp and abl. Also contemplated to be useful will be anti-apoptotic genes such as Bcl-2, Mcl-1, A1 and Bfl-1.

In still other embodiments, ribozymes are considered for use in the present invention. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme. Targets for this embodiment will include oncogenes such as ras, myc, neu, raf, erb, src, fins, jun, trk, ret, hst, gsp, bcl-2, EGFR, grb2 and abl. Other constructs will include overexpression of antiapoptotic genes such as bcl-2.

In yet another embodiment, one gene may comprise a single-chain antibody. Methods for the production of single-chain antibodies are well known to those of skill in the art. The skilled artisan is referred to U.S. Pat. No. 5,359,046, (incorporated herein by reference) for such methods and section D above.

Antibodies to a wide variety of molecules are contemplated, such as oncogenes, growth factors, hormones, enzymes, transcription factors or receptors.

In certain embodiments, it may be useful to express enzymes, that are potentially cytotoxic. For example, the protease caspase-7, has been implicated in apoptosis and thus potentially useful in gene therapy (Marcelli et al., 1999). One could express a variety of proteases, which have either been genetically engineered to function at physiological pH and/or active without enzymatic processing (Briand et al., 1999). Alternatively, proteases can be cloned from thermostable or pH stable organisms (Choi et al., 1999; Sundd et al., 1998). Thus, one could express a protease in a given cell and potentially inactivate via proteolysis, key metabolic and signaling proteins, needed for cell viability.

In another embodiment, treatment of protein folding disorders via the gene co-transfer system are contemplated.

For example, Cruetzfeldt-Jakob disease, Kuru, the human transmissible bovine spongiform encephalopathy (e.g., mad cow disease) and scrappie in sheep, are diseases related to cellular prion protein misfolding (Grandien and Wahren, 1998; Buschmann et al., 1998; Hill et al., 1999) The disease state ensues when an individual is exposesed to an infectious (mutated) form of the prion protein. This infectious prion protein (PrP(Sc)) acts as a misfolding catalyst or scaffold, and induces conformational changes in an individuals native prion proteins (PrP(C)), leading to the intraneuronal accumulation of a pathological prion isoform. Prions replicate in lymphoreticular tissues before neuroinvasion and have been demonstrated to be detectable via tonsil biopsy (Hill et al., 1999). It might be possible using vector-mediated co-transfer, to provide antisense mRNA to patients who test positive for PrP(Sc), to prevent transcription of prion mRNA and thus block protein synthesis. Alternatively, expression of cytokines could be targeted to lymphoreticular tissues, expression of proteases or specific antigens could be used to tag these cells for destruction, reducing prion protein expression. It is contemplated further in the present invention, that Alzheimer's disease could be treated similarly using vector-mediated co-transfer.

G. Pharmaceuticals And Methods Of Treating Cancer

In a particular aspect, the present invention provides methods for the treatment of various malignancies. Treatment methods will involve treating an individual with an effective amount of a viral particle, as described above, containing a therapeutic gene of interest. An effective amount is described, generally, as that amount sufficient to detectably and repeatedly to ameliorate, reduce, minimize or limit the extent of a disease or its symptoms. More rigorous definitions may apply, including elimination, eradication or cure of disease.

To kill cells, inhibit cell growth, inhibit metastasis, decrease tumor size and otherwise reverse or reduce the malignant phenotype of tumor cells, using the methods and compositions of the present invention, one would generally contact a "target" cell with the therapeutic expression construct. This may be combined with compositions comprising other agents effective in the treatment of cancer. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Depending on the particular cancer to be, administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

In certain embodiments, ex vivo therapies also are contemplated. Ex vivo therapies involve the removal, from a patient, of target cells. The cells are treated outside the patient's body and then returned. One example of ex vivo therapy would involve a variation of autologous bone marrow transplant. Many times, ABMT fails because some cancer cells are present in the withdrawn bone marrow, and return of the bone marrow to the treated patient results in repopulation of the patient with cancer cells. In one embodiment, however, the withdrawn bone marrow cells could be treated while outside the patient with an viral particle that targets and kills the cancer cell. Once the bone marrow cells are "purged," they can be reintroduced into the patient.

The treatments may include various "unit doses." Unit dose is defined as containing a predetermined-quantity of the therapeutic composition calculated to produce the desired responses in association with its administration, i.e., be appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time. Unit dose of the present invention may conveniently may be described in terms of plaque forming units (pfu) of the viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher.

Preferably, patients will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

i) Cancer Therapy

One of the preferred embodiments of the present invention involves the use of viral vectors to deliver therapeutic genes to cancer cells. Target cancer cells include cancers of the lung, brain, prostate, kidney, liver, ovary, breast, skin, stomach, esophagus, head and neck, testicles, colon, cervix, lymphatic system and blood. Of particular interest are non-small cell lung carcinomas including squamous cell carcinomas, adenocarcinomas and large cell undifferentiated carcinomas.

According to the present invention, one may treat the cancer by directly injection a tumor with the viral vector. Alternatively, the tumor may be infused or perfused with the vector using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

For tumors of >4 cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In certain embodiments, the tumor being treated may not, at least initially, be respectable. Treatments with therapeutic viral constructs may increase the respectability of the tumor due to shrinkage at the margins or by elimination of certain particularly invasive portions. Following treatments, resection may be possible. Additional viral treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Various combinations may be employed, gene therapy is "A" and the radio- or chemotherapeutic agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | | B/B/A/B | A/A/B/B | | A/B/A/B | A/B/B/A | B/B/A/A |
| B/A/B/A | | B/A/A/B | A/A/A/B | | B/A/A/A | A/B/A/A | A/A/B/A |

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Apoptotic Mechanisms following Adenovirus-mediated p53 Replacement Gene Therapy

Induction of program cell death pathway is a critical step in most anticancer therapies including adenovirus mediated wild-type p53 gene therapy. The transient expression of the adenovirus vector requires either induction of apoptosis, terminal differentiation, or cellular senescence in order to result in effective therapy. As the a further understanding of the mechanisms involved in this process is gained, this will enable us to design more effective therapeutic approaches to anticancer treatment.

Materials and Methods

Cell Culture. H358 and H1299 are non-small cell lung cancer cell lines with both copies of the p53 deleted and were obtained from A. Gazdar and J. Minna. H322j is a non-small cell lung cancer cell line with a p53 mutation. Cells were maintained in RPMI-1640 medium supplemented with 10% fetal calf serum, 10 mM glutamine, 100 units/ml of penicillin, 100 µg/ml of streptomycin, and 0.25 µg/ml of amphotericin B (Gibco-BRL, Life Technologies, Inc., Grand Island, N.Y.) and incubated at 37° C. in a 5% $CO_2$ incubator.

Adenovirus production. The construction and properties of the Adp53 have been reported elsewhere (Fujiwara et al., 1994; Zhang et al., 1993). The Ad5/CMV/β-gal virus was obtained from F. Graham, McMaster University, Hamilton, Ontario. The E1 deleted vector dl312 (obtained from T. Shenk, Princeton, N.J.) was utilized as a control vector. Adenovirus was prepared as previously described (Graham and Prevec, 1991) and purified by two rounds of cesium chloride ultracentrifugation. Purified virus was mixed with 10% glycerol and dialyzed twice against 1000 ml of a buffer containing 10 mM Tris HCl (pH 7.5), 1/µM $MgCl_2$, and 10% glycerol at 4° C. for 6 h. Purified virus was aliquoted and stored at −80° C. until used. Viral titer was determined by UV-spectrophotometric analysis (viral particles/ml) and by plaque assay (pfu/ml) (Zhang et al., 1995). Final viral concentrations for in vitro and in vivo infections were made by dilution of stock virus in PBS. Adenovirus preparations were free of replication-competent adenovirus as determined by previously described techniques(Zhang et al., 1995).

Gene delivery. In vitro transfection studies for all cell lines were performed by plating $5 \times 10^5$ cells in 100 mm plates (Falcon Plastics, Lincoln Park, N.J.). Forty-eight h after plating, cells were incubated for 2 h with purified virus in 2 mls of RPMI-1640 medium supplemented with 2% fetal calf serum. The multiplicity of infection (MOI) was based on cell counts of untreated plates. The MOI used for each cell line was chosen to result in an approximately 70–80% transduction based on preliminary studies using the Ad5/CMV/β-gal vector. These were an MOI of 5 pfu for the H1299 cell line, 70 pfu for the H358 cell line and 50 pfu for the H322j cell line. After 2 h, fresh RPMI-1640 medium supplemented with 10% fetal calf serum was added to the plates. Cells and cell lysate were collected at 6 h intervals up to 36 h following infection for western blot, cell cycle, and TUNEL assay analysis. This time course was chosen based on preliminary data indicating a large fraction of apoptotic cells were evident at these times and later time points resulted in the observance of degraded cellular proteins.

Western blot analysis. Total cell lysates were prepared by lysing monolayered cells in dishes with sodium dodecyl sulfate-polyacrylamide gel electrophoresis (SDS-PAGE) sample buffer after rinsing cells with phosphate buffered saline (PBS). Each lane was loaded with 50 fig of cell lysate protein as determined by BCA protein assay (Pierce, Rockford, Ill.). After SDS PAGE at 100 volts for two h, the proteins in the gels were transferred to hybond-ECL membrane (Amersham International PLC, Little Chalfont, Buckingham Shire, England). Membranes were blocked with 3% milk and 0.1% Tween 20 (Sigma Chemical Company) in PBS and incubated with antibody against the specified protein overnight at 4° C. The mouse anti-human p53 (D0–7) (Pharmigen, San Diego, Calif.), mouse anti-human Bcl-2 (124) (Dako Corp., Carpintenia, Calif.), mouse anti-human Bak (Oncogene Science), mouse anti-human Bax (Pharmigen, San Diego, Calif.), mouse anti-human Bcl-$X_L$ (Pharmigen, San Diego, Calif.), and mouse anti-human (β-actin monoclonal antibody (N350) (Amersham International PLC, Buckingham Shire, England) were used. The membranes were developed according to Amershams ECL western blotting protocol.

Flow cytometry analysis for cell cycle. To measure the DNA histogram, cells were fixed in 70% ethanol at 4° C. for greater than 24 h. The cells were incubated in propidium iodide (20 µg/ml) and ribonucleases (20 µg/ml) for 30 min at 37° C. All measures were made with an Epics Profile II (Coulter Corp., Hialeath, Fla.) equipped with an air-cooled argon ion laser admitting 488 NM at 15 MW. A minimum of 10,000 events per sample were analyzed and FITC fluorescence was collected using a 525 BP filter. Coulters cytologic program was used for data analysis. Mean peak fluorescence was determined for each histogram.

Terminal deoxynucleotidyl transferase-mediated dUTP-biotin nick end labeling (TUNEL) Assay. The TUNEL assay was performed utilizing the procedure described by Gorczyca et al. (1992). Briefly, fixed cells were washed in PBS and resuspended in 50 µl of TdT buffer with 5 units of TdT enzyme (Sigma Chemical Co.) and 0.5 nmol biotin-16-dUTP (Boehringer Mannheim Co.). Controls were prepared without TdT enzyme. Cells were incubated at 37° C. for 1 hour, rinsed in PBS, and resuspended in 100 ml of avidin-FITC, 2.5 mg/ml, (Boehringer Mannheim Co.) in saline-citrate buffer containing 0.1% Triton X-100, 0.1% BSA, 0.5 M NaCl, and 0.06 M Na citrate. Specimens were incubated in the dark for 30 min, washed in PBS with 0.1% Triton X-100, resuspended in propidium iodine (5 µg/ml) and 0.1% RNAse A. After incubation for 30 min the specimens were analyzed with the use of an EPICS Profile II flow cytometer (Coulter Corp., Hialeah, Fla.). An analysis region was set based on the negative controls and the percent of labeled cells was calculated from this region.

Evaluation of apoptosis. For evaluation of apoptosis induced by the Ad-Bax vector, the breast carcinoma cell lines MDA-MB-468, MCF-7, and SKBr3 were used. The cells were plated at $0.5 \times 10^6$ and then treated with Ad-Bax or viral control at an MOI of 100 viral particles per cell. Media alone was used for mock infection. At 2 and 4 days post transfection, the cells were harvested and fixed in 80% ETOH. After 24 hours, propidium iodide was added to each sample and the cells were analyzed by flow cytometry. The subdiploid cell population was assessed and the percent recorded as apoptotic cells.

Further analysis of apoptosis was determined by a cell death ELISA kit from Boehringer Mannheim. This is a photometric "sandwich enzyme immunoassay" which allows quantitative in vitro determination of histone-associated DNA fragments which are specific for apoptotic cell death. Briefly, MDA-MB-468 cells and MCF-7 cells were transfected at an MOI of 100 (Ad-Bax, viral control or media alone) and cells collected at 72 hours. Samples were incubated with anti-histone biotin and anti-DNA peroxidase in streptavidin coated plates. After removal of unbound antibodies, the amount of peroxidase retained was determined photometrically. The results are recorded as an enrichment factor which is a photometric quantitation above the control samples.

Results

Adp53 infection results in overexpression of p53 protein and induction of p21.

Expression of p53 protein in the H1299 cells was measured at 6 h intervals following Adp53 infection by western blot analysis. The control cells (mock infected) and dl312 (control vector) infected cells expressed no measurable p53 protein. p53 protein was observed at the 6 h time point following infection with Adp53. High expression at multiple phosphorylation states was observed at 24 h and continued to the 36 h time point. Induction of p21 was observed following infection with Adp53. Control cells and dl312 infected cells expressed low levels of p21 by western blotting analysis. However, induction of p21 was observed early following infection with Adp53. High levels of p21 were observed at the 18 h time point and continued to with high expression observed at 36 h. Similar results were observed at the 24 h time point for the H358 and H322J cell lines.

Adp53 infection results in a $G_1$ cell cycle arrest and induction of apoptosis.

Figure 2A:
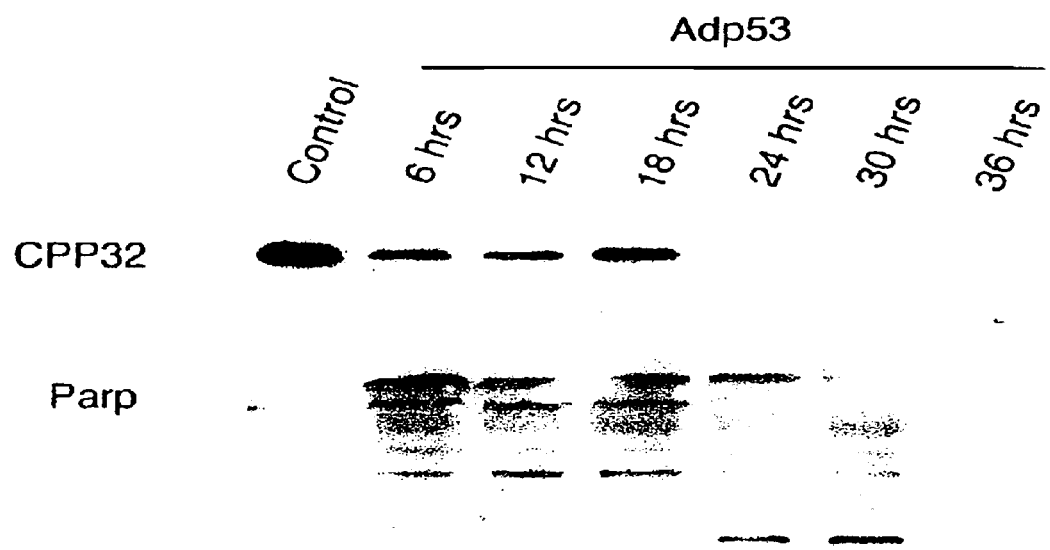
FIG. 2A and FIG. 2B. Western blot analysis of CPP32 and Parp expression. Control non-infected cells and cells following infection with Ad5/CMB/p53 were collected and subjected to western blot analysis using monoclonal antibody against CPP32 (FIG. 2B) or polyclonal antibody against parp (FIG. 2A). Fifty micrograms of protein was analyzed by SDS-PAGE and visualized by western blotting using the ECL chemiluminescence system. Image shown is an optical scan of a representative film exposure from one of three studies. The arrows indicate expected location of CPP32 and Parp cleavage product.
Figure 2B:
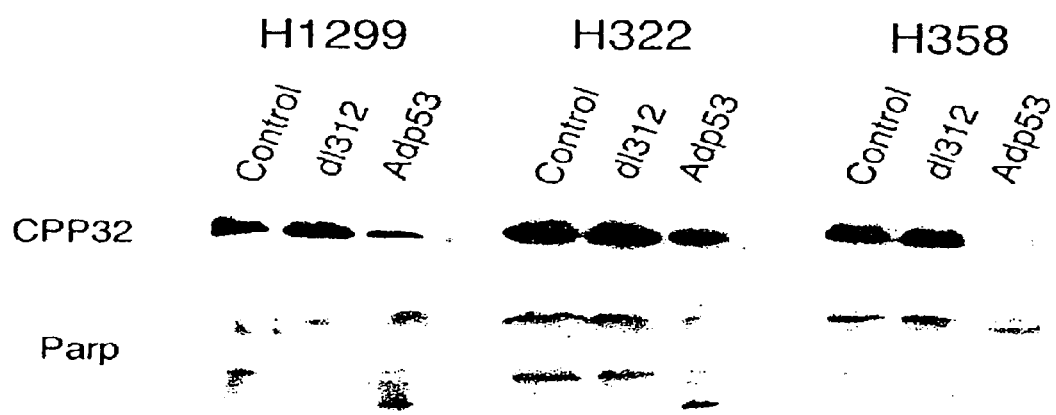

Cell cycle analysis of the H1299 cell line demonstrated an increase in the $G_1$ population of cells following infection with Adp53 compared to the control and dl312 infected cells (FIG. 2A. This increase in $G_1$ population of cells was observed as early as 12 h following Adp53 infection and was clearly evident at the 18 h time point (percent $G_1$: control= 38%, Adp53=59%) and continued to 36 h. Interestingly, accumulation of the sub 2N population of cells was observed at a time point slightly delayed from the time of accumulation of cells in $G_1$ cell cycle arrest. The sub 2N population of cells were observed at 24 h following infection with Adp53 and continued to accumulate up to 36 h following infection. This increase sub 2N population of cells corresponded to an increase labeling by TUNEL assay (FIG. 2B. These data are consistent with increases in apoptotic cell death.

Adp53 infection result in decreased levels of CPP32 and parp cleavage.

Figure 3A:
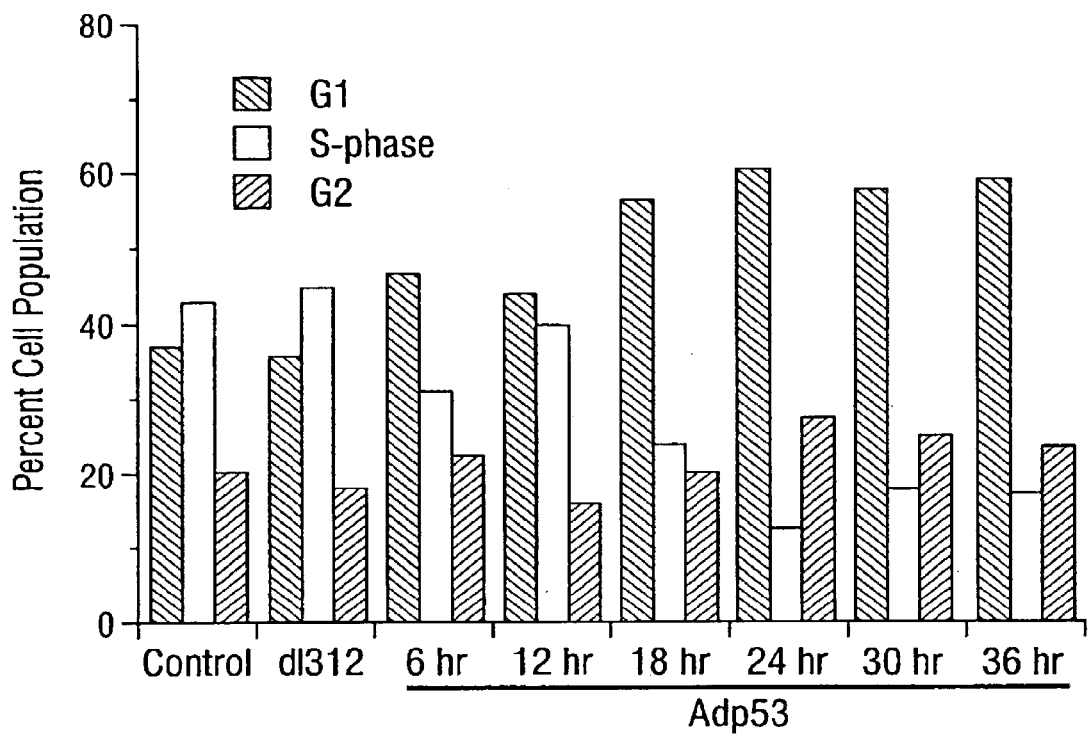
FIG. 3A and FIG. 3B. Effect of Ad5/CMV/p53 gene transfer on cell cycle regulation and induction of apoptosis. Cell cycle analysis and TUNEL were performed on cells which were treated with control vector DL312 or PBS or infected with Ad5/CMV/p53 and collected at 6 h intervals following infection. Cells were tripsinized at the reported time point fixed and analyzed for DNA content by perpidium iodine staining and analyzed for TUNEL labeling by fluorescence using flow cytometry. Infection with Ad5/CMV/p53 resulted in a increase in $G_1$ population of cells and an increase in the 2N population of cells (FIG. 3A). Additionally infection with Ad5/CMV/p53 resulted in an increased population of TUNEL-labeled cells consistent with increases in apoptotic death (FIG. 3B).
Figure 3B:
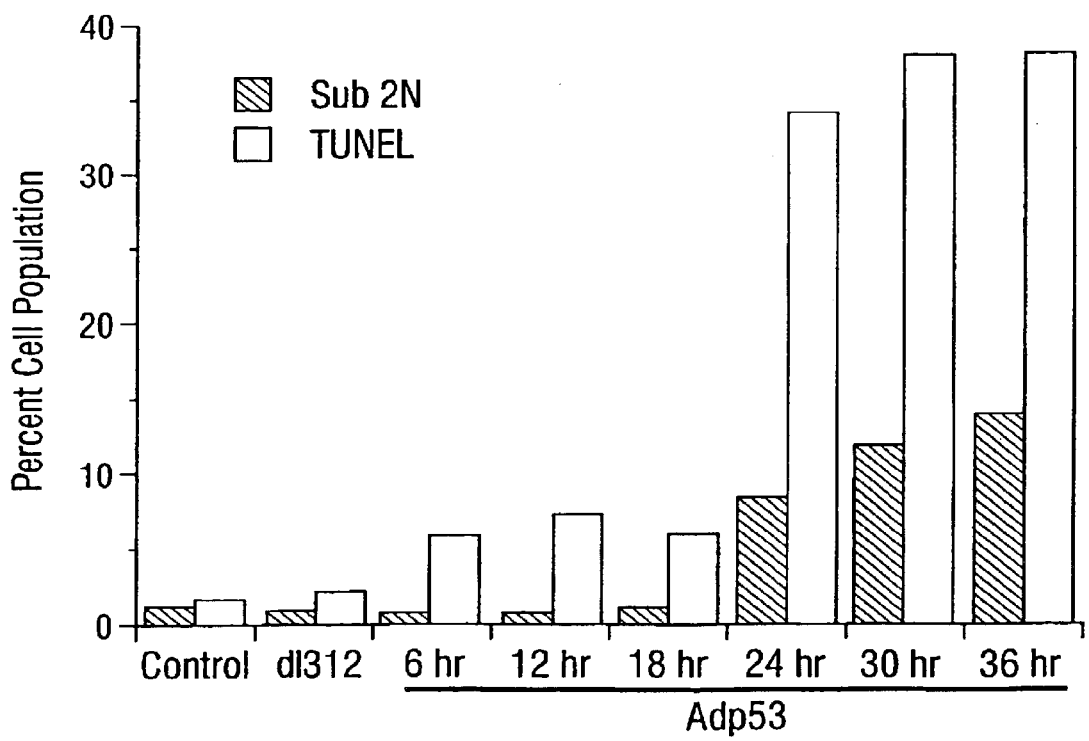

Levels of the inactive zymogen of CPP32 were observed in control and dl312 infected cells. Adp53 infection resulted in decreased levels of the inactive zymogen form of CPP32. These diminished levels of the CPP32 zymogen were observed at the 24 h time point and continued through the 36 h time point (FIG. 3A). This reduction in CPP32 levels was accompanied by concomitant evidence of cleavage of its early target Parp by western blot analysis. Similar results were observed at the 24 h time point for the H358 and H322J cell lines (FIG. 3B). The above data is again consistent with induction of apoptotic cell death, activation of the ICE-like protease CPP32, and cleavage of the CPP32 target Parp.

Adp53 infection did not effect the Bcl-2 or Bcl-$X_L$ expression.

No significant changes in the levels Bcl-x, and Bcl-2 proteins were observed by western blotting following infection with Adp53 as compared to control or dl312 infected cells. Similar results were observed at the 24 h time point for the H358 and H322J cell lines.

Overexpression of p53 results in induction of proapoptotic Bax and Bak proteins.

Bax protein levels were detectable in control and dl312 infected cells. Infection with Adp53 resulted in increased levels of Bax protein. This was especially evident at the 24 h time point and continued to 36 h. Bak protein expression was detectable by western blot analysis in control and dl312 infected cells. Following infection with Adp53, a significant increase in Bak protein levels were observed compared to controls. Again, peak levels were present at the 24 h time point and continued to the 36 h time point. Similar results were observed at the 24 h time point for the H358 and H322J cell lines.

EXAMPLE 2

The Adenoviral Bax Vector

Using the insights gained herein above, the inventors reasoned that the overexpression of p53 gene induces apoptosis by upregulating Bax. Thus if a vector could be designed that in itself mediated the upregulation of overexpression of Bax, there may be enough of an induction of Bax to induce apoptosis. In order to investigate this further the inventors constructed a new and novel adenoviral Bax vector as described herein below.

Cloning of the human Bax cDNA.

Total RNA was isolated from SRB I squamous cell carcinoma cell line using Ultraspec RNA isolation reagent (Biotecx). First strand cDNA was synthesized using 5 µg of RNA, 500 ng oligo (dT), 5× strand buffer, 0.1M DTT, 10 µM dNTP mix 1 µl of superscripapt II™ in a RT-PCR™ reaction. Polymerase chain reaction was then performed to amplify Bax cDNA using forward oligo primer 5'-GGAATTCGCGGTGATGGAC GGGTCCGG-3' (SEQ ID NO:5) and reverse oligo primer 5'-GGGAATTCTC-AGCCCATCTTCTTCCA GA-3' (SEQ ID NO:6). The reaction was incubated at 95° C. for 1 min, 56° C. for 2 min and 72° C. for 3 min for a total of 35 cycles. The PCR™ reaction was then resolved on 1.5% agarose gel. The Bax cDNA sequence was assessed with the M13 and T7 primers and was found to differ from the wildtype Bax sequence in the amino terminus. The highly conserved BH3 region which appears necessary for apoptosis was intact but a frameshift mutation existed which eliminated the BH1 and BH2 regions.

Construction of Adenoviral Bax vector

The TA PCR™II cloning vector (Invitrogen) containing the truncated Bax cDNA (SEQ ID NO:1 cDNA encodes protein of SEQ ID NO:2) was amplified and purified using Qiagen kit. The truncated Bax gene DNA fragment was isolated by digestion with restriction enzymes EcoRI (for the 5' side) and Not I (for the 3' side) and electroeluted on a 1.5% agarose gel. The truncated Bax gene was recovered from the gel with Qiagen DNA recovery kit and inserted into a polylinker between the Xba I and Cla I sites in the pXCJL.1 shuttle vector. The shuttle vector contains the left end of the adenovirus type 5 genome with the E1 region deleted. The resulting plasmid, p12 Bax, was cotransfected with the recombinant plasmid pJM17 into 293 kidney carcinoma cells which provided the deleted E1 region in ttrqns. pJM17 carries the bulk of the right side of the adenovirus type 5 genome.

Calcium phosphate mediated cotransfection of the two plasmids (p12Bax and pJM17) was performed with homologous recombination producing the adenoviral truncated Bax vector (AdBax). Successful adenoviral recombinants were identified by cytopathic changes in the transfected 293 cells. The adenoviral recombinants were amplified on 293 cells and harvested when a complete cytopathic effect was evident. The virus was isolated by free-thawing the cell pellets three times in dry ice ethanol bath and a 37° C. water bath.

Purification of the virus was performed with two cesium chloride gradient ultracentrifugations. The isolated virus was then dialyzed against a buffer (10 mM Tris-HCL, 1 mM $MgCl_2$ and 10% glycerol) to remove contaminating cesium chloride. Quantification of the virus was then performed with O.D. readings ad plaque assay on 293 cells. The purified virus was then analyzed for the presence of the truncated Bax gene by dideoxy DNA sequencing with PCR™ and two primers. The internal forward oligo primer 5'-GGGACGAACTGGACAGTAA-3' (SEQ ID NO:7) and reverse oligo primer 5'-GCACCAGTTTGCTGGCAAA-3' (SEQ ID NO:8) were used to sequence both strands of the adenoviral Bax gene. Additional confirmations was obtained with PCR™ primers located just upstream and downstream of the Bax insert in the adenovirus genome. These primers included the forward oligo 5'-ACGCAAATGGGCGGTAG-3' (SEQ ID NO:9) and reverse 5'-CAACTAGAA-GGCACAGT-3' (SEQ ID NO:10). Sequencing confirmed that the truncated Bax gene was correctly inserted in the adenoviral recombinant AdBax.

EXAMPLE 3

Induction of Apoptosis in Human Breast Cancer by Adenoviral Mediated Overexpression of Bax Apoptosis is controlled, at least in part, by the balance between the proapoptotic (Bax, Bak, Bcl-xs) and antiapoptotic (Bcl-2, Bcl-$X_L$) members of the Bcl-2 family. Altering the balance of these mediators can result in the suppression or induction of apoptosis. The present example describes the use of the novel adenoviral vector, Ad-Bax, to determine whether overexpression of Bax could induce apoptosis in human breast cancer.

The human Bax cDNA was isolated, sequenced and used to construct the Type 5, E1 deleted adenoviral vector as described herein above. The Ad-Bax vector contained a truncated Bax with an intact death (BH3) domain. Human breast cancer cell lines MDA-MB-468, SKBr3 and MCF-7 were transduced with Ad-Bax, E1 deleted viral control (AdV) or media alone (Cont.) at multiplicity of infection (MOI) of 100 to achieve an 85% transduction efficiency.

Apoptosis was evaluated by changes in cellular morphology, evidence of DNA-Histone complexes by ELISA and by FACS (FIG. 4A, FIG. 4B and FIG. 4C) analysis of subdiploid cells with propidium iodide staining.

Figure 4A:
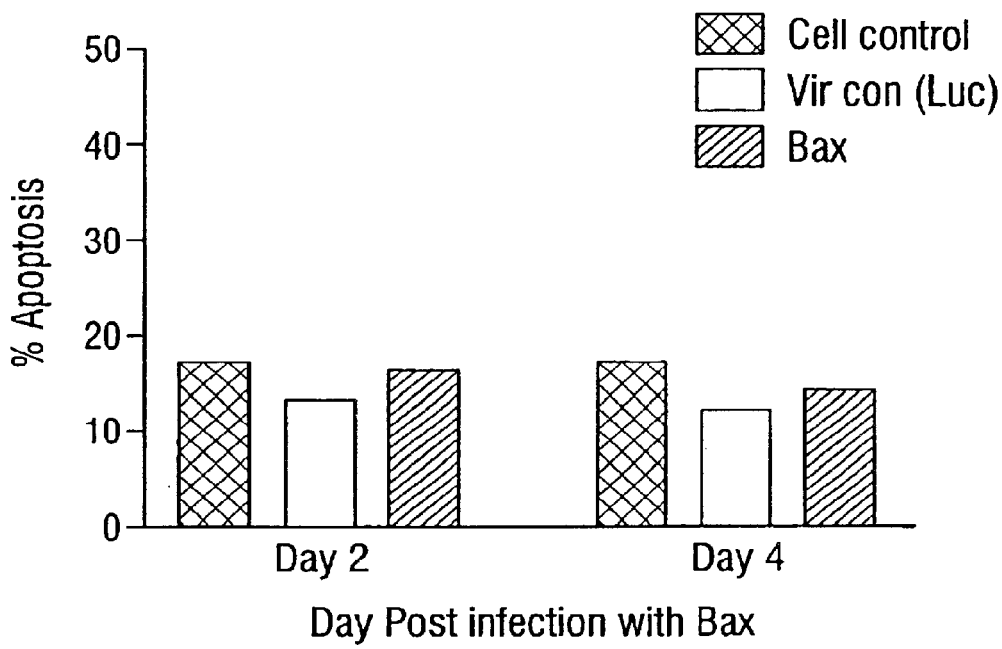
FIG. 4A, FIG. 4B, and FIG. 4C. FACS analysis to measure apoptosis in MCF-7 cells (FIG. 4A), SKBr3 cells (FIG. 4B) and MDA-MD-468 cells (FIG. 4C). Cells were either uninfected, infected with an empty adenoviral vector control, an adenovirus vector containing the truncated bax gene.
Figure 4B:
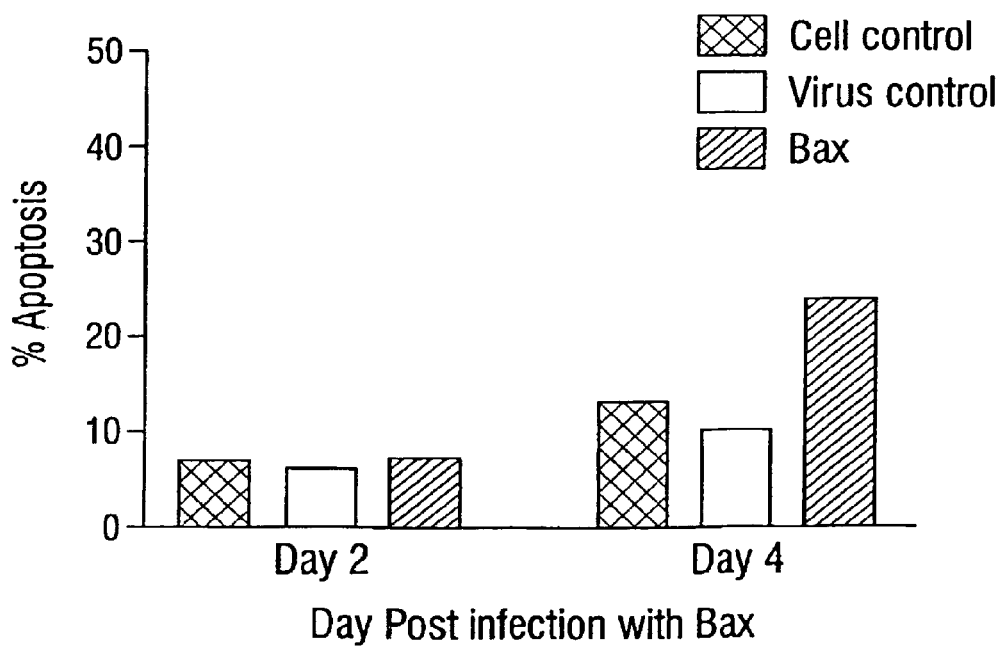
Figure 4C:
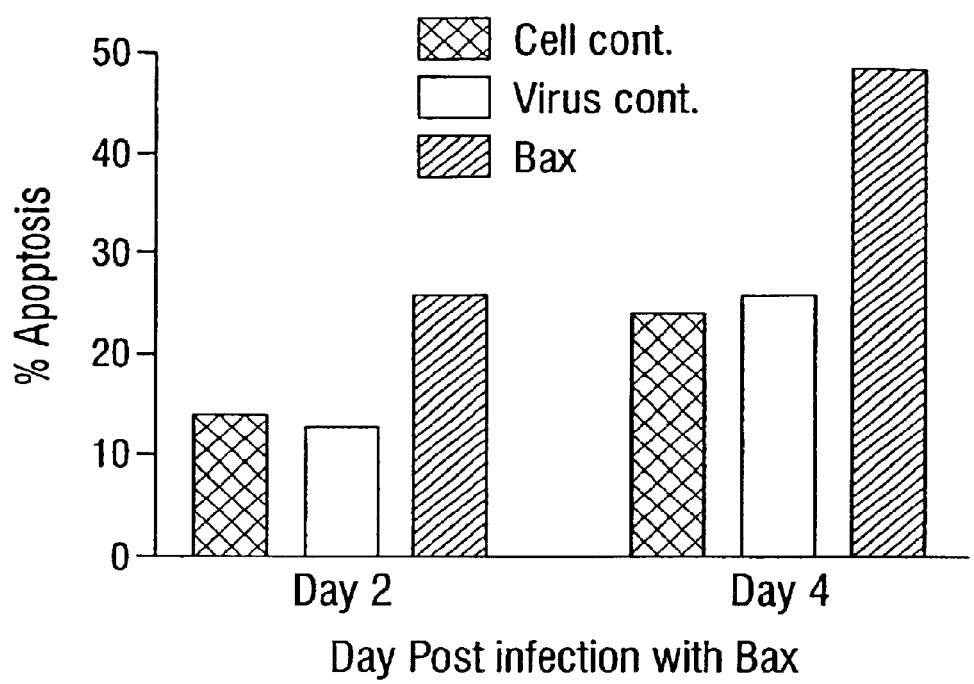

Western blot analysis confirmed overexpression of the Bax protein in the transduced cells. Apoptosis, by morphology, occurred four days after transduction with Ad-Bax in 468 and SKBr3 cells but not in MCF-7 cells (Table 5). FACS revealed a two-fold increase in apoptosis (FIG. 4A, FIG. 4B, and FIG. 4C). DNA-Histone complexes increased 40% in 468 cells with no increase in MCF-7 cells. Further Western analysis revealed similar levels of Bcl-xL in all cell lines. However, there were high levels of Bcl-2 only in the apoptosis-resistant MCF-2 cells (Table 5; FIG. 4A, FIG. 4B, and FIG. 4C).

TABLE 5

Adenovirally-mediated Bax induced Apoptosis and the Bcl-2 levels in MDA-MB-468, SKBr3 and MCF-7 cell lines

| Cell lines | % Apoptosis | | | BCL-2 Level |
|---|---|---|---|---|
| | Cont | AdV. | Ad-Bax | |
| MDA-MB-468 | 24 | 26 | 49 | Low |
| SKBr3 | 13 | 10 | 24 | Low |
| MCF-7 | 17 | 12 | 14 | High |

The present example demonstrates that adenoviral mediated gene transfer of Bax induces apoptosis in human breast cancer cell lines. Resistance to Ad-Bax induced apoptosis in MCF-7 cells may be due to the high cellular levels of Bcl-2. These results suggest that overexpression of the proapoptotic mediator Bax will be a novel and useful gene therapy strategy. Further, such gene therapy may be combined with inhibition of endogenous Bcl-2 to shift the proapoptotic/antiapoptotic equilibrium in favor of death promotion in cancer cells.

EXAMPLE 4

Construction of Wild-Type AdBax and AdBak Using a Cosmid System

Traditional methods of producing recombinant adenoviral vectors involve co-transfection of a plasmid encoding the transgene of interest and a shuttle vector carrying adenoviral genome sequences into a cell line such as 293 cells that express the E1A gene product. This allows for transactivation of adenoviral gene transcription and homologous recombination to produce a recombinant adenovirus that is replication deficient. Some drawbacks of this system are a low efficiency of homologous recombination, tedious cloning and plaque screening to identify the desired end product, and the production of a relatively high level of non-recombinant viruses in the viral preparation.

A relatively new method of producing recombinant adenoviral particles is the use of a cosmid adenoviral vector cloning system (Chartier et al., 1996, Fu and Deisseroth, 1997). The advantages to such a system high recombination efficiency in recA+E. coli bacteria, high capacity for heterologous DNA, a stable genome, easy isolation of recombinant virus, and the ability to construct recombinant adenoviruses that carry cytotoxic gene. In the present invention, pro-apoptotic genes such as bax and bak are capable of being introduced into the adenoviral genome and produced by this system while not killing the producer cell.

Figure 5:
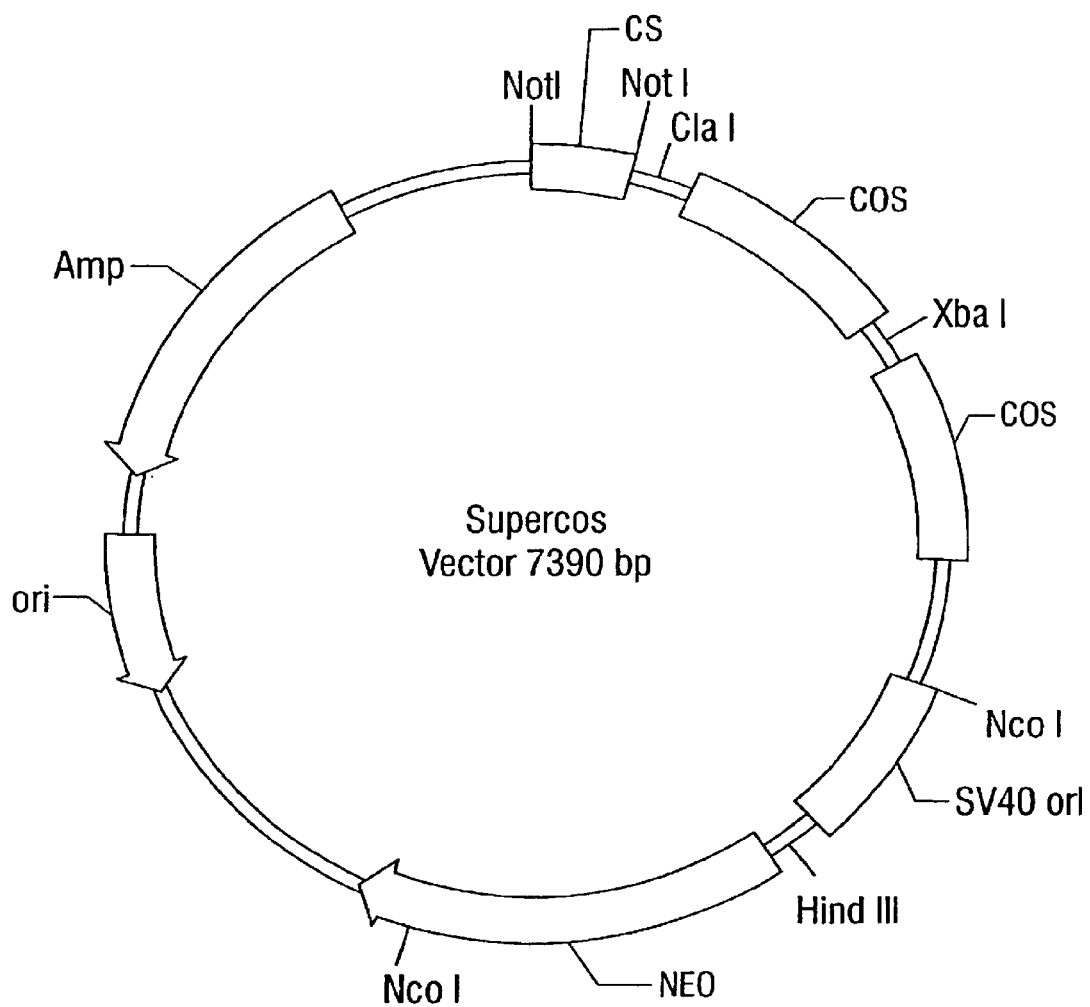
FIG. 5. Plasmid map of the Supercos vector.
Figure 6:
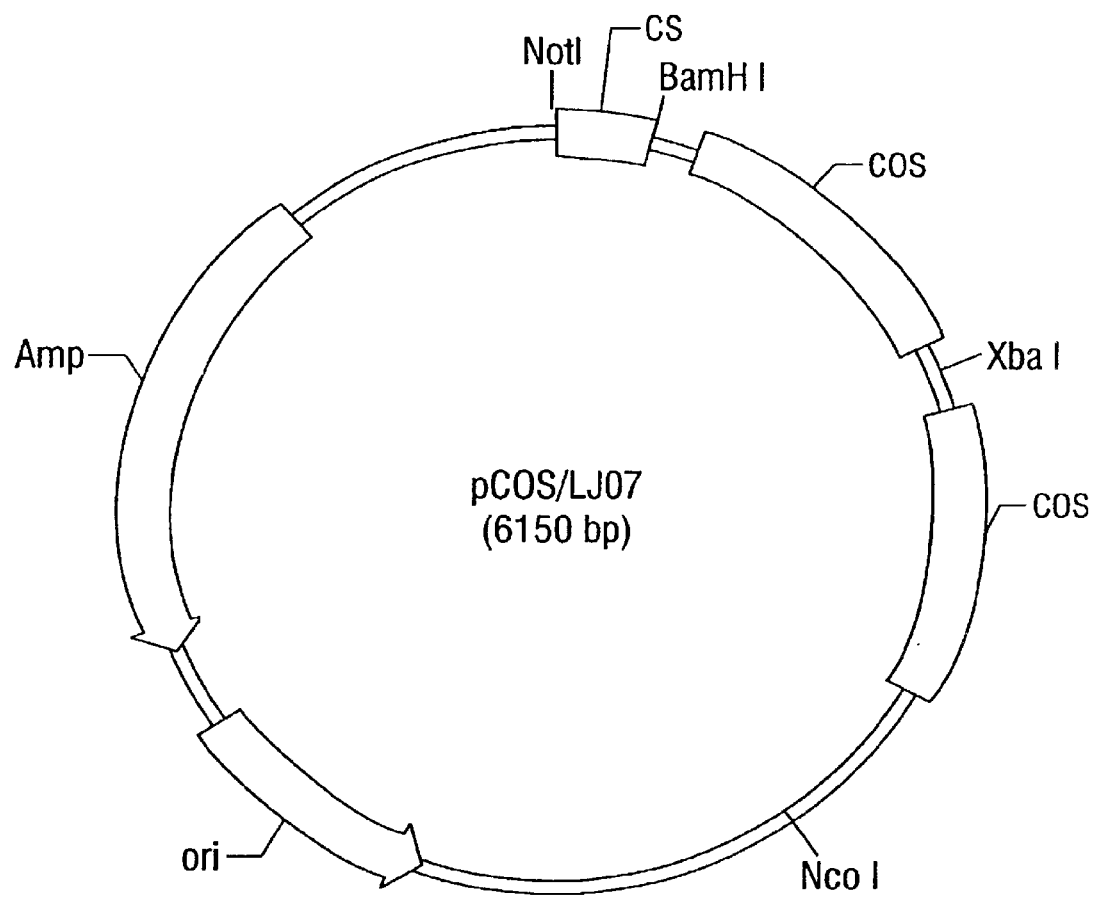
FIG. 6. Plasmid map of pCOS/LJ07.
Figure 7:
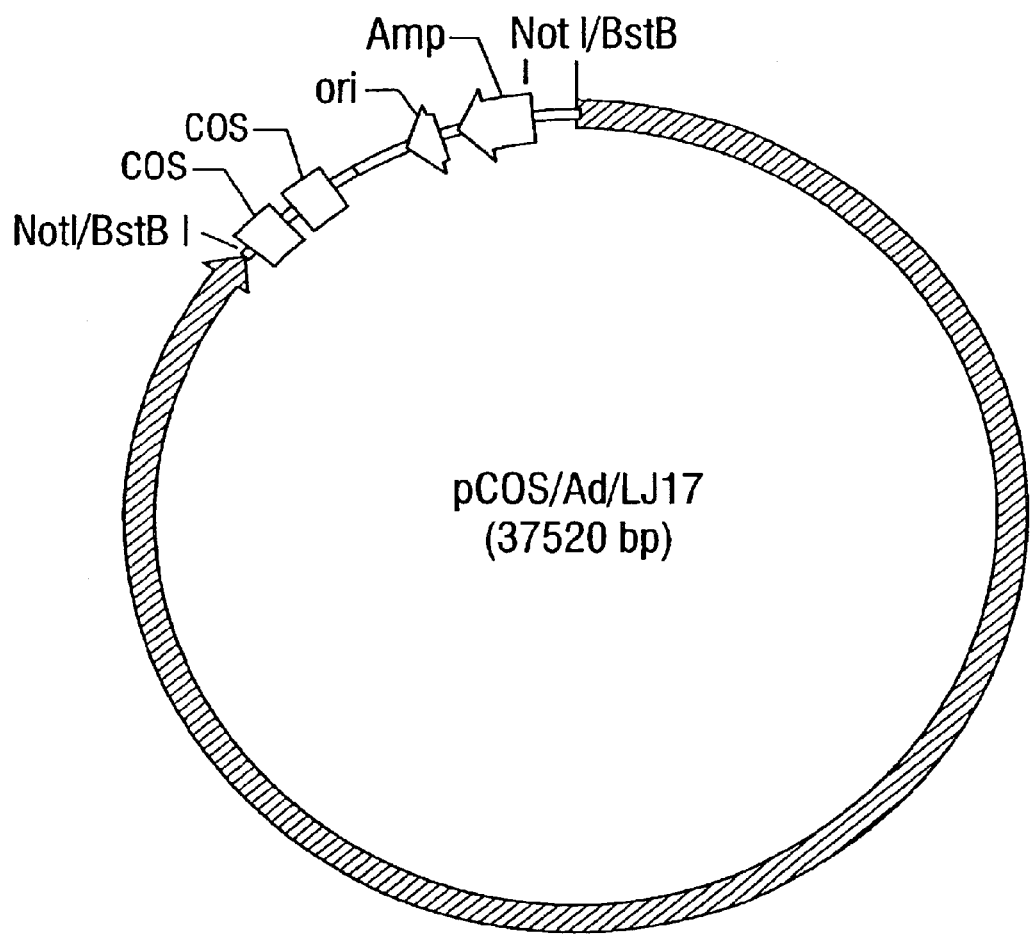
FIG. 7. Plasmid map of pCOS/Ad/LJ17.
Figure 8:
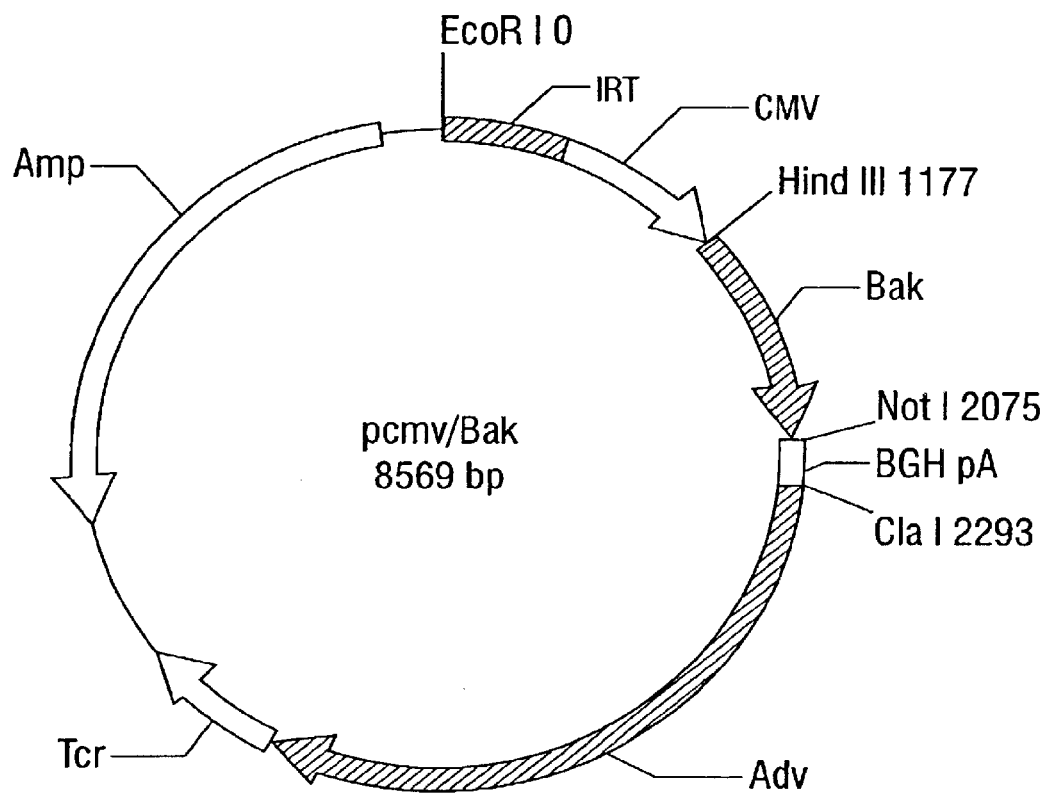
FIG. 8. Plasmid map of pCMV/Bak.
Figure 9:
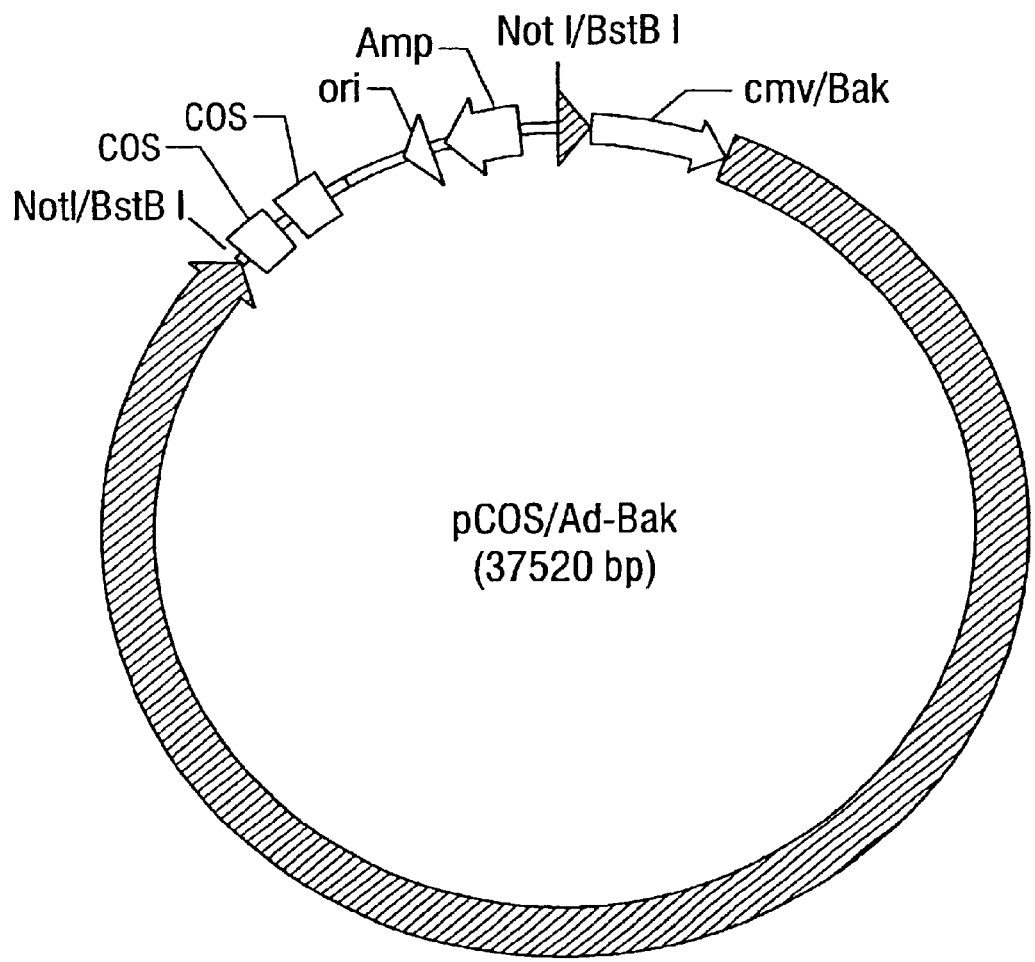
FIG. 9. Plasmid map of pCOS/Ad-Bak.
Figure 10:
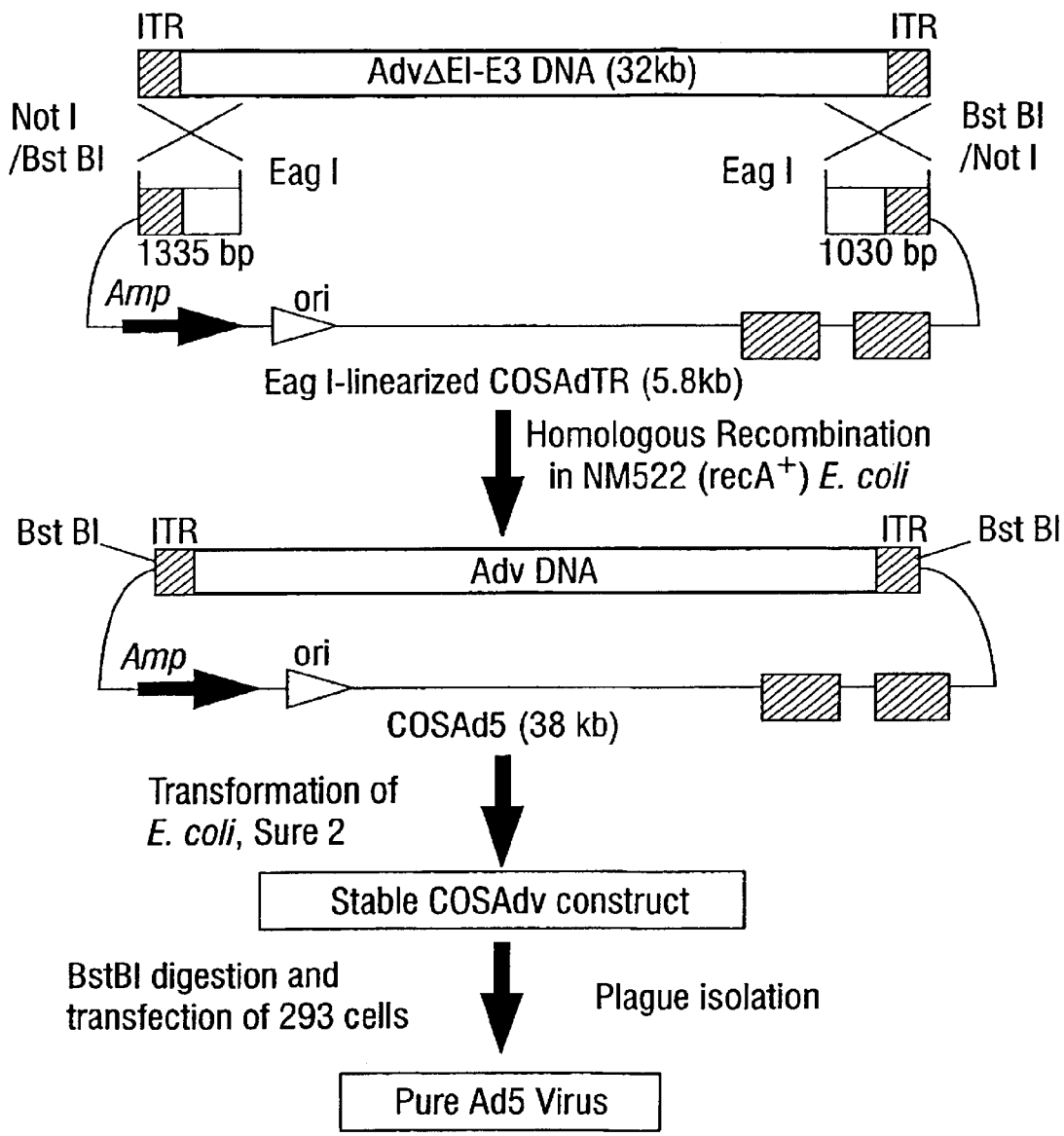
FIG. 10. Schematic of cloning adenovirus genome into cosmid.
Figure 11:
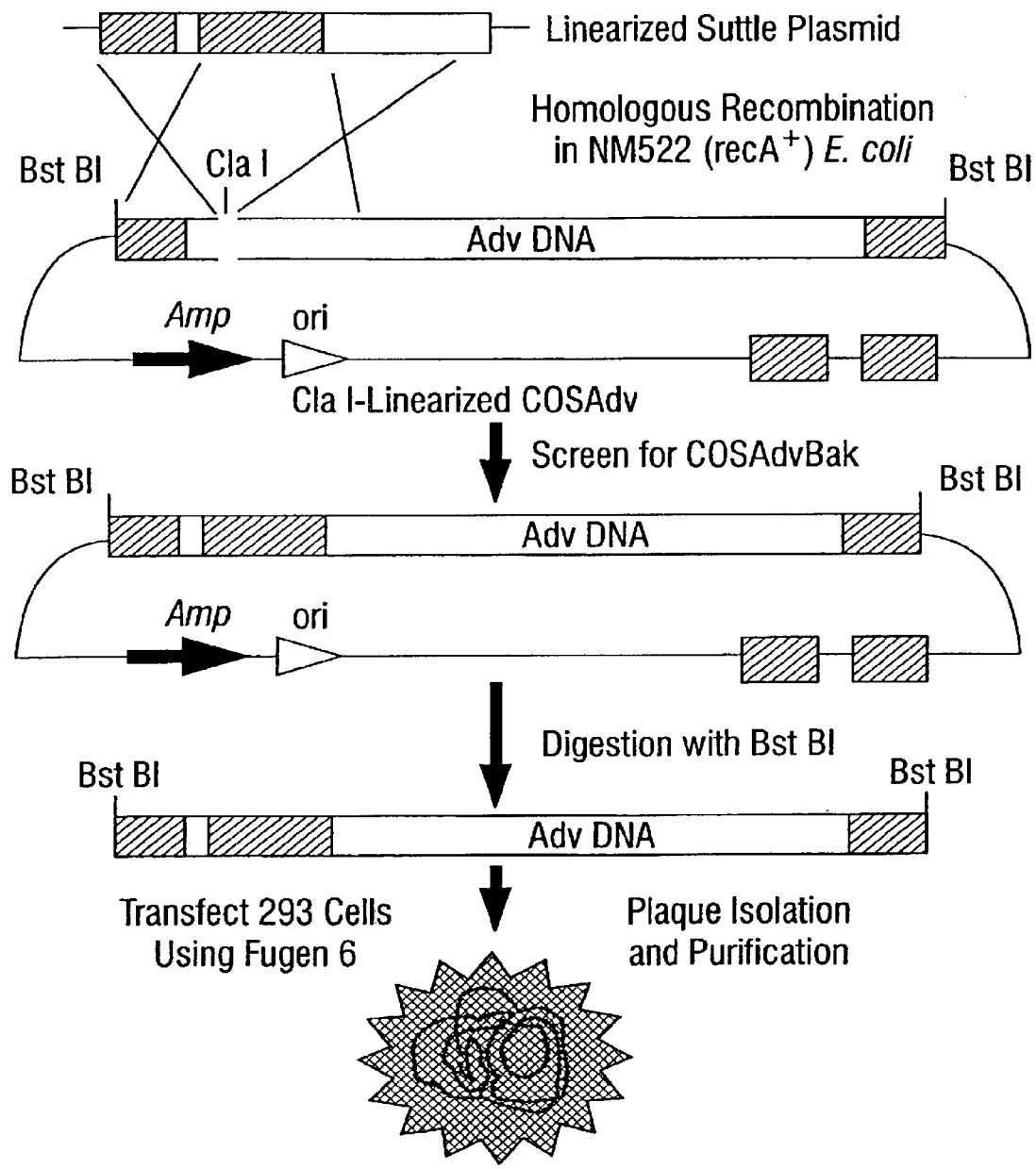
FIG. 11. Schematic of construction of recombinant adenovirus in E. coli.
Figure 12:
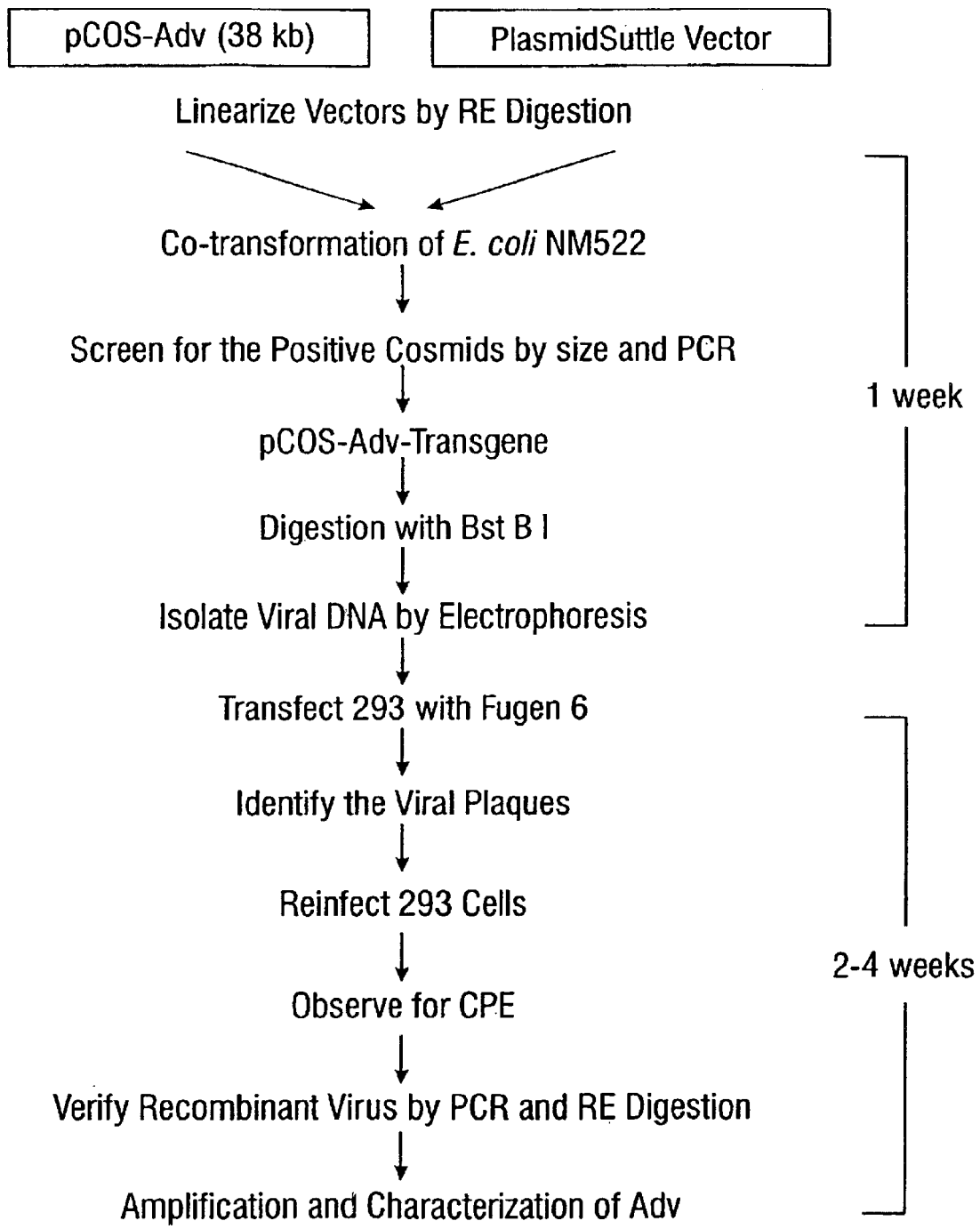
FIG. 12. Schematic of production of recombinant adenovirus.

The inventors used the Supercos vector (Stratagene, La Jolla, Calif.) as the base vector for this system (FIG. 5). Initially the SV40 origin of replication and the Neo gene were removed by restriction digestion to generate pCOS/LJ07 (FIG. 6). The cloning of the adenovirus genome in to the cosmid was attained by cotransfection of pCOS/LJ07 and pAdv-d1E1-d1E3-Gal4 (U.S. application No. 60/030,675, herein incorporated by reference) into NM522 E. coli cells to allow homologous recombination to occur. The resultant vector, pCOS/Ad/LJ17 (FIG. 7) was purified and the recombinant adenovirus then constructed by co-transfection of pCOS/Ad/LJ17 and a shuttle plasmid pCMV/Bak (FIG. 8) into NM522 E coli cells. The resultant vector pCOS/Ad-Bak (FIG. 9) contains the Bak gene under the control of the CMV IE promoter. Verification of the Ad-CMV-Bak construct by PCR™ confirmed that the proper insert was incorporated into the recombinant virus, and sequencing of the bak gene confirmed the sequence to be wild-type. Similar procedures were used to generate the wild-type bax gene adenovirus recombinant. Linearization of the vector containing the adenoviral genome, and then transfection into 293/GV16 cells results in the generation of recombinant vectors. FIG. 10, FIG. 11, and FIG. 12 outline these procedures.

Thus it is evident that the use of a system such as this is useful for the construction of adenoviral vectors, and that a wide variety of transgenes may be incorporated into the adenoviral genome using this or similar techniques. It will be appreciated that those of skill in the art may modify or improve such a system to produce better results or achieve greater efficiency.

EXAMPLE 5

Expression of the Bax Gene by Adenovirus Mediated Gene Co-Transfer

Materials and Methods

Cell lines. Human non-small cell lung cancer cell lines H1299 and A549 were cultured in RPMI 1640 and HAM/F12 medium, respectively, supplemented with 10% FBS and antibiotics. Human embryonic kidney 293 cells were maintained in Dulbecco's modified Eagle's medium (DMEM) containing 4.5 g/l of glucose with 10% FBS and antibiotics and used in the construction and amplification of adenovirus vectors.

Construction of recombinant adenovirus vectors. The construction of Ad/PGK-GV16, Ad/GT-Luc, and Ad/GT-LacZ as described by Fang et al. (1998). Ad/CMV-GFP was obtained from Fueyo et al (1998). Mutations found in the bax cDNA were corrected by combining two PCR products of the gene. The authenticity of the bax-α cDNA sequence was then confirmed by automatic DNA sequencing performed at M. D. Anderson Cancer Center's Core DNA Sequencing Facility. For construction of Ad/GT-Bax, the bax gene was first cloned downstream of the GT promoter to generate the shuttle plasmid pAd/GT-Bax. Then, the vector was constructed by cotransfecting 293 cells with a 35-kb cal fragment from Ad/p53 and pAd/GT-Bax (Zhang et al., 1993). The virus titers cited in this study were determined by optical absorbency at $A_{260}$ (one $A_{260}$ unit=$10^{12}$ viral particle/ml). Particle/plaque ratios usually fell between 30:1 and 100:1. All viral preparations were tested for $E1^+$adenovirus contamination by PCR (Fang et al., 1996) and for endotoxin contamination by assays with a third-generation pyrogen testing kit from BioWhittaker (Walkersville, Md.).

PCR analysis. Viral DNA was isolated from the supernatant of viruses expanded in 293 cells. A primer located in the bax gene was then used with a second primer located in the adenoviral backbone in PCR to identify recombinants via PCR. The plasmid pAd/GT-Bax was used as a positive control for Ad/GT-Bax. Primers used for detecting $E1^+$ adenovirus were the same as in Fang et al. (1996).

Transduction of target cells with adenoviral vectors. All cells were seeded on 100-mm dishes at a density of $2\times10^6$/dish 1 day prior to infection. H 1299 and A549 cells were infected at a total MOI of 900 and 1500, respectively. For coadministration of two vectors, the ratio of the first vector to second vector was 2:1. A preliminary study showed that such a ratio resulted in optimal transduction of H1299 cells. Cells were either harvested at 24 h and 48 h after infection for western blot analysis or morphological observation by Hoechst staining.

Western blot analysis. Cell samples were lysed or liver samples from the in vivo study were homogenized in a buffer consisting of 62.5 mM Tris, pH 6.8, 6 M urea, 10% glycerol, 2% sodium dodecyl sulfate (SDS), and 0.003% bromophenol blue. All samples were sonicated for 30 sec on ice before the subsequent analysis. Protein concentration was determined using BCA Protein Assay Reagent (Pierce, Rockford, Ill.). Fifty micrograms of protein was mixed with 5% 2-mercaptoethanol, boiled for 5 min, and then loaded onto a SDS-polyacrylamide gel. After electrophoresis, the proteins were transferred onto PROTRAN nitrocellulose membranes (Schleicher & Schuell, Keene, NH), which were then blocked for 1 h in PBS containing 10% milk. To detect various proteins, the membranes were probed overnight with primary antibodies against bax (N-20; Santa Cruz Biotechnology, Santa Cruz, Calif.), PARP($C_{2-10}$; PharMingen, San Diego, Calif.), caspase-3 (PharMingen), and β-actin (Amersham, Arlington Heights, Ill.) at concentrations recommended by the manufacturers. The membranes were washed 3 times and probed with horseradish peroxidase-conjugated, species-specific secondary antibodies (Amersham). Finally, bands were visualized using the ECL system (Amersham) according to the manufacturer's instructions and the density of each band was quantified using Optimas software (Media Cybernetics, Silver Spring, Md.).

Hoechst staining. Cells were seeded on 4-chamber slides at a density of $5\times10^4$/chamber 1 day prior to infection. Forty-eight hours after infection at the MOI described above, cells were fixed with 4% glutaraldehyde and stained with 100 μg/ml Hoechst 33342 (Sigma, St. Louis, Mo.) for 15 min, followed by a gentle washing with PBS. Photographs were taken under a fluorescent microscope.

Animal experiments. Balb/c mice 6–8 weeks old were purchased from the National Cancer Institute (Frederick, Md.). Prior to injection, Ad/GT-Bax (or Ad/GT-LacZ) was mixed with Ad/PGK-GV16 (or Ad/CMV-GFP) at a ratio of 1:2. A total of $6\times10^{10}$ particles/mouse were injected into the tail vein in a volume of 100 μl. Mice were killed 1 day after injection. Their livers were then harvested and frozen at −80° C. for later western blot analysis or fixed in 10% buffered formalin for later histochemical analysis. Sectioning and staining was with hematoxylin and eosin.

Results

Construction of Adenoviruses Expressing Bax.

Figure 13:
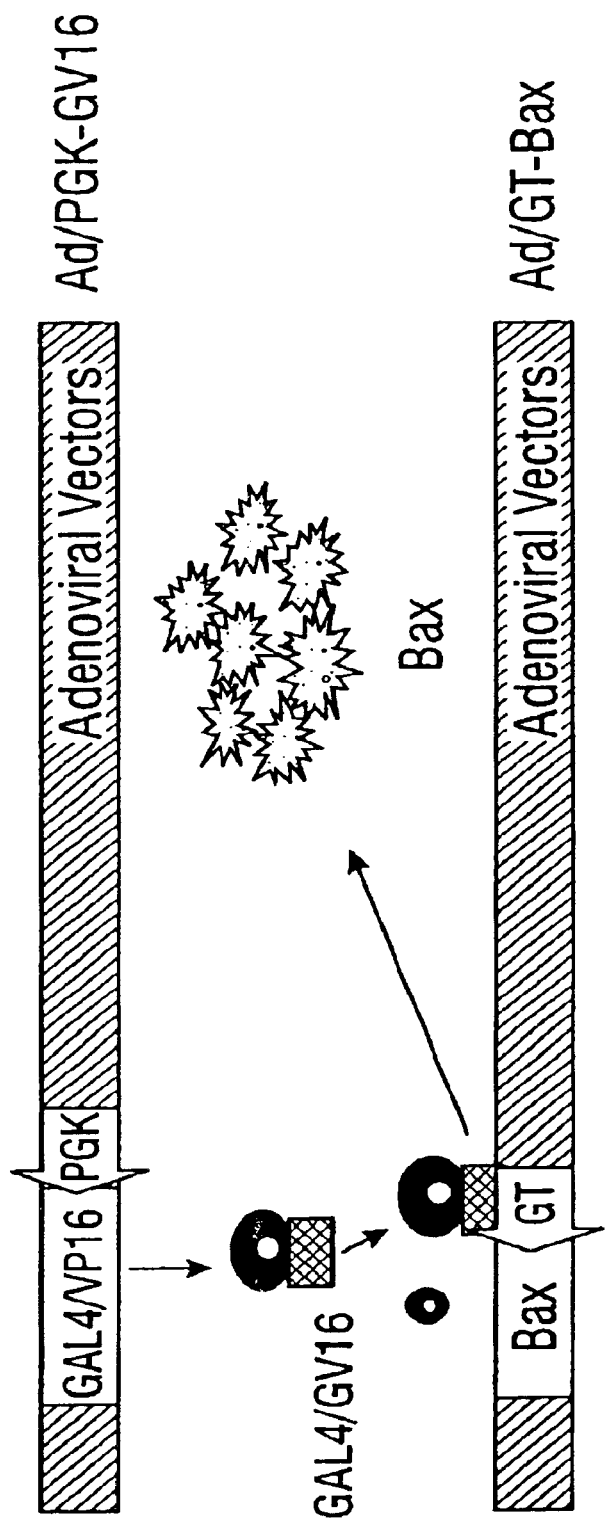
FIG. 13. Schematic of adenovirus-mediated gene co-transfer. The expression cassettes for the transgene (bax)

Shuttle plasmids were constructed in which bax cDNA was driven by GT. Recombinant viral vectors were obtained after a single transfection of 293 cells with pAd/GT-Bax plus a 35-kb ClaI fragment from Ad/p53 and identified by polymerase chain reaction (PCR) analysis with viral DNA. The functionality of Ad/GT-Bax was documented by the coadministration of Ad/GT-Bax and Ad/PGK-GV16 to the cultured human lung carcinoma cell line H1299 (FIG. 13). Virus from a single plaque was expanded in 293 cells and twice purified by ultracentrifugation on a cesium chloride gradient. The vector titer determined by optical absorbency at $A_{260}$ was $3.3 \times 10^{12}$ viral particles/ml, equivalent to that of the other E1-deleted vectors, such as Ad/CMV-GFP and Ad/CMV-LacZ. The total yield for Ad/GT-Bax also was the same as for the other E1-deleted vectors produced in our laboratory, about $1.5 \times 10^4$ particles/cell. The vector preparation was free of E1+ adenovirus and endotoxin.

Induction of Bax Expression After Adenovirus-mediated Gene Codelivery.

To demonstrate induction of the bax gene in cultured mammalian cells by adenovirus-mediated gene co-transfer, human lung carcinoma cell lines H1299 and A549 were infected with Ad/GT-Bax and Ad/PGK-GV16 at a vector ratio of 2:1 and at a total multiplicity of infection (MOI) of 900 and 1500, respectively. A preliminary experiment showed that this ratio gave optimal transduction efficiency in H1299 cells treated at a fixed total MOI. Cells treated with PBS or infected either with Ad/GT-Bax plus Ad/CMV-GFP or with Ad/GT-LacZ plus Ad/PGK-GV 16 at the same vector ratio and MOIs were used as controls. Cells were harvested 24 h after the treatment and their lysates subjected to western blot analysis. Levels of β-actin in the same western blots were also analyzed and used to ensure equal protein loading in all lanes. Though background levels of the bax protein expression differed between H1299 and A549 cells and though the treatment with control vectors did not increase those background levels, a strong induction of bax expression was detected in both cell lines when they were treated with Ad/GT-Bax plus Ad/PGK-GV16. The induction was seen to be 67.2- and 8.7-fold in H1299 and A549 cells, respectively, when the densities of the bax-specific bands were quantified and normalized to the density of β-actin bands.

Triggering Apoptosis By Induction of the Bax Expression.

Overexpression of the bax gene has been demonstrated to induce the release of Cyt c from mitochondria (Jurgensmeier et al., 1998; Pastorino et al., 1998; Rosse et al., 1998) which leads to cleavage first of caspase-3/CPP32 followed by cleavage of poly(ADP ribose)polymerase (PARP) (Tewari et al., 1995). To demonstrate the induction of bax expression and apoptosis by adenovirus-mediated gene codelivery in H1299 and A549 cells, samples of the same cell lysate from the above-mentioned experiments were subjected to western blot analysis of the cleavage of caspase-3 and PARP. The cleavage of caspase-3 into a 17-kD fragment and PARP into a 85-kD fragment was detected in cells treated with Ad/GT-Bax plus Ad/PGK-GV16 but not in cells from any other experimental groups. To further document the apoptosis in these cells, H1299 and A549 cells were treated with various vectors as mentioned above and observed for cytopathology and morphology changes at 48 h after treatment. Over 80% of the cells treated with Ad/GT-Bax plus Ad/PGK-GV16 showed signs of cytopatholgy, and became rounded and detached, whereas the cells in all other treated groups remained in monolayers with normal morphology. Nuclear fragmentation, a hallmark of cell apoptosis, was detected only in cells treated with Ad/GT-Bax plus Ad/PGK-GV16 (FIG. 14), indicating that bax expression by this system did activate not only the caspase cascade, but ultimately extensive apoptosis in these human lung cancer cell lines.

Induction of Bax Gene Expression In Vivo.

To demonstrate bax gene expression by adenovirus-mediated gene codelivery in vivo, adult Balb/c mice were infused via their tail veins with PBS, Ad/GT-Bax plus Ad/CMV-GFP, Ad/GT-Bax plus Ad/PGK-GV16, or Ad/GT-LacZ plus Ad/PGK-GV16 at a total vector dose of $6 \times 10^{10}$ particles/mouse and a vector ratio of 2:1. Mice were then killed at 24 h after treatment, after which liver samples were harvested for western blot analysis and histopathological examination. Western blot analysis showed a 14-fold increase in bax protein levels in animals treated with Ad/GT-Bax plus Ad/PGK-GV16, but only background level in all other treatment groups. These results clearly demonstrated that the Ad/GT-Bax plus Ad/PGK-GV16 strictly regulated bax expression by expressing GAL4/VP 16 protein even in vivo. Expression of the bax gene also induced typical apoptosis in normal liver cells, as revealed by nuclear fragmentation and condensation in hematoxylin- and eosin-stained liver sections (FIG. 15). Together, these results demonstrate that adenovirus-mediated gene co-transfer can produce sufficient bax expression and induce apoptosis in vivo.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,359,046
EPO 0273085
Apte, Mattei, Olsen, "Mapping of the human BAX gene to chromosome 19q13.3-q13.4 and isolation of a novel alternatively spliced transcript, BAX delta," *Genomics* 26:592–594, 1995.
Arai, Gordon, Nabel, and Nabel, "Gene transfer of Fas ligand induces tumor regression in vivo," *Proc. Natl. Acad. Sci. USA* 94:13862–13867, 1997.
Arap et al., *Cancer Res.,* 55:1351–1354, 1995.
Arcone, et al., *Nucl. Acids Res.,* 16(8): 3195–3207, 1988.
Atkin, *Cytogenetic,* 21:279, 1986.
Baichwal and Sugden, In: *Gene Transfer,* Kucherlapati R, ed., New York, Plenum Press, pp. 117–148, 1986.
Bakhshi et al., *Cell,* 41:899, 1985.
Bargou et al., *Int. J Cancer,* 60:854, 1995.
Bartlett et al., *Proc. Natl Acad. Sci. USA,* 93:8852–8857, 1996.
Bedzyk et al., *J. Biol. Chem.,* 265:18615, 1990
Benvenisty and Neshif, *Proc. Nat. Acad. Sci. USA,* 83:9551–9555, 1986.
Binder, Marx, Binder, Schauer, Hiddemann, "Expression of Bax in relation to Bcl-2 and other predictive parameters in breast cancer," *Ann. Oncol.* 7:129–133, 1996.

Bishop, *Cell*, 64:235, 1991.
Boise et al., *Cell*, 74:597, 1993.
Boyd et al., *Oncogene*, 11:1921, 1995.
Briand, Chobert, Gantier, Declerck, Tran, Leonil, Molle, Haertle, "Impact of the lysine-1888 and aspartic acid-189 inversion on activity of trypsin," *FEBS Lett.*, 442(1):43–47, 1999.
Buschmann, Kuczius, Bodemer, Groschup, "Cellular prion proteins of mammalian species display an intrinsic partial proteinase K resistance," *Biochem. Biophys. Res. Commun.*, 253(3):693–702, 1998.
Bussemakers et al., *Cancer Res.*, 52:2916–2922, 1992.
Caldas et al., *Nat. Genet.*, 8:27–32, 1994.
Carter and Flotte, *Ann. N.Y. Acad. Sci.*, 770:79–90, 1995.
Casey et al., *Oncogene*, 6:1791–1797, 1991.
Chandler et al., *Human Pathol.*, 25:789, 1994.
Chatterjee, et al., *Ann. N.Y. Acad. Sci.*, 770:79–90, 1995.
Chaudhary et al. *Proc. Natl. Acad. Sci.*, 87:9491, 1990
Chen and Faller, *J. Biol. Chem.*, 271:2376, 1996.
Chen and Okayama, *Mol. Cell Biol.*, 7:2745–2752, 1987.
Cheng et al., *Nature*, 379:554, 1996.
Cheng et al., *Cancer Res.*, 54:5547–5551, 1994.
Cheung et al., *J. Biol. Chem.*, 268:6139–6146, 1993.
Chinnaiyan et al., *Science*, 275:1122, 1997.
Chiou et al., *Mol. Cell. Biol.*, 14:2556, 1994.
Chittenden et al., *Nature*, 374:733, 1995.
Choi and Boise, *Eur. J. Immunol.*, 25:1352, 1995.
Choi et al., *Oncogene*, 11:1693, 1995.
Choi, Bang, Kim, Yu, "Extremely thermostable serine-type protease from Aquifex pyrophilus. Molecular cloning, expression, and characterization," *J. Biol. Chem.*, 274(2):881–888, 1999.
Cleary and Sklar, *Proc. Natl. Acad. Sci. USA*, 82:7439, 1985.
Cleary et al., *Cell*, 47:19, 1986.
Coffin, In: *Virology*, ed., New York: Raven Press, pp. 1437–1500, 1990.
Coll, Negoescu, Louis, Sachs, Tenaud, Girardot, Demeinex, Brambilla, Brambilla, Favrot, "Antitumor activity of bax and p53 naked gene transfer in lung cancer: in vitro and in vivo analysis," *Hum. Gene Ther.* 9:2063–2074, 1998.
Coupar et al., *Gene*, 68:1–10, 1988.
Craig et al., *Genomics*, 23:457, 1994.
D'Sa-Eipper et al., *Cancer Res.*, 56:3879, 1996.
Dalla-Favera et al., Croce, *Proc. Natl. Acad. Sci. USA*, 79:7824, 1982.
Dani, et al., *J. Biol. Chem.*, 264:10119–10125, 1989.
dejong et al., *Curr. Top. Microbiol. Immunol.*, 182:287, 1992.
Dubensky et al., *Proc. Nat. Acad. Sci. USA*, 81:7529–7533, 1984.
Edelman and Crossin, *Annu. Rev. Biochem.*, 60:155–190, 1991.
Edelman, *Annu. Rev. Biochem.*, 54:135–169, 1985.
Fang, Ji, Bouvet, Roth, "Evaluation of GAL4/TATA in vivo. Induction of transgene expression by adenovirally mediated gene codelivery," *J. Biol. Chem.* 273:4972–4975, 1998.
Fang, Wang, Gordon, Bellinger, Read, Brinkhous, Woo, Eisensmith, "Lack of persistence of E1- recombinant adenoviral vectors containing a temperature-sensitive E2A mutation in immunocompetent mice and hemophilia B dogs," *Gene Ther.* 3:217–222, 1996.
Farrow et al., *Nature*, 374:731, 1995.
Fechheimer et al., *Proc. Natl. Acad. Sci. USA*, 84:8463–8467, 1987.
Ferkol et al., *FASEB J.*, 7:1081–1091, 1993.
Ferrari et al., *J. Virol.*, 70:3227–3234, 1996.
Fisher et al., *J. Virol.*, 70:520–532, 1996.
Fisher, "Apoptosis in cancer therapy: crossing the threshold," *Cell* 78:539–542, 1994.
Flotte et al., *Proc. Natl. Acad. Sci. USA*, 90:10613–10617, 1993.
Fraley et al., *Proc. Natl. Acad. Sci. USA*, 76:3348–3352, 1979.
Fraser and Evan, *Cell*, 85:781, 1996.
Friedmann, "Progress toward human gene therapy," *Science*, 244:1275–1281', 1989.
Frixen et al., *J. Cell Biol.*, 113:173–185, 1991.
Fueyo, Gomez-Manzano, Yung, Liu, Alemany, McDonnell, Shi, Rao, Levin, Kyritsis, "Overexpression of E2F-1 in glioma triggers apoptosis and suppresses tumor growth in vitro and in vivo," *Nat. Med.* 4:685–690, 1998.
Fujiwara et al., *Cancer Res.*, 54.2287–2291, 1994.
Gawerky et al., *Proc. Natl. Acad. Sci. USA*, 85:8548, 1988.
Gendler et al., *Int. J. Cancer*, 45:431, 1990.
Ghosh and Bachhawat, In: *Liver diseases, targeted diagnosis and therapy using specific receptors and ligands*, (Wu G, Wu C ed.), New York: Marcel Dekker, pp. 87–104, 1991.
Giancotti and Ruoslahti, *Cell*, 60:849–859, 1990.
Gibson et al., *Oncogene*, 13:665, 1996.
Gonzalez-Garcia et al., *Development*, 120:3033, 1994.
Goodman et al., *Blood*, 84:1492–1500, 1994.
Gopal, *Mol. Cell Biol.*, 5:1188–1190, 1985.
Gorczyca et al., *Int'l J Oncol.*, 1:639–648, 1992.
Gossen and Bujard, *Proc. Natl. Acad. Sci. USA*, 89:5547–5551, 1992.
Gossen et al., *Science*, 268:1766–1769, 1995.
Gottschalk et al., *Proc. Natl. Acad. Sci. USA*, 91:7350, 1994.
Graham and Prevec, In: *Methods in Molecular Biology: Gene Transfer and Expression Protocols* 7, E. J. Murray (ed.), Clifton, N.J., Humana Press, pp. 205–225. 1991.
Graham and Van Der Eb, *Virology*, 52:456467, 1973.
Grandien and Wahren, "A review of the current research on prions. The evidence suggests the possibility of transmission of the mad cow disease to human," *Lakartidningen*, 95(48):5499–5500, 5503–5505, 1998.
Gratiot-Deans et al., *J. Immunol.*, 151:83, 1993.
Hanada et al., *J. Biol. Chem.*, 270:11962, 1995.
Hay et al., *J. Mol. Biol.*, 175:493–510, 1984.
Hearing and Shenk, *J. Mol. Biol.* 167:809–822, 1983.
Hearing et al., *J. Virol.*, 67:2555–2558, 1987.
Hill, Butterworth, Joiner, Jackson, Rossor, Thomas, Frosh, Tolley, Bell, Spencer, King, Al-Sarraj, Ironside, Lantos, Collinge, "Investigation of variant Creutzfeldt-Jakob disease adn other human prion diseases with tonsil biopsy samples," *Lancet*, 353(9148):183–189, 1999.
Hockenbery et al., *Nature*, 348:334, 1990.
Hockenbery et al., *Proc. Natl. Acad. Sci. USA*, 88:6961, 1991.
Hollstein et al., *Science*, 253:49–53, 1991.
Hunt et al., *Proc. Natl. Acad. Sci. USA*, 83:3786–3790, 1986.
Hussussian et al., *Nature Genetics*, 15–21, 1994.
Inohara et al, *EMBO J.*, 16:1686, 1997.
Joki, et al., *Human Gene Ther.*, 6:1507–1513, 1995.
Jurgensmeier, Xie, Deveraux, Ellerby, Bredesen, Reed, "Bax directly induces release of cytochrome c from isolated mitochondria," *Proc. Natl. Acad. Sci. USA* 95:4997–5002, 1998.
Kageyama, et al., *J. Biol. Chem.*, 262(5):2345–2351, 1987.
Kamada et al., *Cancer Res.*, 55:354, 1995.
Kamb et al., *Nature Genetics*, 8:22–26, 1994.
Kamb et al., *Science*, 2674:436–440, 1994.
Kaneda et al., *Science*, 243:375–378, 1989.

Kaplitt et al., *Arm. Thor. Surg.*, 62:1669–1676, 1996.
Kaplitt et al., *Nat. Genet.*, 8:148–153, 1994.
Kapranos, Karaiosifidi, Valavanis, Kouri, Vasilaros, "Prognostic significance of apoptosis related proteins Bcl-2 and Bax in node-negative breast cancer patients," *Anticancer Res.* 17:2499–2505, 1997.
Karlsson et al., *EMBO J.*, 5:2377–2385, 1986.
Karsan et al., *J. Biol. Chem.*, 271:27201, 1996.
Kato et al, *J. Biol. Chem.*, 266:3361–3364, 1991.
Kenny et al., *Oncogene*, 14:997, 1997.
Kerr et al., *Br. J. Cancer*, 26:239, 1972.
Kessler et al., *Proc. Natl. Acad. Sci. USA*, 93:14082–14087, 1996.
Kiefer et al., *Nature*, 374:736, 1995.
Klein et al., *Nature*, 327:70–73, 1987.
Knudsonn et al, *Science*, 270:96, 1995.
Koeberl et al., *Proc. Natl. Acad. Sci. USA*, 94:1426–1431, 1997.
Korhonen, et al., Blood, Vol. 86, No. 5, Sep. 1, 1995: pp 1828–1835.
Korsmeyer et al., *Sem. Cancer Biol.*, 4:327, 1993.
Kozopas et al., *Proc. Natl. Acad. Sci. USA*, 90:3516, 1993.
Krajewski et al., *Am. J. Path.*, 145:515, 1994b.
Krajewski et al., *Am. J Path.*, 146:1309, 1995b.
Krajewski et al., *Cancer Res,.* 56:2849–2855, 1996.
Krajewski, Blomqvist, Franssila, Krajewska, Wasenius, Niskanen, Nordling, Reed, "Reduced expression of proapoptotic gene BAX is associated with poor response rates to combination chemotherapy and shorter survival in women with metastatic breast adenocarcinoma," *Cancer Res.* 55:4471–4478, 1995a.
Krajewski, Krajewska, Shabaik, Miyashita, Wang, Reed, "Immunohistochemical determination of in vivo distribution of Bax, a dominant inhibitor of Bcl-2," *Am J. Pathol.*, 145:1323–1336, 1994a.
Lam et al., *Proc. Natl. Acad. Sci. USA*, 91:6569, 1994.
Langdon et al., *Cell*, 47:11, 1986.
Larregina, Morelli, Dewey, Castro, Fontana, Lowenstein, "FasL induces Fas/Apo 1-mediated apoptosis in human embryonic kidney 293 cells routinely used to generate E1-deleted adenoviral vectors," *Gene Ther.* 5:563–568, 1998.
LeBrun et al., *Am. J. Path.*, 142:743, 1993.
Levrero et al., *Gene*, 101:195–202, 1991.
Lin and Guidotti, *J. Biol. Chem.*, 264:14408–14414, 1989.
Lin et al., *J. Immunol.*, 151:1979, 1993.
Lomo et al., *Cancer Res.*, 56:40, 1996.
Lotem and Sachs, *Cell Growth Diff.*, 6:647, 1995.
Lu et al., *J Pathol.*, 169:431, 1993.
Lucas et al., *Oncol. Res.*, 6:139, 1994.
Macejaki and Sarnow, *Nature*, 353:90–94, 1991.
Manalov and Manolova, *Nature*, 237:33, 1972.
Mann et al., *Cell*, 33:153–159, 1983.
Marcelli, Cunningham, Walkup, He, Sturgis, Kagan, Mannucci, Nicoletti, Teng, Denner, "Signaling pathway activated during apoptosis of the prostate cancer cell line LNCaP: overexpression of caspase-7 as a new gene therapy strategy for prostate cancer," *Cancer Res.*, 59(2):382–390, 1999.
Marin et al., *Oncogene*, 11:2259, 1996.
Marin et al., *Oncogene*, 9:3107, 1994.
Matsura et al., *Brit. J Cancer*, 66:1122–1130, 1992.
McCown et al., *Brain Res.*, 713:99–107, 1996.
McDonnell and Korsmeyer, *Nature*, 349:254, 1991.
McDonnell et al., *Cell*, 57:79, 1989.
McDonnell et al., *J. Urology*, 157:569, 1997.
McDonnell et al., *Mol. Cell. Biol.*, 10:1901, 1990.
McDonnell, et al., *Cancer Res.*, 52:6940, 1992.
McDonnell, et al., *Mol. Carcinogen.*, 8:209, 1993a.
McDonnell, et al., *Transgene*, 1:47, 1993b.
Meijerink, Smetsers, Sloetjes, Lindersi, Mensink, "Bax mutations in cell lines derived from hematological malignancies," *Leukemia* 9:1828–1832, 1995.
Merchant et al., *Oncogene*, 13:2631–2637, 1996.
Merino et al, *EMBO J.*, 13:683, 1994.
Minn et al., *Nature*, 385:353, 1997.
Miyashita and Reed, *Cell*, 80:293, 1995.
Miyashita et al., *Cancer Res.*, 54:3131–3135, 1994a.
Miyashita et al., *Cell*, 80:293–299, 1995.
Miyashita et al., *Oncogene*, 9:1799–1805, 1994b.
Mizukami et al., *Virology*, 217:124–130, 1996.
Mori et al., *Cancer Res.*, 54:3396–3397, 1994.
Moss et al., *Biochem. Biophys. Res. Comm.*, 223:199, 1996.
Motoyama et al., *Science*, 267:1506, 1995.
Muchmore et al., *Nature*, 381:335, 1996.
Nakayama et al., *Proc. Natl. Acad. Sci. USA*, 91:3700, 1994.
Nicolas and Rubenstein, In: *Vectors: A survey of molecular cloning vectors and their uses*, Rodriguez and Denhardt (eds.), Stoneham: Butterworth, pp. 493–513, 1988.
Nicolau and Sene, *Biochim. Biophys. Acta*, 721:185–190, 1982.
Nicolau et al., *Methods Enzymol.*, 149:157–176, 1987.
Nishikura et al., *Proc. Natl. Acad. Sci. USA*, 80:4822, 1983.
Nobri et al., *Nature*, 368:753–756, 1995.
Novack and Korsmeyer, *Am. J. Path.*, 145:61, 1994.
Nowell and Hungerford, *Science*, 132:1497, 1960.
Nunez et al., *Nature*, 353:71, 1991.
Obrink, *BioEssays*, 13:227–233, 1991.
Odin and Obrink, *Exp. Cell Res.*, 171:1–15, 1987.
Okamoto et al., *Proc. Nat'l Acad. Sci. USA*, 91:11045–11049, 1994.
Okuyama, Fujino, Li, Funeshima, Kosuga, Saito, Suzuki, Yamada, "Efficient Fas-Ligand gene expression in rodent liver after intravenous injection of a recombinant adenovirus by the use of a Cre-mediated switching system," *Gene Ther.* 5:1047–1053, 1998.
Olivierio, et al., *EMBO J.*, 6(7):1905–1912, 1987.
Olsen et al., *J. Virol.*, 70:663, 1996.
Oltvai, Milliman, Korsmeyer, "Bcl-2 heterodimerizes in vivo with a conserved homolog, Bax, that accelerates programmed cell death," *Cell* 74:609–619, 1993.
Orlow et al., *Cancer Res.*, 54:2848–2851, 1994.
Orth and Dixit, *J. Biol. Chem.*, 272:8841, 1997.
Ouyang, Furukawa, Abe, Kato, Horii, "The BAX gene, the promoter of apoptosis, is mutated in genetically unstable cancers of the colorectum, stomach, and endometrium," *Clin. Cancer Res.* 4:1071–1074, 1998.
Pape and Kim, *Mol. Cell. Biol.*, 974–982, 1989.
Park et al., *Blood*, 86:868, 1995.
Paskind et al, *Virology*, 67:242–248, 1975.
Pastorino, Chen, Tafani, Snyder, Farber, "The overexpression of Bax produces cell death upon induction of the mitochondrial permeability transition," *J. Biol. Chem.* 273:7770–7775, 1998.
Pelletier and Sonenberg, *Nature*, 334:320–325, 1988.
Perales et al., *Proc. Natl. Acad. Sci.* 91:4086–4090, 1994.
Ping et al., *Microcirculation*, 3:225–228, 1996.
Poli and Cortese, *Proc. Natl. Acad. Sci. USA*, 86:8202–8206, 1989.
Potter et al., *Proc. Nat. Acad. Sci. USA*, 81:7161–7165, 1984.
Prowse and Baumann, *Mol Cell Biol*, 8(1):42–51, 1988.
Radler et al, *Science*, 275:810–814, 1997.
Rampino et al., *Science*, 275:967, 1997.
Reed et al, *Adv. Exp. Med. Biol.*, 406:99, 1996.
Renan, *Radiother. Oncol.*, 19:197–218, 1990.
Rich et al., *Hum. Gene Ther.*, 4:461–476, 1993.
Ridgeway, In: *Vectors: A survey of molecular cloning vectors and their uses*, Rodriguez RL, Denhardt DT, ed., Stoneham:Butterworth,pp. 467–492, 1988.
Rippe et al., *Mol. Cell Biol.*, 10:689–695, 1990.
Ron, et al., *Mol. Cell. Biol.*, 2887–2895, 1991.
Rosse, Olivier, Monney, Rager, Conus, Fellay, Jansen, Bomer, "Bcl-2 prolongs cell survival after Bax-induced release of cytochrome c," *Nature* 391:496–499, 1998.
Rouayrenc et al., *Acad. Sci. III*, 318:5537, 1995.
Roux et al., *Proc. Natl Acad. Sci. USA*, 86:9079–9083, 1989.
Rowley, *Nature*, 243:290, 1973.
Sakakura, Sweeney, Shirahama, Igarashi, Hakomori, Nakatani, Tsujimoto, Imanishi, Ohgaki, Ohyama, Yamazaki, Hagiwara, Yamaguchi, Sawai, Takahashi, "Overexpression of bax sensitizes human breast cancer MCF-7 cells to radiation-induced apoptosis," *Int. J Cancer* 67:101–105, 1996.
Sakakura, Sweeney, Shirahama, Igarashi, Hakomori, Tsujimoto, Imanishi, Ogaki, Ohyama, Yamazaki, Hagiwara, Yamaguchi, Sawai, Takahashi, "Overexpression of bax sensitizes breast cancer MCF-7 cells to cisplatin and etoposide," *Surg. Today* 27:676–679, 1997a.
Sakakura, Sweeney, Shirahama, Igarashi, Hakomori, Tsujimoto, Imanishi, Ohgaki, Yamazaki, Hagiwara, Sawai, Yamaguchi, Takahashi, "Overexpression of bax enhances the radiation sensitivity in human breast cancer cells," *Surg. Today* 27:90–93, 1997b.
Samulski et al., *J. Virol.*, 61(10):3096–3101, 1987.
Sato et al, *Proc. Natl. Acad. Sci. USA*, 91:9238, 1994.
Sattler et al., *Science*, 275:983, 1997.
Sedlak et al, *Proc. Natl. Acad. Sci. USA*, 92:7834, 1995.
Serrano et al, *Nature*, 366:704–707, 1993.
Serrano et al, *Science*, 267:249–252, 1995.
Seto et al, *EMBO J.*, 7:123, 1988.
Shibasaki et al., *Nature*, 386L:728, 1997.
Shinoura, Ohashi, Yoshida, Asai, Kirinoi, Saito, Hamada, "Construction, propagation, and titer estimation of recombinant adenoviruses carrying proapoptotic genes," *Hum. Gene Ther.* 9:2683–2689, 1998.
Shtivelman et al, *Nature*, 315:550, 1985.
Silvstrini et al, *J. Natl Cancer Inst.*, 86:499, 1994.
Simonian et al, *J. Biol. Chem.*, 271:32073, 1996.
Speigelman, et al., *J. Biol. Chem.*, 264(3), 1811–1815, 1989.
Strobel, Kraeft, Chen, Cannistra, "BAX expression is associated with enhanced intracellular accumulation of paclitaxel: a novel role for BAX during chemotherapy-induced cell death," *Cancer Res.* 58:47764781, 1998.
Strobel, Swanson, Korsmeyer, Cannistra, "BAX enhances paclitaxel-induced apoptosis through a p53-independent pathway," *Proc. Natl. Acad. Sci. USA* 93:14094–14099, 1996.
Sundd, Kundu, Pal, Medicherla, "Purification and characterization of a highly stable cysteine protease from the latex of Ervatamia coronaria," *Biosci. Biotechnol Biochem.*, 62(10):1947–1955, 1998.
Tai, Lee, Niloff, Weisman, Strobel, Cannistra, "BAX protein expression and clinical outcome in epithelial ovarian cancer," *J. Clin. Oncol.* 16:3211, 1998.
Takahashi et al., *Cancer Res.*, 52:734–736, 1992.
Tanaka et al., *J. Biol. Chem.*, 268:10920, 1993.
Taub et al., *Cell*, 36:339, 1984.
Temin, In: *Gene Transfer*, Kucherlapati (ed.), New York: Plenum Press, pp. 149–188, 1986.
Testa, *Cell Growth Diff.*, 1:97, 1990.
Tewari, Quan, K, Desnoyers, Zeng, Beidler, Poirier, Salvesen, Dixit, "Yama/CPP32 beta, a mammalian homolog of CED-3, is a CrmA-inhibitable protease that cleaves the death substrate poly (ADP-ribose) polymerase," *Cell* 81:801–809, 1995.
Thompson, "Apoptosis in the pathogenesis and treatment of disease," *Science* 267:1456–1462, 1995.
Tibbetts *Cell*, 12:243–249, 1977.
Tsujimoto and Croce, *Proc. Natl. Acad. Sci. USA*, 83:5214, 1986.
Tsujimoto et al., *Science*, 226:1097, 1984.
Tsujimoto et al, *Science*, 228:1440, 1985.
Tur-Kaspaet al., *Mol. Cell Biol.*, 6:716–718, 1986.
Umbas et al., *Cancer Res.*, 52:5104–5109, 1992.
Veis et al., et al, *Cell*, 75:229, 1993.
Wagner et al., *Proc. Natl. Acad. Sci.* 87(9):3410–3414, 1990.
Wagner et al., *Science*, 260:1510–1513, 1993.
Walther and Stein, *J. Mol. Med*, Vol. 74, 1996: pp. 379–392.
Wang et al., *Cell*, 87:629, 1996a.
Wang et al., *Genes. Dev.*, 10:2859, 1996c.
Wang et al., In: *Animal Cell Technology: Basic & Applied Aspects*, S. Kaminogawa et al., (eds), vol. 5, pp463–469, Kluwer Academic Publishers, Netherlands, 1993.
Wang et al., *J. Cell Biol.*, 129:1103, 1995.
Watt et al., *Proc. Natl. Acad. Sci.*, 83(2): 3166–3170, 1986.
Weinberg, *Science*, 254:1138–1145, 1991.
Wilson, et al., *Mol. Cell. Biol.*, 6181–6191, 1990.
Wong et al., *Gene*, 10:87–94, 1980.
Wu and Wu, *Adv. Drug Delivery Rev.*, 12:159–167, 1993.
Wu and Wu, *Biochem.*, 27:887–892, 1988.
Wu and Wu, *J. Biol. Chem.*, 262:4429–4432, 1987.
Xiao et al., *J. Virol.*, 70:8098–8108, 1996.
Yachnis et al, *J. Neuropath. Exp. Neurol.*, 56:186, 1997.
Yang et al., *Cell Biol.*, 128:1173, 1995a.
Yang et al., *Cell*, 80:285, 1995b.
Yang et al., *Proc. Natl. Acad. Sci USA*, 87:9568–9572, 1990.
Yin et al., *Curr. Top. Microbiol. Immunol.*, 194:331, 1995.
Yin et al., *Nature*, 369:272, 1994.
Yin et al., *Nature*, 385:637, 1997.
Yin, Knudson, Korsmeyer, Van Dyke, "Bax suppresses tumorigenesis and stimulates apoptosis in vivo," *Nature* 385:637–640, 1997.
Yuan et al., *Cell*, 75:641, 1993.
Zechner, et al, *Mol Cell. Biol.*, 2394–2401, 1988.
Zha et al., *Cell*, 87:619, 1996b.
Zha et al., *J. Biol. Chem.*, 271:7440, 1996a.
Zhan et al., *Oncogene*, 9:3743, 1994.
Zhang et al., *Hum. Gene Ther.*, 6:155–164, 1995. Zhang, Fang, Branch, Mazur, French, Roth, "Generation and identification of recombinant adenovirus by liposome-mediated transfection and PCR analysis," *Biotechniques.* 15:868–872, 1993.
Zutter et al, *Blood*, 78:1062, 1991.

What is claimed is:

1. An adenoviral expression construct comprising a first nucleic acid encoding a proapoptotic member of the Bcl-2 gene family and a non-adenoviral first promoter inducible by a non-adenoviral inducer polypeptide wherein said first nucleic acid is under transcriptional control of said first promoter.

2. The expression construct of claim 1, wherein said proapoptotic Bcl-2 family gene is a Bax, Bak, Bim, Bik, Bid, or Bad gene.

3. The expression construct of claim 1, further comprising a second nucleic acid encoding a second transgene.

4. The expression construct of claim 1, wherein said first promoter is tetracycline regulatable or ecdysone regulatable.

5. The expression construct of claim 1, wherein said expression construct is a replication-deficient adenovirus.

6. The expression construct of claim 1, further comprising a polyadenylation signal.

7. The expression construct of claim 1, wherein said first nucleic acid is a cDNA, or genomic DNA.

8. The expression construct of claim 1, wherein the first promoter is GAL4 and the inducer polypeptide is GAL4/VP16.

9. The expression construct of claim 2, wherein said proapoptotic Bcl-2 family gene is a Bak gene.

10. The expression construct of claim 2, wherein said proapoptotic Bcl-2 family gene is a Bax gene.

11. The expression construct of claim 3, wherein said second nucleic acid is under the control of said first promoter.

12. The expression construct of claim 3, wherein said proapoptotic Bcl-2 family gene and said second nucleic acid are separated by an IRES.

13. The expression construct of claim 3, wherein said second nucleic acid is under the control of a second promoter operative in eukaryotic cells.

14. The expression construct of claim 3, wherein said second trans gene trans gene encodes a protein selected from the group consisting of a tumor suppressor, a cytokine, a receptor, inducer of apoptosis, and differentiating agents.

15. The expression construct of claim 3, wherein said second nucleic acid is an antiapoptotic member of the Bcl-2 gene family or an oncogene, said second nucleic acid being positioned in an antisense orientation with respect to said promoter.

16. The expression construct of claim 3, wherein said second nucleic acid is a cDNA or genomic DNA.

17. The expression construct of claim 13, wherein said second promoter is selected from the group consisting of CMV IE, SV40 IE, RSV, β-actin, tetracycline regulatable and ecdysone regulatable.

18. The expression construct of claim 13, wherein said second nucleic acid encodes said inducer polypeptide.

19. The expression construct of claim 14, wherein said tumor suppressor is selected from the group consisting of p53, p16, p21, MMAC1, p73, zac1, C-CAM, BRCAI and Rb.

20. The expression construct of claim 14, wherein said inducer of apoptosis is selected from the group consisting of Harakiri, Ad E1 B and an ICE-CED3 protease.

21. The expression construct of claim 14, wherein said cytokine is selected from the group consisting of IL-2, IL-3, IL-4, IL-5, IL-6, IL-7, IL-8, IL-9, IL-10, IL-11, IL-12, IL-13, IL-14, IL-15, TNF, GMCSF, β-interferon and γ-interferon.

22. The expression construct of claim 14, wherein said receptor is selected from the group consisting of CFTR, EGFR, VEGFR, IL-2 receptor and the estrogen receptor.

23. The expression construct of claim 15, wherein said antiapoptotic member of the Bcl-2 gene family is Bcl-2 or Bcl-$x_L$.

24. The expression construct of claim 15, wherein said oncogene is selected from the group consisting ras, myc, neu, raf erb, src, fms, jun, trk, ret, gsp, hst, and abl.

25. The expression construct of claim 5, wherein said adenovirus lacks at least a portion of the E1 region.

26. The expression construct of claim 5, wherein said adenovirus further lacks the E3 coding region.

27. The expression construct of claim 10, wherein said Bax gene expresses a truncated Bax protein.

28. The expression construct of claim 27, wherein said truncated Bax protein comprises an intact death domain.

29. The expression construct of claim 27, wherein said truncated Bax protein comprises SEQ ID NO:2.

30. The expression construct of claim 27, wherein said truncated Bax protein comprises a BH3 region.

31. A pharmaceutical composition comprising:
  (i) a first adenoviral expression construct comprising a promoter functional in eukaryotic cells and a first nucleic acid encoding a proapoptotic member of the Bcl-2 gene family, wherein said first nucleic acid is under transcriptional control of said promoter and;
  (ii) a pharmaceutically acceptable buffer, solvent or diluent.

32. The pharmaceutical composition of claim 31, wherein said proapoptotic Bcl-2 family gene is a Bax, Bak, Bik, Bid, or Bad gene.

33. The pharmaceutical composition of claim 31, wherein said promoter is selected from the group consisting of CMV IE, SV40 IE, RSV, β-actin, tetracycline regulatable and ecdysone regulatable.

34. The pharmaceutical composition of claim 31, further comprising a second expression construct encoding a second nucleic acid encoding a second gene operatively linked to a second promoter.

35. The pharmaceutical composition of claim 31, wherein said expression construct further comprises a second nucleic acid encoding a second gene.

36. The pharmaceutical composition of claim 34, wherein said second promoter is selected from the group consisting of CMV IE, SV40 IE, RSV, β-actin, tetracycline regulatable and ecdysone regulatable.

37. The pharmaceutical composition of claim 35, wherein said second nucleic acid is under the control of said first promoter.

38. The pharmaceutical composition of claim 35, wherein said second nucleic acid is under the control of a second promoter operative in eukaryotic cells.

39. The pharmaceutical composition of claim 35, wherein said second gene encodes a protein selected from the group consisting of a tumor suppressor, a cytokine, a receptor, inducer of apoptosis, and differentiating agents.

40. The pharmaceutical composition of claim 35, wherein said second nucleic acid is an antiapoptotic member of the Bcl-2 gene family or an oncogene, said second nucleic acid being positioned in an antisense orientation with respect to said promoter.

41. A nucleic acid encoding a truncated Bax CDNA.

42. The nucleic acid of claim 41, wherein said Bax CDNA comprises a nucleic acid sequence of SEQ ID NO: 1.

43. The nucleic acid of claim 41, wherein said Bax CDNA encodes a protein having an amino acid sequence of SEQ ID NO:2.

44. The nucleic acid of claim 41, wherein said truncated Bax CDNA encodes a protein comprising a BH3 region.

45. The nucleic acid of claim 41, wherein said truncated Bax CDNA encodes a protein comprising an intact death domain.

46. An adenoviral expression construct comprising a nucleic acid encoding a truncated Bax gene and a first promoter functional in eukaryotic cells wherein said nucleic acid is under transcriptional control of said first promoter.

47. A kit comprising:
  (a) a first vector comprising
    (i) a first promoter inducible by an inducer polypeptide;
    (ii) a multipurpose cloning site 3' to said first promoter;
    (iii) a proapoptotic member of the Bcl-2 gene family in a suitable container; and
  (b) a second vector comprising a coding region for said inducer polypeptide under the control of a second promoter, said second vector in a suitable container.

48. The kit of claim 47, wherein said first vector further comprises a region coding for a polypeptide under control of said first promoter.

49. The kit of claim 47, wherein said second promoter is an inducible promoter and said kit further comprises an agent that induces said second promoter in a suitable container means.

* * * * *

SEQUENCE LISTING

<160> NUMBER OF SEQ ID NOS: 10

<210> SEQ ID NO 1
<211> LENGTH: 578
<212> TYPE: DNA
<213> ORGANISM: Human

<400> SEQUENCE: 1

```
atggacgggt ccggggagca gcccagaggc gggggtccca ccagctctga gcagatcatg      60
aagacagggg ccctttttgct tcagggtttc atccaggatc gagcagggcg aatggggggg    120
gaggcacccg agctggccct ggacccggtg cctcaggatg cgtccaccaa gaagctgagc    180
gagtgtctca gcgcatcgg ggacgaactg gacagtaaca tggagctgca gaggatgatt    240
gccgccgtgg acacagactc ccccgagag gtcttttttcc gagttgcagc tgacatgttt    300
tctgacggca acttcaactg gccgggttg tcgcccttt ctactttgcc agcaaactgg     360
tgctcaaggc cctgtgcacc aaggtgccgg aactgatcag aaccatcatg ggctggacat    420
tggacttcct ccgggagcgg ctgttgggct ggatccaaga ccagggtggt tgggacggcc    480
tcctctccta ctttgggacg cccacgtggc agaccgtgac catctttgtg gcgggagtgc    540
tcaccgcctc gctcaccatc tggaagaaga tgggctga                           578
```

<210> SEQ ID NO 2
<211> LENGTH: 131
<212> TYPE: PRT
<213> ORGANISM: Human

<400> SEQUENCE: 2

```
Met Asp Gly Ser Gly Glu Gln Pro Arg Gly Gly Pro Thr Ser Ser
  1               5                  10                  15

Glu Gln Ile Met Lys Thr Gly Ala Leu Leu Leu Gln Gly Phe Ile Gln
                 20                  25                  30

Asp Arg Ala Gly Arg Met Gly Gly Glu Ala Pro Glu Leu Ala Leu Asp
             35                  40                  45

Pro Val Pro Gln Asp Ala Ser Thr Lys Lys Leu Ser Glu Cys Leu Lys
         50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Ala Gly Leu Ser Pro
            100                 105                 110

Phe Ser Thr Leu Pro Ala Asn Trp Cys Ser Arg Pro Cys Ala Pro Arg
        115                 120                 125

Cys Arg Asn
        130
```

<210> SEQ ID NO 3
<211> LENGTH: 579
<212> TYPE: DNA
<213> ORGANISM: Human

<400> SEQUENCE: 3

```
atggacgggt ccggggagca gcccagaggc ggggggccca ccagctctga gcagatcatg      60
aagacagggg ccctttttgct tcagggtttc atccaggatc gagcagggcg aatggggggg    120
```

```
gaggcacccg agctggccct ggacccggtg cctcaggatg cgtccaccaa gaagctgagc      180
gagtgtctca agcgcatcgg ggacgaactg gacagtaaca tggagctgca gaggatgatt      240
gccgccgtgg acacagactc cccccgagag gtcttttttcc gagtggcagc tgacatgttt     300
tctgacggca acttcaactg gggccgggtt gtcgcccttt tctactttgc cagcaaactg      360
gtgctcaagg ccctgtgcac caaggtgccg gaactgatca gaaccatcat gggctggaca      420
ttggacttcc tccgggagcg gctgttgggc tggatccaag accagggtgg ttgggacggc      480
ctcctctcct actttgggac gcccacgtgg cagaccgtga ccatctttgt ggcgggagtg      540
ctcaccgcct cgctcaccat ctggaagaag atgggctga                             579

<210> SEQ ID NO 4
<211> LENGTH: 192
<212> TYPE: PRT
<213> ORGANISM: Human

<400> SEQUENCE: 4

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 5
ggaattcgcg gtgatggacg ggtccgg                                          27

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
```

-continued

```
<400> SEQUENCE: 6
gggaattctc agcccatctt cttccaga                                              28

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 7
gggacgaact ggacagtaa                                                        19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 8
gcaccagttt gctggcaaa                                                        19

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 9
acgcaaatgg gcggtag                                                          17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 10
caactagaag gcacagt                                                          17
```